United States Patent
Canard et al.

(10) Patent No.: US 8,884,011 B2
(45) Date of Patent: Nov. 11, 2014

(54) NUCLEOTIDE ANALOGUES AS PRECURSOR MOLECULES FOR ANTIVIRALS

(75) Inventors: Bruno Canard, Cassis (FR); Karine Alvarez, Marseilles (FR); Karine Barral, Marseilles (FR); Jean-Louis Romette, Marseilles (FR); Johan Neyts, Kessel-Lo (BE); Jan Balzarini, Heverlee (BE)

(73) Assignees: Centre National de la Recherche Scientifique-CNRS, Paris (FR); Universite d'Aix-Marseille, Marseilles (FR); K.U. Leuven Research & Development, Leuven (BE)

( * ) Notice: Subject to any disclaimer, the term of this patent is extended or adjusted under 35 U.S.C. 154(b) by 989 days.

(21) Appl. No.: 12/514,285

(22) PCT Filed: Nov. 8, 2007

(86) PCT No.: PCT/IB2007/004233
§ 371 (c)(1),
(2), (4) Date: Nov. 20, 2009

(87) PCT Pub. No.: WO2008/056264
PCT Pub. Date: May 15, 2008

(65) Prior Publication Data
US 2010/0099869 A1    Apr. 22, 2010

(30) Foreign Application Priority Data
Nov. 8, 2006  (FR) ..................................... 06 09749

(51) Int. Cl.
C07F 9/02      (2006.01)
C07F 9/6561    (2006.01)

(52) U.S. Cl.
CPC .................................. C07F 9/65616 (2013.01)
USPC ....................................................... 544/244

(58) Field of Classification Search
USPC ............................... 544/229, 244; 514/64, 81
See application file for complete search history.

(56) References Cited

U.S. PATENT DOCUMENTS

| | | | |
|---|---|---|---|
| 4,935,427 A | 6/1990 | Broder et al. | |
| 5,072,032 A | 12/1991 | McKenna | |
| 5,663,159 A | 9/1997 | Starrett, Jr. et al. | |

FOREIGN PATENT DOCUMENTS

| | | |
|---|---|---|
| CN | 1 523 028 A | 8/2004 |
| CN | 1 634 943 A | 7/2005 |
| CN | 1 810 816 A | 8/2006 |
| EP | 0 205 826 A2 | 12/1986 |
| EP | 0 206 459 A2 | 12/1986 |
| EP | 0 253 412 A2 | 1/1988 |
| WO | WO 93/07157 | 4/1993 |
| WO | WO 03/002580 A1 | 1/2003 |
| WO | WO 2004/111064 A | 12/2004 |
| WO | WO 2006/114064 A2 | 11/2006 |

OTHER PUBLICATIONS

Barral, J. Med. Chem. 2006, 49, 7799-7806.*
Arimilli et al., "Synthesis, in vitro biological evaluation and oral bioavailability of 9-[2-(phosphonomethoxy)propyl]adenine (PMPA) prodrugs", Antiviral Chemistry & Chemotherapy, 1997 8(6), pp. 557-564.
Wallace T. Ashton et al., "Synthesis and Antiherpetic Activity of (±)-9-[[Z)-2-(Hydroxymethyl)cyclopropyl]methyl]guanine and Related Compounds", J. Med. Chem. 1988, 31, pp. 2304-2315.
F. Barré-Sinoussi et al., Isolation of a T-Lymphotropic Retrovirus from a Patient at Risk for Acquired Immune Deficiency Syndrome (AIDS), Science, New Series, vol. 220, No. 4599 (May 20, 1983), pp. 868-871.
Samira Benzaria et al., "Synthesis, in Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability," J. Med. Chem. 1996, 39, pp. 4958-4965.
Stephen M. Berge et al., "Pharmaceutical Salts", Journal of Pharmaceutical Sciences, Jan. 1977, vol. 66, No. 1, pp. 1-19.

(Continued)

*Primary Examiner* — Alicia L Otton
(74) *Attorney, Agent, or Firm* — Arent Fox LLP

(57) ABSTRACT

This invention relates to a purine or pyrimidine phosphonate compound of formula (I)

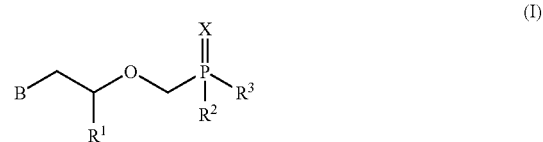

or pharmaceutically acceptable salt thereof; wherein B, X, and $R^1$-$R^3$ are as defined in classes and subclasses herein. These compounds may be used as antiviral precursors. The invention also relates to therapeutic compositions of these compounds and their use for the preparation of a medication for testing and/or preventing a viral infection in a patient. The invention also provides methods for making these compounds. In particular, the invention provides an H-phosphinate precursor intermediate of formula (II)

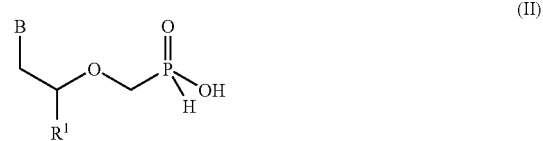

wherein B is a purine or pyrimidine base as defined herein and $R^1$ is selected from the group comprising a hydrogen atom, and a methyl, ethyl, hydroxymethyl, hydroxyethyl and $C_{1-6}$haloalkyl group.

17 Claims, 1 Drawing Sheet

(56) References Cited

OTHER PUBLICATIONS

Joëlle Borreto et al., "An Integrated System to Study Multiply Substituted Human Immunodeficiency Virus Type 1 Reverse Transcriptase", Analytical Biochemistry, 292, pp. 139-147 (2001).
Nicholas A. Boyle et al., Synthesis of 2',3'-Dideoxynucleoside 5'-α-P-Borano-β, γ-(difluoromethylene)triphosphates and Their Inhibition of HIV-1 Reverse Transcriptase, J. Med. Chem. 2005, 48, pp. 2695-2700.
Theodora Calogeropoulou et al., "Strategies in the Design of Prodrugs of Anti-HIV Agents", Current Topics in Medicinal Chemistry 2003, 3, pp. 1467-1495.
Erik De Clercq, "Toward Improved Anti-HIV Chemotherapy: Therapeutic Strategies for Intervention with HIV Infections", Journal of Medicinal Chemistry, Perspective, vol. 38, No. 14, Jul. 5, 1995, pp. 2491-2517.
Antoine Frangeul et al., "In Vitro Suppression of K65R Reverse Transcriptase-Mediated Tenofovir- and Adefovir-5'-Diphosphate Resistance Conferred by the Boranophosphonate Derivatives", Antimicrobial Agents Chemotherapy 2007, vol. 51, No. 9, pp. 3162-3167.
Kaizhang He et al., "Synthesis and Separation of Diastereomers of Ribonucleoside 5'-(α-P-Borano)triphosphates," J. Org. Chem. 1998, 63, pp. 5769-5773.
S. K. Ladner et al., "Inducible expression of human hepatitis B virus (HBV) in stably transfected hepatoblastoma cells: a novel system for screening potential inhibitors of HBV replication", Antimicrobial Agents and Chemotherapy, Aug. 1997, vol. 41, No. 8, pp. 1715-1720.
Alf Larsson et al., "Mode of Action, Toxicity, Pharmacokinetics, and Efficacy of Some New Antiherpesvirus Guanosine Analogs Related to Buciclovir", Antimicrobial Agents and Chemotherapy, Oct. 1986, vol. 30, No. 4, pp. 598-605.
Ping Li et al., "Synthesis of Nucleoside Boranophosphoramidate Prodrugs Conjugated with Amino Acids," J. Org. Chem. 2005, 70, pp. 2171-2183.
Ping Li et al., "Synthesis of Prodrug Candidates: Conjugates of Amino Acid with Nucleoside Boranophosphate," Organic Letters, 2002, vol. 4, No. 12, pp. 2009-2012.
Jinlai Lin et al., "Synthesis of a boron analogue of glucose-conjugated nucleoside diphosphate: nucleoside α-P-boranodiphosphoglucose," Tetrahedron Letters, 41 (2000) pp. 6701-6704.
C. Meier, "Pro-Nucleotides—Recent Advances in the Design of Efficient Tools for the Delivery of Biologically Active Nucleoside Monophosphates," New Tools in Synthesis, Synlett, pp. 233-242 (1998).

Michael D. Miller, "K65R, TAMS and Tenofovir", AIDS Reviews 2004;6, pp. 22-33.
Christian Périgaud et al., "Rational Design for Cytosolic Delivery of Nucleoside Monophosphates: "SATE" and "DTE" as Enzyme-Labile Transient Phosphate Protecting Groups", Bioorganic & Medicinal Chemistry Letters, vol. 3, No. 12, pp. 2521-2526 (1993).
Frédéric Puech et al., "Intracellular delivery of nucleoside monophosphates through a reductase-mediated activation process", Antiviral Research, 22 (1993), pp. 155-174.
Brian L. Robbins et al., Anti-Human Immunodeficiency Virus Activity and Cellular Metabolism of a Potential Prodrug of the Acyclic Nucleoside Phosphonate 9-$R$-(2-Phosphonomethoxypropyl) adenine (PMPA), Bis(isopropyloxymethylcarbonyl)PMPA, Antimicrobial Agents and Chemotherapy, Mar. 1998, vol. 42, No. 3, pp. 612-617.
Jean-Claude Schmit et al., "Evolution of HIV drug resistance in zidovudine/zalcitabine- and zidovudine/didanosine-experienced patients receiving lamivudine-containing combination therapy," Antiviral Therapy 3, pp. 81-88 (1998).
John E. Starrett, Jr. et al., "Synthesis and in vitro evaluation of a phosphonate prodrug: bis(pivaloyloxymethyl) 9-(2-phosphonylmethoxyethyl)adenine," Antiviral Research, 19 (1992), pp. 267-273.
Jeno Tomasz et al., "5'-$P$-Borane-Substituted Thymidine Monophosphate and Triphosphate," Angew. Chem. Int. Ed. Engl. 1992, vol. 31, No. 10, pp. 1373-1375.
Joshua D. Thomas et al., "Overcoming steric effects in the coupling reaction of alkyloxycarbonyloxymethyl (AOCOM) halides with phenols: an efficient synthesis of AOCOM phenolic prodrugs", Tetrahedron Letters, 48 (2007), pp. 109-112.
Kristel Van Laethem et al., "Patient HIV-1 strains carrying the multiple nucleoside resistance mutations are cross-resistant to abacavir," correspondence. AIDS 2000, vol. 14, No. 4, pp. 469-471.
Mark A. Wainberg et al., "In vitro selection and characterization of HIV-1 with reduced susceptibility to PMPA", Antiviral Therapy, 4, pp. 87-89 (1999).
Carston R. Wagner et al., "Aromatic Amino Acid Phosphoramidate Di- and Triesters of 3'-Azido-3'-Deoxythymidine (AZT) Are Non-Toxic Inhibitors of HIV-1 Replication," Bioorganic & Medicinal Chemistry Letters, vol. 5, No. 16, pp. 1819-1824, 1995.
Guangyi Wang et al., "Synthesis of AZT 5'-Triphosphate Mimics and Their Inhibitory Effects on HIV-1 Reverse Transcriptase," J. Med. Chem, 2004, 47, pp. 6902-6913.

\* cited by examiner

NUCLEOTIDE ANALOGUES AS PRECURSOR MOLECULES FOR ANTIVIRALS

CROSS-REFERENCE TO RELATED APPLICATION

This application is a National Stage entry of International Application No. PCT/IB2007/004233, filed Nov. 8, 2007, the entire specification claims and drawings of which are incorporated herewith by reference.

PRIORITY

The present application claims priority to French Patent Application Nos.: FR 06/09749 filed on Nov. 8, 2006, the entire contents of which are incorporated herein by reference.

FIELD OF THE INVENTION

This invention relates to novel nucleotide analogues, a method for their synthesis from a common intermediate compound and their use as antiviral precursors.

BACKGROUND OF THE INVENTION

Viruses are the etiologic cause of many life-threatening human diseases. Of special importance are the human immunodeficiency virus (HIV) and the hepatitis B virus (HBV).

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). According to the Joint United Nations Programme on HIV/AIDS, 40 million people are estimated to be living with HIV/AIDS at the end of 2006. During that same year, AIDS caused the deaths of an estimated 3 million people, and it was estimated that over 4 million people were infected by AIDS in 2006.

Another virus that causes a serious human health problem is the hepatitis B virus (referred to below as "HBV"). Hepatitis B virus (HBV) is a virus that causes chronic disease responsible for serious liver damage, including cirrhosis of the liver, cancer, organ failure and ultimately, death. HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone. It is estimated that approximately 300 million people worldwide are infected with HBV. The epidemiology of HBV is very similar to that of acquired immune deficiency syndrome, which accounts for why HBV infection is common among patients with AIDS or AIDS related complex. However, HBV is more contagious than HIV. Although use of a prophylactic vaccine has reduced the incidence of new HBV infections, there continues to be a need for an effective therapeutic drug. Various derivatives of nucleoside analogues have been found to exhibit antiviral activity. Notably, acyclovir (Zovirax) and its prodrug valacyclovir (Valtrex) are approved drugs for infections caused by HSV-1 and HSV-2. Acyclovir Therapy for Herpesvirus Infections (Baker, Ed.), M. Dekker, New York (1990); Against HCMV, four drugs are currently available: Ganciclovir (Cytovene), cidofovir (Vistide), antisense oligonucleotide fomivirsen (Vitravene) and foscarnet (Foscavir). However, only ganciclovir is effective orally but it requires large doses and produces potentially serious adverse effects such as bone marrow suppression. Ganciclovir Therapy for Cytomegalovirus Infection (Spector, S. S., Ed.), M. Dekker, New York (1991). A considerable effort went into design, synthesis and biological investigation of analogues of these drugs as well as in development of new antiviral agents. Larsson, A., et al., Antimicrob. Agents & Chemother. 30:598-605 (1986); Ashton, W. T., et al., J. Med. Chem. 31:2304-2315 (1988). Cidofovir and fomivirsen are approved only for topical application against retinitis in AIDS patients and foscarnet is used only by intravenous route and it leads to characteristic toxicity.

Current drugs for AIDS include AZT (zidovudine, Retrovir), ddI (didanosine, Videx), ddC (zalcitabine, Hivid) and d4T (stavudine, Zerit). De Clercq, E., J. Med. Chem. 38:2491-2517 (1995). Allenic nucleoside analogues such as adenallene and cytallene are examples of anti-HIV agents containing an unsaturated alkyl group. U.S. Pat. No. 4,935,427; Zemlicka, J., Allenols Derived from Nucleic Acid Bases—a New Class of Anti-HIV Agents: Chemistry and Biological Activity in Nucleosides and Nucleotides as Antitumor and Antiviral Agents (Chu, C. K.; Baker, D. C., Eds.), Plenum Press, New York, pp. 73-100 (1993). For HBV, alpha interferon and 3TC (lamivudine; Epivir) are two drugs licensed for the treatment of persons with chronic HBV infection. Unfortunately, only about 40% of patients respond to these drugs and resistance is a growing problem.

GILEAD is currently marketing two acyclic nucleotide phosphonate antiviral molecules: cidofovir or HPMC (VISTIDE®) against cytomegalovirus (CMV) and tenofovir or (R)-PMPA in the a pro-drug form (VIREAD®). Incidentally, tenofovir received FDA approval in October 2001 for monotherapy against HIV-1 and obtained an "AMM" [Market Authorization] in Europe in February 2002. It also developed adefovir or PMEA, for the treatment of HBV (HEPSERA®).

These compounds are also confronted to resistance problems. For example, it is recognized that the only mutation against Tenofovir directly selected at low frequency is the K65R mutation (Wainberg, M. A.; Miller, M. D.; Quan, Y.; Salomon, H.; Mulato, A. S.; Lamy, P. D.; Margot, N. A.; Anton, K. E.; Chemington, J. M. In vitro selection and characterization of HIV-1 with reduced susceptibility to PMPA. *Antiviral Therapy* 1999, 4, 87). However, it has been shown that thymidine analogue resistance mutations (TAMs) considerably reduce the effectiveness of Tenofovir when there are more than 3 mutations, preferentially with M41L and L210W, suggesting that the TAMs excise the Tenofovir. The excision of PMPA by the TAMs is a major point in the current resistance of HIV-1 associated with this compound (Miller, M. K65R, TAMS and tenofovir. *AIDS Rev* 2004, 6, 22).

However, the synthesis of such molecules in quantitative yields proves difficult. Thus, in light of the growing problems with viral resistance to the retrovirals used today, there remains a need to rapidly develop effective new antivirals.

DETAILED DESCRIPTION OF CERTAIN PREFERRED EMBODIMENTS OF THE INVENTION

The present invention specifically addresses this need by providing effective new antiviral compounds.

The polymerase enzyme of a virus is essential for the viral replication process. After infection of a target cell by a virus, the polymerase catalyses the synthesis of the viral genome and the reproduction of the virus, resulting in a persistent infection. As a result, this enzyme represents a privileged target for antiviral treatments because of its important role in the replication of the virus.

Nucleoside inhibitors are the first class of anti-retrovirals which has proven its clinical effectiveness. As such, they play an important role in current anti-retroviral treatments. This class of medications is the subject of very active therapeutic research with the purpose of developing analogues that perform better than those currently used therapeutically, i.e., analogues exhibiting higher powerful antiviral activity and/or a pharmacological profile.

With respect to their mode of action, these nucleoside analogues are phosphorylated by cellular kinases into 5'-triphosphates after penetration into the infected cell. While they are generally poor substrates for cellular polymerases, these nucleoside analogues are on the other hand incorporated into the growing viral DNA chain mediated by the action of reverse transcriptase (RT). As these analogues do not possess a 3'-OH group, their incorporation produces a termination of DNA synthesis that is responsible for the antiviral effect.

Phosphonate nucleotide analogues in which one of the oxygen atoms single-bonded to the phosphorus in a position is substituted by a $CH_2$ group, isosteric and isoelectronic with the phosphates, have been widely studied, and the work of A. HOLY in particular are pioneering in this field of synthesis of acyclic phosphonate analogues.

The principal significance of the phosphonates lies in the fact that they are monophosphate compounds that make it possible to bypass the initial phosphorylation step, often limiting in the effectiveness of a nucleoside analogue. They present good chemical and enzymatic stability and a long lifetime in biological fluids and cells. Their mode of cellular penetration as well as their intracellular phosphorylation has been described (ROBBINS et al., *Antimicrob. Agents Chemother.*, vol. 42(3), p. 612-617, 1998).

Unfortunately, with the emergence of resistant viruses, treatments using nucleoside analogues rapidly lose their effectiveness over time. This viral resistance is due to the appearance of mutations in the pol gene coding for reverse transcriptase. Thus, each nucleotide analogue selects mutations that are the origin of RT resistance mechanisms. The abundance of HIV-1 strains resistant to several antiviral molecules makes the current situation very worrisome: it has become increasingly frequent that such viral strains might be acquired as early as the primary infection of a patient, who then finds himself in a therapeutic impasse.

Accordingly, the development of new antivirals that are more potent and above all more active against resistant strains becomes increasingly important in an effort to optimise antiviral therapies combining several medications.

Compounds of this invention include those generally set forth above and described specifically herein, and are illustrated in part by the various classes, subgenera and species disclosed herein. Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In a first object of the invention there is provided a purine or pyrimidine phosphonate derivative of formula (I):

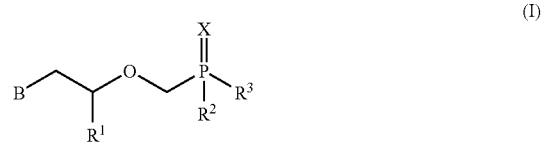

(I)

or pharmaceutically acceptable salt thereof;
wherein:
B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, cytosine, uracil, 5-bromouracil, 5-iodouracil, 5-ethyluracil, 5-propyluracil, 5-vinyluracil and 5-bromovinyluracil;

$R^1$ is selected from the group comprising a hydrogen atom, and a methyl, ethyl, hydroxymethyl, hydroxyethyl and haloalkyl group;

$R^2$ is selected from the group comprising a fluorine atom, a hydroxyl group or alkaline metal salt thereof, $—OR^{2,4}$, a prodrug moiety, $—BH_3$, a linear or branched alkyl, alkenyl, alkynyl, heteroalkyl, heteroalkenyl or heteroalkynyl group, and an amine group R'HN wherein $R^{2,4}$ represents alkyl, alkenyl, alkynyl, heteroalkyl, heteroalkenyl, heteroalkynyl, $—P(=O)(OH)_2$ or alkaline metal salt thereof, $—P(=O)(OH)OP(=O)(OH)_2$, or alkaline metal salt thereof, and $R^1$ is a linear or branched alkyl, alkenyl, alkynyl, heteroalkyl, heteroalkenyl, heteroalkynyl or aryl group, or an amino acid residue;

$R^3$ is selected from the group comprising a hydroxyl group or alkaline metal salt thereof, $—OR^{3,4}$, a prodrug moiety, and an amine group R"HN, wherein $R^{3,4}$ represents alkyl, alkenyl, alkynyl, heteroalkyl, heteroalkenyl, heteroalkynyl, $—P(=O)(OH)_2$ or alkaline metal salt thereof, or $—P(=O)(OH)OP(=O)(OH)_2$ or alkaline metal salt thereof, and R" is a linear or branched alkyl, alkenyl, alkynyl, heteroalkyl, heteroalkenyl, heteroalkynyl or aryl group, or an amino acid residue; and X is selected from the group comprising an oxygen atom, a selenium atom and a sulphur atom.

In certain embodiments, compounds of formula (I) are as defined below:
B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, cytosine, uracil, 5-bromouracil, 5-iodouracil, 5-ethyluracil, 5-propyluracil, 5-vinyluracil and 5-bromovinyluracil;

$R^1$ is selected from the group comprising a hydrogen atom, and a methyl, ethyl, hydroxymethyl, hydroxyethyl and $C_{1-6}$haloalkyl group;

R² is selected from the group comprising a fluorine atom, a hydroxyl group or alkaline Metal salt thereof, —OR²ᴬ, a prodrug moiety, —BH₃, a linear or branched $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R'HN, wherein R²ᴬ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)₂ or alkaline metal salt thereof, —P(=O)(OH)OP(=O)(OH)₂, or alkaline metal salt thereof, and R' is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue;

R³ is selected from the group comprising a hydroxyl group or alkaline metal salt thereof, —OR³ᴬ, a prodrug moiety, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R"HN, wherein R³ᴬ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)₂ or alkaline metal salt thereof, or —P(=O)(OH)OP(=O)(OH)₂ or alkaline metal salt thereof, and R" is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue; and X is selected from the group comprising an oxygen atom, a selenium atom and a sulphur atom.

In certain embodiments, compounds of the invention are defined as follows:

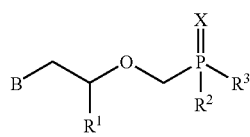

(I)

or pharmaceutically acceptable salt thereof;
wherein:
R³ is as defined above;
B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, cytosine, uracil, 5-bromouracil, 5-iodouracil, 5-ethyluracil, 5-propyluracil, 5-vinyluracil and 5-bromovinyluracil;
R¹ is selected from the group comprising a hydrogen atom, and a methyl, ethyl, hydroxymethyl and hydroxyethyl and $C_{1-6}$haloalkyl group;
(a) X is selected from the group comprising a selenium atom and a sulphur atom, and R² is selected from the group comprising a fluorine atom, a hydroxyl group or alkaline metal salt thereof, —OR²ᴬ, a prodrug moiety, —BH₃, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R'HN wherein R²ᴬ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)₂ or alkaline metal salt thereof, —P(=O)(OH)OP(=O)(OH)₂, or alkaline metal salt thereof, and R' is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue; or
(b) X represents an oxygen atom, and R² is selected from the group comprising a fluorine atom and a BH₃ group.

In certain embodiments, the phosphonate derivative has the following structure:

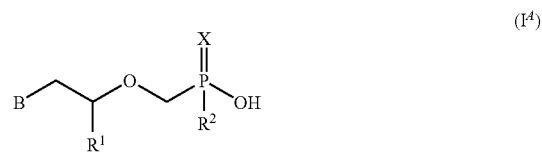

(I⁴)

or pharmaceutically acceptable salt thereof;
wherein:
B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, cytosine, uracil, 5-bromouracil, 5-iodouracil, 5-ethyluracil, 5-propyluracil, 5-vinyluracil and 5-bromovinyluracil;
R¹ is selected from the group comprising a hydrogen atom, and a methyl, ethyl, hydroxymethyl, hydroxyethyl and $C_{1-8}$haloalkyl group;
R² is selected from the group comprising a fluorine atom, a hydroxyl group or alkaline metal salt thereof, —OR²ᴬ a prodrug moiety, —BH₈, a linear or branched $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R'HN wherein R²ᴬ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)₂ or alkaline metal salt thereof, —P(=O)(OH)OP(=O)(OH)₂, or alkaline metal salt thereof, and R' is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue; and X is selected from the group comprising an oxygen atom, a selenium atom and a sulphur atom.

In certain embodiments, the phosphonate derivative has the following structure:

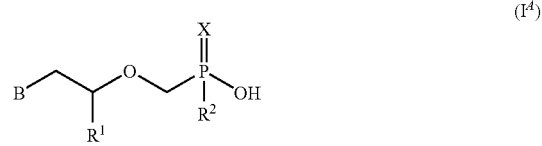

(I⁴)

or a pharmaceutically acceptable salt thereof,
wherein:
B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminoguanine, 2,6-diaminopurine, thymine, cytosine, uracil, 5-bromouracil, 5-iodouracil, 5-ethyluracil, 5-propyluracil, 5-vinyluracil and 5-bromovinyluracil;
R¹ is selected from the group comprising a hydrogen atom, and a methyl, ethyl, hydroxymethyl, hydroxyethyl and $C_{1-6}$haloalkyl group; and
(a) X is selected from the group comprising a selenium atom and a sulphur atom, and R² is selected from the group comprising a fluorine atom, a hydroxyl group or alkaline metal salt thereof, —OR$^{2A}$, a prodrug moiety, —BH$_3$, a linear or branched C$_{1-8}$alkyl, C$_{2-8}$alkenyl, C$_{2-8}$alkynyl, C$_{1-8}$heteroalkyl, C$_{2-8}$heteroalkenyl or C$_{2-8}$heteroalkynyl group, and an amine group R'HN wherein R$^{2A}$ represents C$_{1-8}$alkyl, C$_{2-8}$alkenyl, C$_{2-8}$alkynyl, C$_{1-8}$heteroalkyl, C$_{2-8}$heteroalkenyl, C$_{2-8}$heteroalkynyl, —P(=O)(OH)$_2$ or alkaline metal salt thereof, —P(=O)(OH)OP(=O)(OH)$_2$, or alkaline metal salt thereof, and R' is a linear or branched C$_{1-8}$alkyl, C$_{2-8}$alkenyl, C$_{2-8}$alkynyl, C$_{1-8}$heteroalkyl, C$_{2-8}$heteroalkenyl, C$_{2-8}$heteroalkynyl, C$_{8-10}$aryl group or an amino acid residue; or (b) X represents an oxygen atom, and R$^2$ is selected from the group comprising a fluorine atom, and a BH$_3$ group.

In certain embodiments, the phosphonate derivative has the following structure:

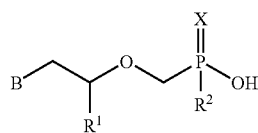

(I$^A$)

or a pharmaceutically acceptable salt thereof,
wherein:
B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminoguanine, 2,6-diaminopurine, thymine, cytosine, uracil, 5-bromouracil, 5-iodouracil, 5-ethyluracil, 5-propyluracil, 5-vinyluracil and 5-bromovinyluracil;
R$^1$ is selected from the group comprising a hydrogen atom, and a methyl, ethyl, hydroxymethyl and hydroxyethyl group; and
(a) X is selected from the group comprising a selenium atom and a sulphur atom, and R$^2$ is selected from the group comprising a fluorine atom, a hydroxyl group, —BH$_3$, a linear or branched C$_{1-8}$alkyl group, and an amine group R'HN wherein R$^1$ is a linear or branched C$_{1-8}$alkyl, group; or
(b) X represents an oxygen atom, and R$^2$ is selected from the group comprising a fluorine atom, a BH$_3$ group, and a linear or branched C$_{1-8}$alkyl group.

In certain embodiments, the phosphonate derivative has the following structure:

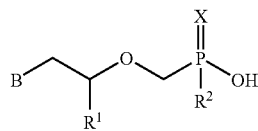

(I$^A$)

or pharmaceutically acceptable salt thereof;
wherein:
B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, cytosine, uracil, 5-bromouracil, 5-iodouracil, 5-ethyluracil, 5-propyluracil, 5-vinyluracil and 5-bromovinyluracil;
R$^1$ is selected from the group comprising a hydrogen atom, and a methyl, ethyl, hydroxymethyl and hydroxyethyl group;

R$^2$ is selected from the group comprising a fluorine atom, a hydroxyl group, —BH$_3$, a linear or branched C$_{1-8}$alkyl, and an amine group R'HN wherein R' is a linear or branched C$_{1-8}$alkyl group; and
X is selected from the group comprising an oxygen atom, a selenium atom and a sulphur atom.

In certain embodiments, the present invention defines particular classes of compounds which are of special interest. For example, one class of compounds of special interest includes compounds of formula (I$^B$):

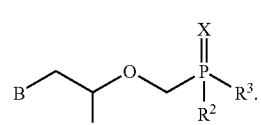

(I$^B$)

or pharmaceutically acceptable salt thereof;
wherein:
B is as defined above;
X is S or Se;
R$^1$ is selected from the group comprising a hydrogen atom, and a methyl, ethyl, hydroxymethyl hydroxymethyl, hydroxyethyl and C$_{1-6}$haloalkyl group;
R$^2$ is selected from the group comprising a fluorine atom, a hydroxyl group or alkaline metal salt thereof, —OR$^{2A}$, a prodrug moiety, —BH$_3$, a linear or branched C$_{1-8}$alkyl, C$_{2-8}$alkenyl, C$_{2-8}$alkynyl, C$_{1-8}$heteroalkyl, C$_{2-8}$heteroalkenyl or C$_{2-8}$heteroalkynyl group, and an amine group R$^1$ HN; wherein R$^{2A}$ represents C$_{1-8}$alkyl, C$_{2-8}$alkenyl, C$_{2-8}$alkynyl, C$_{1-8}$heteroalkyl, C$_{2-8}$heteroalkenyl, C$_{2-8}$heteroalkynyl, —P(=O)(OH)$_2$ or alkaline metal salt thereof, —P(=O)(OH)OP(=O)(OH)$_2$, or alkaline metal salt thereof, and R$^1$ is a linear or branched C$_{1-8}$alkyl, C$_{2-8}$alkenyl, C$_{2-8}$alkynyl, C$_{1-8}$heteroalkyl, C$_{2-8}$heteroalkenyl, C$_{2-8}$heteroalkynyl, C$_{6-10}$aryl group or an amino acid residue; and
R$^3$ is selected from the group comprising a hydroxyl group or alkaline metal salt thereof, —OR$^{3A}$, a prodrug moiety, a linear or branched C$_{1-8}$alkyl, C$_{2-8}$alkenyl, C$_{2-8}$alkynyl, C$_{1-8}$heteroalkyl, C$_{2-8}$heteroalkenyl or C$_{2-8}$heteroalkynyl group, and an amine group R"HN, wherein R$^{3A}$ represents C$_{1-8}$alkyl, C$_{2-8}$alkenyl, C$_{2-8}$alkynyl, C$_{1-8}$heteroalkyl, C$_{2-8}$heteroalkenyl, C$_{2-8}$heteroalkynyl, —P(=O)(OH)$_2$ or alkaline metal salt thereof, or —P(=O)(OH)OP(=O)(OH)$_2$ or alkaline metal salt thereof, and R" is a linear or branched C$_{1-8}$alkyl, C$_{2-8}$alkenyl, C$_{2-8}$alkynyl, C$_{1-8}$heteroalkyl, C$_{2-8}$heteroalkenyl, C$_{2-8}$heteroalkynyl C$_{6-10}$aryl group or an amino acid residue.

A subclass of compounds of particular interest includes compounds of formula (I$^B$) above where X is S.

Another class of compounds of special interest includes compounds of formula (I$^C$):

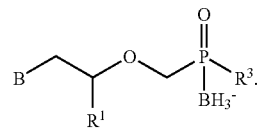

(I$^C$)

or pharmaceutically acceptable salt thereof;
wherein:
B is as defined above;
R$^1$ is selected from the group comprising a hydrogen atom, and a methyl, ethyl, hydroxymethyl, hydroxyethyl and C$_{1-8}$haloalkyl group;

$R^3$ is selected from the group comprising a hydroxyl group or alkaline metal salt thereof, —$OR^{3A}$, a prodrug moiety, and an amine group R"HN, wherein $R^{3A}$ represents $C_{1-8}$alkyl, $C_{2-8}$alkenyl, $C_{1-8}$heteroalkyl, $C_{2-8}$heteroalkenyl, $C_{2-8}$heteroalkynyl, —P(=O)(OH)$_2$ or alkaline metal salt thereof, or —P(=O)(OH)OP(=O)(OH)$_2$ or alkaline metal salt thereof, and R" is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{8-10}$aryl group or an amino acid residue.

Another class of compounds of special interest includes compounds of formula ($I^D$):

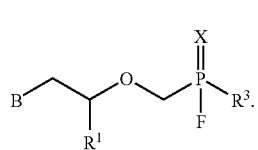

(I$^D$)

or pharmaceutically acceptable salt thereof;
wherein:
B is as defined above;
X is S, Se or O;
$R^1$ is selected from the group comprising a hydrogen atom, and a methyl, ethyl, hydroxymethyl, hydroxyethyl and $C_{1-6}$haloalkyl group;
$R^3$ is selected from the group comprising a hydroxyl group or alkaline metal salt thereof, —$OR^{3A}$, a prodrug moiety, and an amine group R"HN, wherein $R^{3A}$ represents $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, or —P(=O)(OH)OP(=O)(OH)$_2$ or alkaline metal salt thereof, and R" is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{8-10}$aryl group or an amino acid residue.

Another class of compounds of special interest includes compounds of formula ($I^E$):

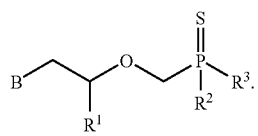

(I$^E$)

or pharmaceutically acceptable salt thereof;
wherein:
B is as defined above;
$R^1$ is selected from the group comprising a hydrogen atom, and a methyl, ethyl, hydroxymethyl, hydroxyethyl and $C_{1-6}$haloalkyl group;
$R^2$ is selected from the group comprising a hydroxyl group or alkaline metal salt thereof, —$OR^{2A}$, a prodrug moiety, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R'HN; wherein $R^{2A}$ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, —P(=O)(OH)OP(=O)(OH)$_2$, or alkaline metal salt thereof, and R' is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue;
$R^3$ is selected from the group comprising a hydroxyl group or alkaline metal salt thereof, —$OR^{3A}$, a prodrug moiety, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R"HN, wherein $R^{3A}$ represents $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, or —P(=O)(OH)OP(=O)(OH)$_2$ or alkaline metal salt thereof, and R" is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue.

Another class of compounds of special interest includes compounds of formula CO):

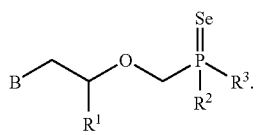

(I$^F$)

or pharmaceutically acceptable salt thereof;
wherein:
B is as defined above;
$R^1$ is selected from the group comprising a hydrogen atom, and a methyl, ethyl, hydroxymethyl, hydroxyethyl and $C_{1-6}$haloalkyl group;
$R^2$ is selected from the group comprising a hydroxyl group or alkaline metal salt thereof, —$OR^{2A}$, a prodrug moiety, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R'HN; wherein $R^{2A}$ represents $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, —P(=O)(OH)OP(=O)(OH)$_2$, or alkaline metal salt thereof, and R' is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue;
$R^3$ is selected from the group comprising a hydroxyl group or alkaline metal salt thereof, —$OR^{3A}$, a prodrug moiety, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R"HN, wherein $R^{3A}$ represents $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, or —P(=O)(OH)OP(=O)(OH)$_2$ or alkaline metal salt thereof, and R" is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{8-10}$aryl group or an amino acid residue.

Another class of compounds of special interest includes compounds of formula (e):

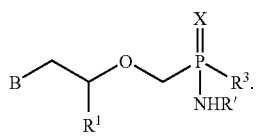

(I$^G$)

or pharmaceutically acceptable salt thereof;
wherein:
X is S or Se;
B is as defined above;
$R^1$ is selected from the group comprising a hydrogen atom, and a methyl, ethyl, hydroxymethyl, hydroxyethyl and $C_{1-6}$haloalkyl group;

R' is a linear or branched $C_{1-8}$alkyl, $C_{2-8}$alkenyl, $C_{2-8}$alkynyl, $C_{6-10}$aryl group or an amino acid residue;

$R^3$ is selected from the group comprising a hydroxyl group or alkaline metal salt thereof, —$OR^{3A}$, a prodrug moiety, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R"HN, wherein $R^{3A}$ represents $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, or —P(=O)(OH)OP(=O)(OH)$_2$ or alkaline metal salt thereof, and R" is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue.

In certain embodiments, for compounds of formulae ($I^G$) above, $R^3$ is selected from the group comprising a hydroxyl group or alkaline metal salt thereof, and —$OR^{3A}$, wherein $R^{3A}$ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, or —P(=O)(OH)OP(=O)(OH)$_2$ or alkaline metal salt thereof.

In certain embodiments, for compounds of formulae (I) and ($I^A$) through ($I^G$) above, the carbon atom bearing $R^1$ has an R configuration:

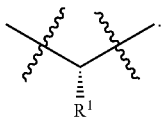

In certain embodiments, for compounds of formulae (I) and ($I^A$) through ($I^G$) above, the carbon atom bearing $R^1$ has an S configuration:

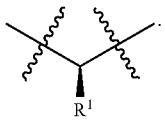

As used herein, the term "prodrug" is intended to indicate a derivative of an active compound which does not, or does not necessarily, exhibit the physiological activity of the active compound, but which may be subjected to enzymatic cleavage such as hydrolysis in vivo so as to release the active compound upon administration of the prodrug. "Prodrug moiety" refers to a radical that undergoes cleavage upon the action of an enzyme to give the active compound. For example, a prodrug moiety may be a side chain with predominantly hydrophilic properties imparting improved solubility characteristics to the prodrug, thereby making it more suitable for parenteral administration in the form of a solution or for oral administration to obtain an improved bioavailability. In certain exemplary embodiments, the prodrug moiety is bound to a phosphorus atom of the compounds mono-, bi- or tri-phosphoryl group. In the case of a bi- or tri-phosphoryl group, the prodrug moiety may be bound to the α- β- or γ-phosphorus atom. In certain exemplary embodiments, the prodrug moiety is an isopropyloxymethylcarbonyl radical having the structure —OCH$_2$OC(=O)OCH(CH$_3$)$_2$ ("POC" group), a moiety having the structure —OCH$_2$C(=O)C(CH$_3$)$_3$ (pivaloyloxymethyl or "POM" group), a moiety having the structure —OCH$_2$CH$_2$SC(=O)C(CH$_3$)$_3$ (tertiobutyl-5-acyl-2-thioethyl or "tBu-SATE" group), a moiety having the structure —OCH$_2$CH$_2$SC(=O)CH$_3$ (methyl-5-acyl-2-thioethyl or "Me-SATE" group) or a moiety having the structure —NHR' wherein R' is a linear or branched $C_{1-8}$alkyl, $C_{1-8}$heteroalkyl, $C_{6-10}$aryl group or —NHR' represents an amino acid residue.

For more information regarding enzyme-labile groups, the reader may refer to the following references:

1. Calogeropoulou T. et al. Strategies in the design of prodrugs of Anti-HIV agents. Current Topics in Medicinal Chemistry. 2003, 3, 1467-1495.
2. Starrett J. E. et al. Synthesis and in vitro evaluation of a phosphonate prodrug: bis(pivaloyloxymethyl) 9-(2-phosphonylmethoxyethyl)adenine. Antiviral Research, 19, 267-273, 1992.
3. Benzaria S. et al. Synthesis, in vitro antiviral evaluation and stability studies of Bis (S-acyl-2-thioethyl) ester derivatives of 9-(2-(phosphonomethoxy)ethyl)adenine (PMEA) as potential PMEA prodrugs with improved oral bioavailability. J med Chem. 1996, 39, 4958-4965.
4. Arimilli M N. Et al. Synthesis, in vitro biological evaluation and oral bioavailability of 9-(2-(phosphonomethoxy)propyl)adenine (PMPA) prodrugs. Antiviral Chemistry and Chemotherapy. 1997, 8(6), 557-564.
5. Meier C., *Synlett*, 233-242, 1998.
6. Perigaud C. et al., *Bioorganic & Medicinal Chemistry letters,* 3 (12), 2521-2526, 1993.
7. Wagner C. R. et al., *Bioorganic & Medicinal Chemistry Letters,* 1995, 5, 1819-1824.

The present invention encompasses any prodrug form of the compounds described herein. Although certain exemplary prodrug forms of compounds of the invention generated from the compounds phosphoryl group are detailed herein, it will be appreciated that the present invention is not intended to be limited to these prodrug moieties; rather, a variety of additional prodrug moieties can be readily identified by a person skilled in the relevant art.

Advantageously, B is a purine or pyrimidine base selected from the group comprising adenine, uracil, thymine, guanine and cytosine, and preferably B is an adenine.

Thus, in certain exemplary embodiments, compounds of interest have one of the following structures:

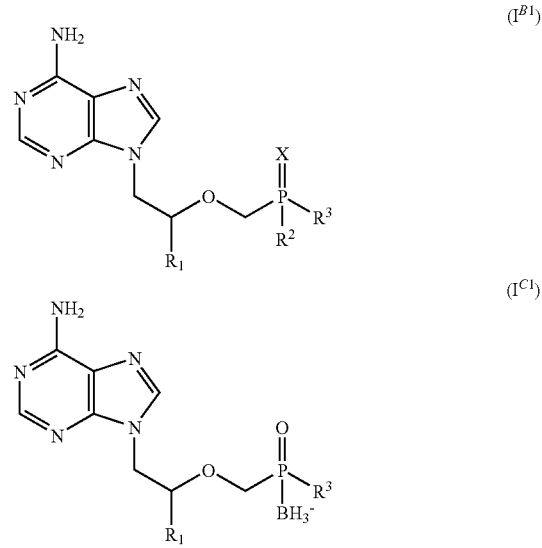

wherein X, R', R¹, R² and R³ are as defined for compound classes (e) through (I^G) above.

In certain embodiments, for compounds of formulae (I^B1) through (I^G1) above, the carbon atom bearing R¹ has an R configuration:

In certain embodiments, for compounds of formulae (I^B1) through (I^G1) above, the carbon atom bearing R¹ has an S configuration:

Advantageously, for compounds of formulae (I), (I^A)-(I^G) and (I^B1)-(I^G1), R¹ is selected from the group comprising a hydrogen atom, a methyl group, a hydroxymethyl and a $C_{1-6}$haloalkyl group. In certain embodiments, R¹ is selected from the group comprising a hydrogen atom, a methyl group, a hydroxymethyl and a $C_{1-4}$haloalkyl group. In certain embodiments, R¹ is selected from the group comprising a hydrogen atom, a methyl group, a hydroxymethyl and a halomethyl group. In certain embodiments, R¹ is selected from the group comprising a hydrogen atom, a methyl group, a hydroxymethyl and a fluoromethyl group. Advantageously, R¹ is selected from the group comprising a hydrogen atom, a methyl group and a hydroxymethyl group.

Advantageously, for compounds of formulae (I), (I^A)-(I^G) and (I^B1)-(I^G1), R² is selected from the group comprising a fluorine atom, an hydroxyl group or alkaline metal salt thereof, —OR^{2A}, a prodrug moiety, —BH₃, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, and an amine group R'HN wherein $R^{2A}$ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)₂ or alkaline metal salt thereof, —P(=O)(OH)OP(=O)(OH)₂, or alkaline metal salt thereof, and R¹ is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue. Advantageously, R² is selected from the group comprising a fluorine atom, an hydroxyl group, a linear or branched $C_{1-8}$alkyl group, and an amine group R'HN wherein R¹ is a linear or branched $C_{1-8}$alkyl group.

Advantageously, for the compounds described herein, X is a sulphur or selenium atom. In certain preferred embodiments, X is a sulphur atom.

According to a preferred embodiment, X is a sulphur atom and R² is a hydroxyl group.

According to another preferred embodiment, X is a sulphur atom and R² is an hydroxyl group or alkaline metal salt thereof, —OR^{2A}, a prodrug moiety, or an amine group R'HN, wherein $R^{2A}$ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)₂ or alkaline metal salt thereof, —P(=O)(OH)OP(=O)(OH)₂, or alkaline metal salt thereof, and R¹ is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, $C_{6-10}$aryl group or an amino acid residue.

According to another preferred embodiment, X is an oxygen atom and R² is selected from the group comprising a fluorine atom, and a BH₃ group.

Other exemplary embodiments of particular interest are illustrated by compounds of the following subgroups I through VI:

I. Compounds Having the Structure (and Pharmaceutically Acceptable Derivatives Thereof):

wherein

B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminoguanine, 2,6-diaminopurine, thymine, cytosine, uracil, 5-bromouracil, 5-iodouracil, 5-ethyluracil, 5-propyluracil, 5-vinyluracil and 5-bromovinyluracil;

R$^1$ is selected from the group comprising a hydrogen atom, and a methyl, ethyl, hydroxymethyl, hydroxyethyl and halomethyl group; and R$^{2A}$ and R$^{3A}$ are independently a hydrogen atom or an alkaline metal cation.

In certain embodiments, B is adenine and the compound has the structure:

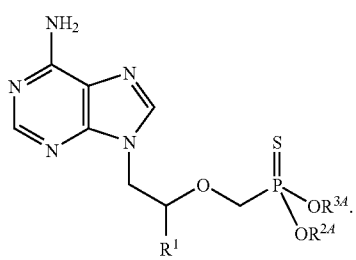

In certain embodiments, R$^1$ is hydrogen, methyl, hydroxymethyl or —CH$_2$F. In certain embodiments, R$^1$ is methyl and the carbon bearing R$^1$ is of R-configuration. In certain embodiments, R$^1$ is hydroxymethyl and the carbon bearing R$^1$ is of S-configuration. In certain embodiments, R$^1$ is —CH$_2$F and the carbon bearing R$^1$ is of R- or S-configuration. In certain embodiments, R$^{2A}$ and R$^{3A}$ are each a hydrogen atom. In certain other exemplary embodiments, R$^{2A}$ and R$^{3A}$ are each an alkaline metal cation, for example Na$^+$.

II. Compounds Having the Structure (and Pharmaceutically Acceptable Derivatives Thereof):

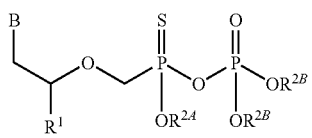

wherein

B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminoguanine, 2,6-diaminopurine, thymine, cytosine, uracil, 5-bromouracil, 5-iodouracil, 5-ethyluracil, 5-propyluracil, 5-vinyluracil and 5-bromovinyluracil;

R$^1$ is selected from the group comprising a hydrogen atom, and a methyl, ethyl, hydroxymethyl, hydroxyethyl and halomethyl group; and R$^{2A}$, R$^{2B}$ and R$^{3B}$ are independently a hydrogen atom or an alkaline metal cation.

In certain embodiments, B is adenine and the compound has the structure:

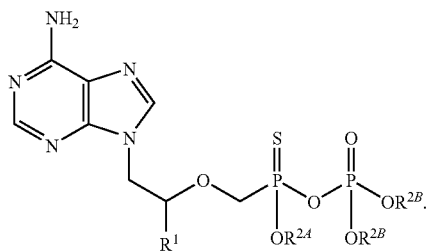

In certain embodiments, R$^1$ is hydrogen, methyl, hydroxymethyl or —CH$_2$F. In certain embodiments, R$^1$ is methyl and the carbon bearing R$^1$ is of R-configuration. In certain embodiments, R$^1$ is hydroxymethyl and the carbon bearing R$^1$ is of S-configuration. In certain embodiments, R$^1$ is —CH$_2$F and the carbon bearing R$^1$ is of R- or S-configuration. In certain embodiments, R$^{2A}$, R$^{2B}$ and R$^{3B}$ are each a hydrogen atom. In certain other exemplary embodiments, R$^{2A}$, R$^{2B}$ and R$^{3B}$ are each an alkaline metal cation, for example Na$^+$.

III. Compounds Having the Structure (and Pharmaceutically Acceptable Derivatives Thereof):

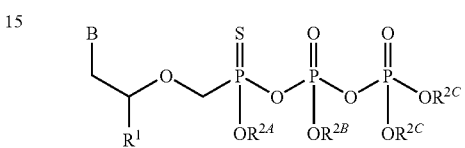

wherein

B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminoguanine, 2,6-diaminopurine, thymine, cytosine, uracil, 5-bromouracil, 5-iodouracil, 5-ethyluracil, 5-propyluracil, 5-vinyluracil and 5-bromovinyluracil;

R$^1$ is selected from the group comprising a hydrogen atom, and a methyl, ethyl, hydroxymethyl, hydroxyethyl and halomethyl group; and R$^{2A}$, R$^{2B}$, R$^{2C}$ and R$^{3C}$ are independently a hydrogen atom or an alkaline metal cation.

In certain embodiments, B is adenine and the compound has the structure:

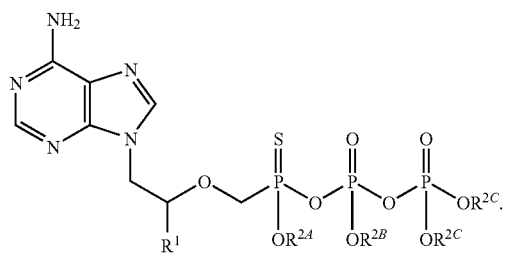

In certain embodiments, R$^1$ is hydrogen, methyl, hydroxymethyl or —CH$_2$F. In certain embodiments, R$^1$ is methyl and the carbon bearing R$^1$ is of R-configuration. In certain embodiments, R$^1$ is hydroxymethyl and the carbon bearing R$^1$ is of S-configuration. In certain embodiments, R$^1$ is —CH$_2$F and the carbon bearing R$^1$ is of R- or S-configuration. In certain embodiments, R$^{2A}$, R$^{2B}$, R$^{2C}$ and R$^{3C}$ are each a hydrogen atom. In certain other exemplary embodiments, R$^{2A}$, R$^{2B}$, R$^{2C}$ and R$^{3C}$ are each an alkaline metal cation, for example Nat.

IV. Compounds Having the Structure (and Pharmaceutically Acceptable Derivatives Thereof):

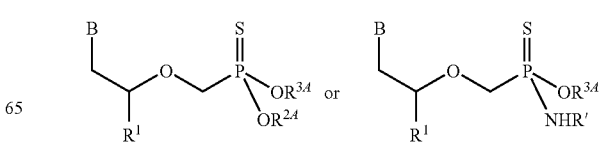

wherein

B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminoguanine, 2,6-diaminopurine, thymine, cytosine, uracil, 5-bromouracil, 5-iodouracil, 5-ethyluracil, 5-propyluracil, 5-vinyluracil and 5-bromovinyluracil;

$R^1$ is selected from the group comprising a hydrogen atom, and a methyl, ethyl, hydroxymethyl, hydroxyethyl and halomethyl group; and $R^{2A}$ is an enzyme-labile group;

R' is a linear or branched $C_{1-8}$alkyl, $C_{1-8}$heteroalkyl or $C_{6-10}$aryl group; or —NHR' represents an amino acid residue; and $R^{3A}$ is a hydrogen atom or an alkaline metal cation, for example $Na^+$.

In certain embodiments, B is adenine and the compound has the structure:

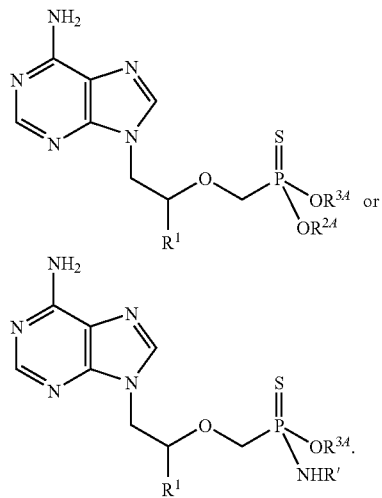

In certain embodiments, $R^1$ is hydrogen, methyl, hydroxymethyl or —$CH_2F$. In certain embodiments, $R^1$ is methyl and the carbon bearing $R^1$ is of R-configuration. In certain embodiments, $R^1$ is hydroxymethyl and the carbon bearing $R^1$ is of S-configuration. In certain embodiments, $R^1$ is —$CH_2F$ and the carbon bearing $R^1$ is of R- or S-configuration. In certain embodiments, $R^{2A}$ is —$CH_2OC(=O)OC(CH_3)_2$, —$CH_2OC(=O)C(CH_3)_3$, —$CH_2CH_2SC(=O)C(CH_3)_3$, —$CH_2CH_2SC(=O)CH_3$. In certain embodiments, —NHR' represents an α-amino acid residue selected from the group comprising alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. In certain embodiments, $R^{3A}$ is a hydrogen atom. In certain other exemplary embodiments, $R^{3A}$ is $Na^+$.

V. Compounds Having the Structure (and Pharmaceutically Acceptable Derivatives Thereof):

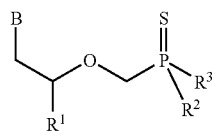

wherein

B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminoguanine, 2,6-diaminopurine, thymine, cytosine, uracil, 5-bromouracil, 5-iodouracil, 5-ethyluracil, 5-propyluracil, 5-vinyluracil and 5-bromovinyluracil;

$R^1$ is selected from the group comprising a hydrogen atom, and a methyl, ethyl, hydroxymethyl, hydroxyethyl and halomethyl group; and $R^2$ is —$OR^{2A}$ or —NHR';

$R^3$ is —$OR^{3A}$ or —NHR";

wherein $R^{2A}$ and $R^{3A}$ are independently an enzyme-labile group.

In certain embodiments, B is adenine and the compound has the structure:

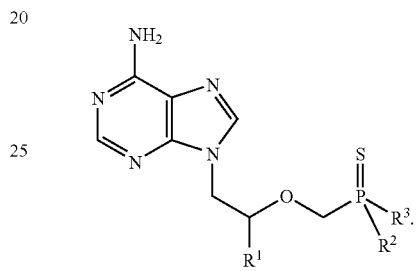

In certain embodiments, $R^1$ is hydrogen, methyl, hydroxymethyl or —$CH_2F$. In certain embodiments, $R^1$ is methyl and the carbon bearing $R^1$ is of R-configuration. In certain embodiments, $R^1$ is hydroxymethyl and the carbon bearing $R^1$ is of S-configuration. In certain embodiments, $R^1$ is —$CH_2F$ and the carbon bearing $R^1$ is of R- or S-configuration. In certain embodiments, $R^{2A}$ and $R^{3A}$ are independently —$CH_2C(=O)OCH(CH_3)_2$ ("POC" group), a moiety having the structure —$CH_2OC(=O)OC(CH_3)_2$, —$CH_2OC(=O)C(CH_3)_3$, —$CH_2CH_2SC(=O)C(CH_3)_3$ or —$CH_2CH_2SC(=O)CH_3$. In certain embodiments, —NHR' and —NHR" independently represent an α-amino acid residue selected from the group comprising alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. In certain embodiments, $R^2$ and $R^3$ are each —$OCH_2OC(=O)OC(CH_3)_2$. In certain embodiments, $R^2$ and $R^3$ are each —$OCH_2OC(=O)C(CH_3)_3$. In certain embodiments, $R^2$ and $R^3$ are each —$OCH_2CH_2SC(=O)C(CH_3)_3$. In certain embodiments, $R^2$ and $R^3$ are each —$OCH_2CH_2SC(=O)CH_3$. In certain embodiments, $R^2$ and $R^3$ are each an α-amino acid residue selected from the group comprising alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

VI. Compounds Having the Structure (and Pharmaceutically Acceptable Derivatives Thereof):

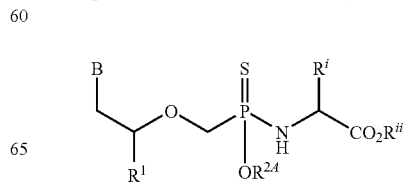

wherein

B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminoguanine, 2,6-diaminopurine, thymine, cytosine, uracil, 5-bromouracil, 5-iodouracil, 5-ethyluracil, 5-propyluracil, 5-vinyluracil and 5-bromovinyluracil;

$R^1$ is selected from the group comprising a hydrogen atom, and a methyl, ethyl, hydroxymethyl, hydroxyethyl and halomethyl group; and $R^{2A}$ is a hydrogen atom, an alkaline metal cation or $C_{1-8}$alkyl;

$R^i$ is a hydrogen atom or an amino acid side chain; and $R^{ii}$ is a hydrogen atom, an alkaline metal cation or $C_{1-8}$alkyl.

In certain embodiments, B is adenine and the compound has the structure:

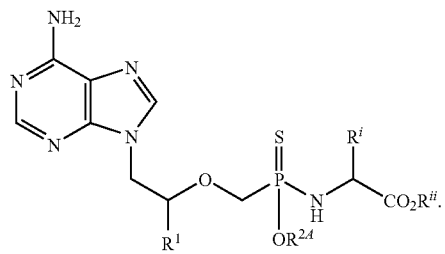

In certain embodiments, $R^1$ is hydrogen, methyl, hydroxymethyl or —$CH_2F$. In certain embodiments, $R^1$ is methyl and the carbon bearing $R^1$ is of R-configuration. In certain embodiments, $R^1$ is hydroxymethyl and the carbon bearing $R^1$ is of S-configuration. In certain embodiments, $R^1$ is —$CH_2F$ and the carbon bearing $R^1$ is of R- or S-configuration. In certain embodiments, $R^{2A}$ is a hydrogen atom, $Na^+$ or $C_{1-8}$alkyl. In certain embodiments, $R^i$ is the side chain of one of the following amino acids: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine. In certain embodiments, $R^i$ is hydrogen atom, $Na^+$ or methyl.

In certain embodiments, for compounds of formulae (I), ($I^A$)-($I^G$) and ($I^{B1}$)-($I^{G1}$), and compounds of subgroups I through VI above, $R^1$ is methyl or ethyl and the carbon atom bearing $R^1$ has an R-configuration.

In certain embodiments, for compounds of formulae (I), ($I^A$)-($I^G$) and ($I^{B1}$)-($I^{G1}$), and compounds of subgroups I through VI above, $R^1$ is hydroxymethyl or hydroxyethyl and the carbon atom bearing $R^1$ has an S-configuration.

In certain embodiments, for compounds of formulae (I), ($I^A$)-($I^G$) and ($I^{B1}$)-($I^{G1}$), and compounds of subgroups I through VI above, $R^1$ is a $C_{1-6}$haloalkyl group, preferably a halomethyl group, more preferably —$CH_2F$, and the carbon atom bearing $R^1$ has an R- or S-configuration.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

As used herein, the term "alkyl" refers to a saturated aliphatic hydrocarbon including straight chain and branched chain groups. An analogous convention applies to other generic terms such as "alkenyl", "alkynyl" and the like. Furthermore, as used herein, unless specified otherwise, the terms "alkyl", "alkenyl", "alkynyl" and the like encompass unsubstituted groups.

In certain embodiments, the alkyl groups employed in the invention contain about 1-20 aliphatic carbon atoms. In certain other embodiments, the alkyl groups employed in the invention contain about 1-10 aliphatic carbon atoms. In yet other embodiments, the alkyl groups employed in the invention contain about 1-8 aliphatic carbon atoms. In still other embodiments, the alkyl groups employed in the invention contain about 1-6 aliphatic carbon atoms. In yet other embodiments, the alkyl groups employed in the invention contain about 1-4 carbon atoms. Illustrative alkyl groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like.

In certain embodiments, the alkenyl and alkynyl groups employed in the invention contain about 2-20 aliphatic carbon atoms. In certain other embodiments, the alkenyl, and alkynyl groups employed in the invention contain about 2-10 aliphatic carbon atoms. In yet other embodiments, the alkenyl, and alkynyl groups employed in the invention contain about 2-8 aliphatic carbon atoms. In still other embodiments, the alkenyl, and alkynyl groups employed in the invention contain about 2-6 aliphatic carbon atoms. In yet other embodiments, the alkenyl, and alkynyl groups employed in the invention contain about 2-4 carbon atoms. Illustrative alkenyl groups include, but are not limited to, for example, ethenyl, propenyl, butenyl, 1-methyl-2-buten-1-yl, and the like. Illustrative alkynyl groups include, but are not limited to, ethynyl, 2-propynyl (propargyl), 1-propynyl and the like.

A heteroalkyl group, as used herein, refers to an alkyl group wherein at least one carbon atom has been replaced with a heteroatom such as an oxygen, sulfur, nitrogen or silicon atom. The terms "heteroalkenyl" and "heteroalkynyl" are defined in a similar fashion, wherein "alkyl" in the definition above is replaced by "alkenyl" and "alkynyl" respectively.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

The term "halo" as used herein refers to an atom selected from fluorine, chlorine, bromine and iodine.

The term "haloalkyl" denotes an alkyl group, as defined above, having one, two, or three halogen atoms attached thereto and is exemplified by such groups as chloromethyl, fluoromethyl, bromoethyl, trifluoromethyl, and the like.

2) Synthetic Overview:

The practitioner has a well-established literature of nucleotide and phosphorus chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates. Certain cited patent documents also contain information on formulation, uses, and administration of such compounds which may be of interest. For example, guidance may be found in WO 2006/114064, WO 2004/111064, WO 03/002580, EP 0 253 412, EP 0 206 459 and/or EP 0 205 826.

Moreover, the practitioner is directed to the specific guidance and examples provided in this document relating to various exemplary compounds and intermediates thereof.

As described above, the present invention provides novel compounds, specifically compounds having the following general structure:

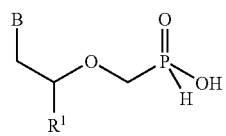

(I)

and pharmaceutically acceptable salt thereof;

wherein B, X and $R^1$-$R^3$ are as defined in classes and subclasses herein.

It will be appreciated that for compounds as generally described above, certain classes of compounds are of special interest. For example, one class of compounds of special interest includes adenine derivatives having the Formula (I'):

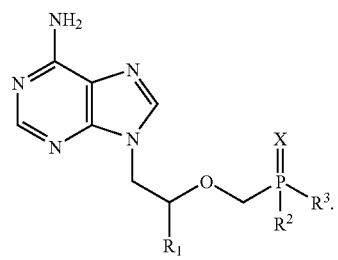

(I')

Compounds of the invention can be conveniently prepared starting from a H-phosphinate intermediate having the structure:

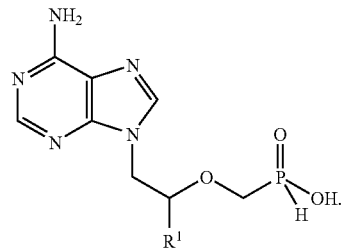

wherein B and $R^1$ are as defined in classes and subclasses herein.

In certain embodiments, B is adenine and the intermediate has the structure:

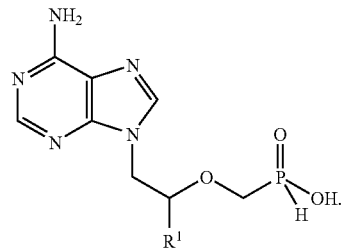

An exemplary synthetic approach for preparing boranophosphonate, selenophosphonate and thiophosphanate derivatives is depicted in Scheme A below:

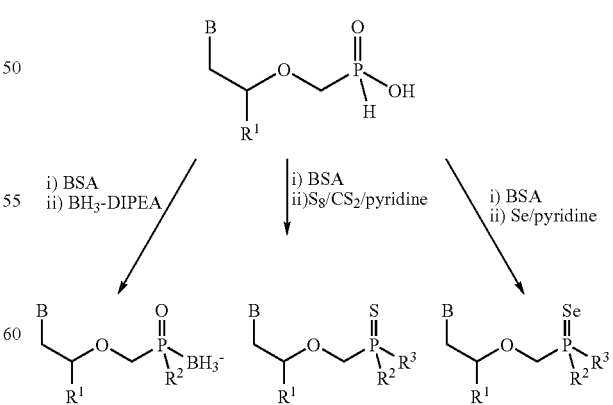

An exemplary synthetic approach for preparing fluorophosphonate, aminophosphonate and aryl/alkylphosphonate derivatives is depicted in Scheme B below:

Scheme B

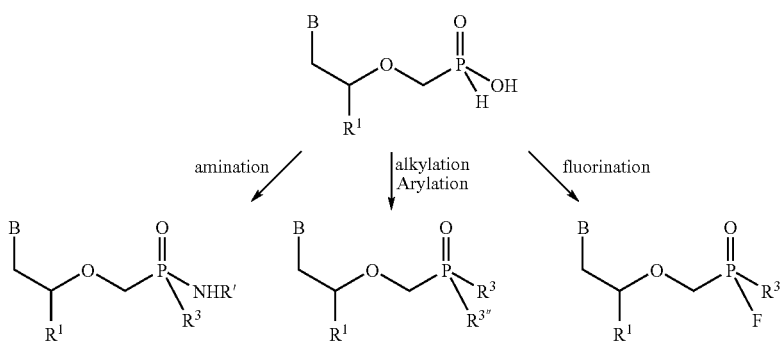

wherein B, R', $R^1$ and $R^3$ are as defined in classes and subclasses herein, and R" is a $C_{1-8}$alkyl or $C_{6-10}$aryl moiety.

As discussed above, compounds of the invention can be prepared from an H-phosphinate precursor intermediate according to the exemplary synthetic pathways depicted in Schemes A and B, and further illustrated in the examples. In fact, the inventors have demonstrated that compounds of the invention can be obtained in high yield from an H-phosphinate precursor intermediate.

Thus, in another aspect of the invention, there is provided an H-phosphinate precursor intermediate of formula (II) useful for preparing compounds of the invention:

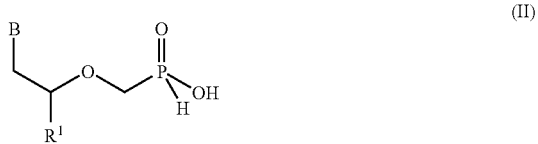

(II)

wherein:
B is a purine or pyrimidine base selected from the group comprising adenine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, cytosine, uracil, 5-bromouracil, 5-iodouracil, 5-ethyluracil, 5-propyluracil, 5-vinyluracil and 5-bromovinyluracil; and $R_1$ is selected from the group comprising a hydrogen atom, methyl, ethyl, hydroxymethyl, hydroxyethyl and $C_{1-6}$haloalkyl groups.

It is understood that the invention is not limited to this one particular synthetic pathway, and extends to other methods leading to the preparation of compounds of the invention without using the intermediate of formula (II).

In summary, the inventors have developed a synthetic method making it possible to obtain novel phosphonate analogues. In addition, the inventors have demonstrated that some of these analogues presented an effectiveness comparable or better to certain known analogues but with lower cytotoxicity. Finally, the inventors have also demonstrated that the mutant K65R Reverse Transcriptase (RT) was not resistant to some of these analogues.

Exemplary compounds of the invention are listed in the Table below:

| N° | Compound name | Compound structure | Abbreviated name |
|---|---|---|---|
| 6a | 9-[2-(Boranophosphono-methoxy)ethyl]adenine | 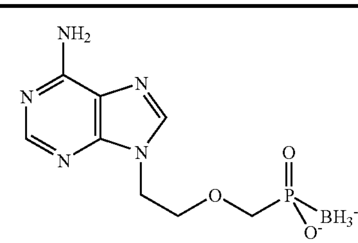 | $BH_3$-PMEA |
| 6b | (R)-9-[2-(Boranophosphono-methoxy)propyl]adenine | 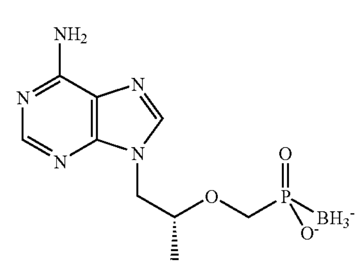 | $BH_3$-PMPA |

| N° | Compound name | Compound structure | Abbreviated name |
|---|---|---|---|
| 6 | 9-[2-(thiophosphono-methoxy)ethyl]adenine | 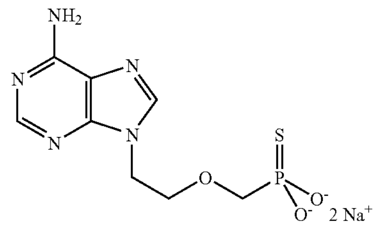 | S-PMEA |
| 11 | (R)-9-[2-(Thiophosphono-methoxy)propyl]adenine | 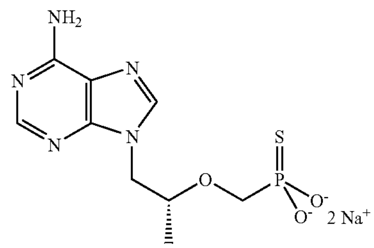 | S-PMPA |
| 12 | 9-[2-(Diphosphorylthio-phosphonomethoxy)ethyl]adenine | 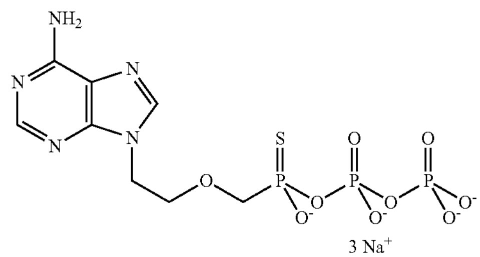 | S-PMEApp |
| 13 | (R)-9-[2-(Pyrophosphoroxythio-phosphonomethoxy)propyl]adenine | 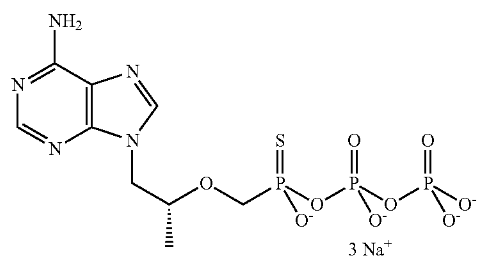 | S-PMPApp |
| 14 | 9-[2-(thiophosphono-methoxy)ethyl]adenine, mono isopropyloxycarbonyl oxy méthyle ester | 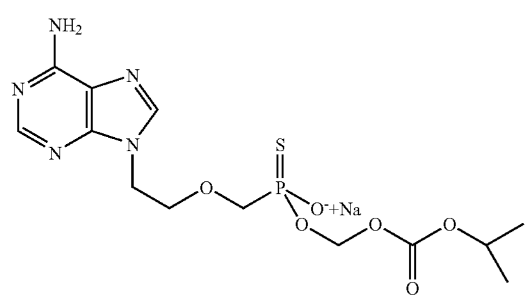 | Mono-POC S-PMEA |

-continued

| N° | Compound name | Compound structure | Abbreviated name |
|---|---|---|---|
| 15 | 9-[2-(thiophosphono-methoxy)ethyl]adenine, bis isopropyloxycarbonyl oxy methyl ester | 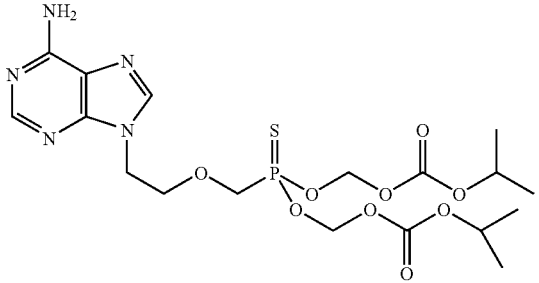 [SMILES: CC(C)OC(=O)OCOP(=S)(COCCn1cnc2c(N)ncnc21)OCOC(=O)OC(C)C] | Bis-POC S-PMEA |
| 16 | (R)-9-[2-(thiophosphono-methoxy)propyl]adenine, mono isopropyloxycarbonyl oxy methyl ester | 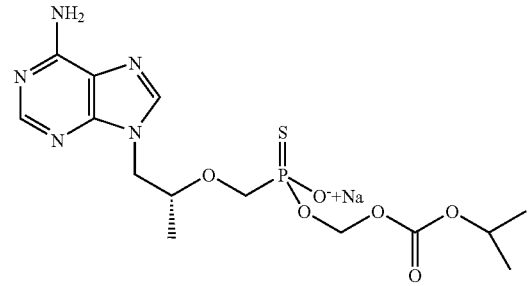 | Mono-POC S-PMPA |
| 17 | (R)-9-[2-(thiophosphono-methoxy)propyl]adenine, bis isopropyloxycarbonyl oxy methyl ester | 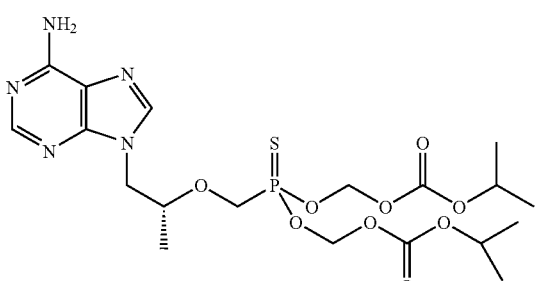 | Bis-POC S-PMPA |

For the sake of simplification, compounds 6a, 6b and 6-17 may be referred to herein using the abbreviated names provided in the above Table.

3) Pharmaceutical Compositions

As discussed above, the present invention provides antiviral compounds, and thus the present compounds are useful for the treatment of diseases, disorders, and conditions including, but not limited to HIV infection, Hepatitis B and HSV. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

Thus, in another aspect of the invention, there is provided pharmaceutical compositions comprising a purine or pyrimidine phosphonate derivative of formula (I) as previously described in classes and subclasses herein or pharmaceutically acceptable salts thereof.

Advantageously, B is a purine or pyrimidine base selected from the group comprising adenine, uracil, thymine, guanine and cytosine, and B is preferably adenine.

Advantageously, $R^1$ is selected from the group comprising a hydrogen atom, a methyl group, a hydroxymethyl and a $C_{1-6}$haloalkyl group. In certain embodiments, $R^1$ is selected from the group comprising a hydrogen atom, a methyl group, a hydroxymethyl and a $C_{1-4}$haloalkyl group. In certain embodiments, $R^1$ is selected from the group comprising a hydrogen atom, a methyl, ethyl, hydroxymethyl, hydroxyethyl and a halomethyl group. In certain embodiments, $R^1$ is selected from the group comprising a hydrogen atom, a methyl group, a hydroxymethyl and a fluoromethyl group. Advantageously, $R^1$ is selected from the group comprising a hydrogen atom, a methyl group and a hydroxymethyl group.

Advantageously, $R^2$ is selected from the group comprising a fluorine atom, an hydroxyl group or alkaline metal salt thereof, —$OR^{2A}$, a prodrug moiety, —$BH_3$, a linear or branched $C_{1-8}$alkyl, $C_{2-8}$alkenyl or $C_{2-8}$alkynyl group, and an amine group R'HN wherein $R^{2A}$ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, —P(=O)(OH)OP(=O)(OH)$_2$, or alkaline metal salt thereof, and R' is a linear or branched $C_{1-8}$alkyl, $C_{2-8}$alkenyl, $C_{2-8}$alkynyl, $C_{6-10}$aryl group or an amino acid residue. Advantageously, $R^2$ is selected from the group comprising a fluorine atom, an hydroxyl group, —$BH_3$, a linear or branched $C_{1-8}$alkyl group, and an amine group R'HN wherein $R^1$ is a linear or branched $C_{1-8}$alkyl group.

Advantageously, X is a sulphur or selenium atom. In certain preferred embodiments, X is a sulphur atom.

According to a preferred embodiment, X is a sulphur atom and $R^2$ is a hydroxyl group.

According to another preferred embodiment, X is a sulphur atom and $R^2$ is an hydroxyl group or alkaline metal salt thereof, —$OR^{2A}$, or a prodrug moiety, wherein $R^{2A}$ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, —P(=O)(OH)OP(=O)(OH)$_2$, or alkaline metal salt thereof.

According to yet another preferred embodiment, X is an oxygen atom and $R^2$ is selected from the group comprising a fluorine atom and a $BH_3$ group.

It will also be appreciated that certain compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an active metabolite or residue thereof. As used herein, the term "active metabolite or residue thereof" means that a metabolite or residue thereof also exhibit antiviral properties.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

Research Uses

According to the present invention, the inventive compounds may be assayed in any of the available assays known in the art for identifying compounds having antiviral activity. For example, the assay may be cellular or non-cellular, in vivo or in vitro, high- or low-throughput format, etc.

In certain exemplary embodiments, compounds of this invention were assayed for their ability to inhibit DNA or RNA viral polymerase, more particularly HIV-1, HIV-2, HSV or HBV reverse transcriptase.

Thus, in one aspect, compounds of this invention which are of particular interest include those which:

exhibit the ability to inhibit a DNA or RNA viral polymerase;

inhibit HIV-1 or HIV-2 reverse transcriptase;
inhibit HSV polymerase;
inhibit HBV reverse transcriptase;
are useful for treating mammals (e.g., humans) or animals suffering from a viral polymerase-mediated disease or condition, and for helping to prevent or delay the onset of such a disease/condition;
exhibit a favorable therapeutic profile (e.g., safety, efficacy, and stability).

In yet another aspect of the invention, there is provided the use of a therapeutic composition as previously described for the preparation of a medication for treating and/or preventing a viral infection in a patient.

By viral infection, infection by a DNA or RNA virus is meant. By way of example of a DNA virus, we may mention the families of the Hepadnaviridae (HBV), the Herpesviridae (CMV, EBV, VZV, HHV-6, HPV, HSV-1 and HSV-2) and the Poxyiridae (vaccinia). By way of example of an RNA virus, we may mention the viruses of the families of the Bunyaviruses (punto toro), the Flaviviridae (HCV), the Orthomyxoviridae, the Paramyxoviridae (parainfluenza and RSV), the Picornaviridae (Coxsackie B4), the Retroviridae (SIV, FIV, HTLV, FeLV, HIV-1 and HIV-2), the Togaviridae (Sindbis). Other families include the arenaviridae, coronaviridae, arteriviridae, reoviridae and bornaviridae.

In certain embodiments, compounds of the invention are HIV-1 reverse transcriptase inhibitors. In certain other embodiments, compounds of the invention are HBV reverse transcriptase inhibitors.

In yet another aspect, a method for the treatment or lessening the severity of a viral infection is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a viral infection.

The formulation of the pharmaceutical compositions according to the invention is of the type generally used in the pharmaceutical field.

By way of example, this may involve pharmaceutical vectors such as, for example, salts or electrolytes, salts of ascorbic acid, water or buffered solutions, colloidal solutions, cellulose-based substances, polyethylene glycol, polyacrylates, waxes, proteins, or any other substance capable of dissolving or making the active compound available for therapeutic action. The compositions of this invention can be administered in injectable form or by the oral, parenteral, nasal in spray form, rectal or vaginal route, by reservoir or dispensers implantation or in any other galenic form in use in the pharmaceutical field.

The compounds and compositions, according to the method of the present invention, may be administered using any amount and any route of administration effective for treating or lessening the severity of a viral infection. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of DNA or RNA viral polymerase. In one embodiment, the compounds and compositions of the invention are DNA or RNA viral polymerase inhibitors (for example, HIV-1, HIV-2, HSV and/or HBV reverse transcriptase inhibitors), and thus, without wishing to be bound by any particular theory, the compounds and compositions are particularly useful for treating or lessening the severity of a disease, condition, or disorder where activation of a DNA or RNA viral polymerase is implicated in the disease, condition, or disorder. When activation of a DNA or RNA viral polymerase is implicated in a particular disease, condition, or disorder, the disease, condition, or disorder may also be referred to as "a viral polymerase-mediated disease" or disease symptom or more generally <<viral infection>>. Accordingly, in another aspect, the present invention provides a method for treating or lessening the severity of a disease, condition, or disorder where activation of a DNA or RNA viral polymerase is implicated in the disease state.

The term "viral polymerase-mediated disease", "viral polymerase-mediated condition" or <<viral infection>>, as used herein, means any disease or other deleterious condition in which a DNA or RNA viral polymerase is known to play a role. The terms "viral polymerase-mediated disease", "viral polymerase-mediated condition" or <<viral infection>> also mean those diseases or conditions that are alleviated by treatment with a viral polymerase inhibitor. The term "viral polymerase-mediated disease", as used herein, means any disease or other deleterious condition or disease in which a DNA or RNA viral polymerase is known to play a role. Such diseases or conditions include, without limitation, the families of the Hepadnaviridae (HBV), the Herpesviridae (CMV, EBV, VZV, HHV-6, HPV, HSV-1 and HSV-2), the Poxyiridae (vaccinia), the Bunyaviruses (punto toro), the Flaviviridae (HCV), the Orthomyxoviridae, the Paramyxoviridae (parainfluenza 3 and RSV), the Picornaviridae (Coxsackie B4), the Retroviridae (SIV, FIV, HTLV, FeLV, HIV-1 and HIV-2), the Togaviridae (Sindbis). Other families include the arenaviridae, coronaviridae, arteriviridae, reoviridae and bornaviridae.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, other therapies, chemotherapeutic agents or other antiviral agents may be combined with the compounds of this invention to treat viral infections. Examples of therapies or antiviral agents that may be used in combination with the inventive antiviral agents of the present invention include surgery, radiotherapy, hyperthermia and cryotherapy, agents to attenuate any adverse effects (e.g., antiemetics), and other approved antiviral drugs, including, but not limited to, the NRTIs, 3'-azido-3'-deoxythymidine (zidovudine, AZT), 2'-deoxy-3'-thiacytidine (3TC, lamivudine), 2',3'-dideoxy-2', 3'-didehydrothymidine (d4T, stavudine), carbovir (carbocyclic 2',3'-dideoxy-2',3'-didehydroguanosine), abacavir (ABC), 2',3'-dideoxyinosine (ddI, didanosine), 2',3'-dideoxycytidine (ddC, zalcitabine), other non-nucleoside reverse transcriptase inhibitors: nevirapine, delaviridine, efavirens, daparivine, etc.), protease inhibitors: saquinavir, indinavir, ritonovir, amprenavir, nelfinavir, lopinavir, acyclic nucleosides such as acyclovir, valacyclovir, penciclovir, famciclovir, ganciclovir, other antivirals including ribavirin, 2-thio-6-azauridine, tubercidin, aurintricarboxylic acid, 3-deazaneoplanocin, neoplanocin, rimantidine, adamantine, foscarnet, brivudin, trifluridine. For a more comprehensive discussion of updated antiviral therapies see, The Merck Manual, Seventeenth Ed. 1999, the entire contents of which are hereby incorporated by reference. See also the Food and Drug Administration (FDA) website for a list of the FDA approved antiviral drugs (www.fda.gov/cder/antivirals—See Appendix).

Another aspect of the invention relates to inhibiting viral reverse transcriptase activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of viral polymerase activity in a biological sample is useful for a variety of purposes that are known to one of skill in the art. Examples of such purposes include, but are not limited to, blood transfusion, organ-transplantation, biological specimen storage, and biological assays.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

The examples which follow are provided by way of illustration and do not limit the scope of this invention.

General Methods

Melting points were determined in capillary tubes with a 9100 Electrothermal (Fisher Scientific) apparatus and are uncorrected. The $^1$H NMR, $^{13}$C NMR and $^{31}$P NMR spectra were determined with a BRUKER AMX 250 MHz and the $^{11}$B NMR spectrum was determined with a BRUKER AMX 400 MHz. Chemical shifts are expressed in ppm and coupling constants (J) are in hertz (s=singlet, bs=broad singulet, d=doublet, dd=double doublet, t=triplet, dt=double triplet, td=triple doublet, qd=quadruple doublet, m=multiplet, dm=double multiplet, sept=septuplet).

FAB Mass Spectra and High Resolution Mass Spectra (HRMS) were obtained on a JEOL SX 102 mass spectrometer using a cesium ion source and a glycerol/thioglycerol matrix. Preparative flash column chromatographies were performed using silica gel (Merck) G60 230-240 mesh. Analytical thin layer chromatographies were performed on silica gel 60F 254 aluminium plates (Merck) of 0.2 mm thickness. The spots were examined with UV light and Cericdip Sray. HPLC was performed on a Waters 600E controller system equipped with a 991 photodiode array detector (detection 260 nm), auto-injector 717 and on-line degazer. Samples were eluted at a flow rate of 1 mL/min using a linear gradient 0-100% B in 60 min. Stability studies were performed on a column Nova-pak C18 (4 µM, 3.9×150 mm)+a precolumn Nova-pak C18 (4 µM, 3.9×150 mm) with a on-line filtration system. Analytical reverse phase (RP) chromatography was carried out on a 4.6×100 mm Source®15RPC column or a column X-Terra MS $C_{18}$ (5 µM, 4.6×250 mm)+precolumn X-Terra MS $C_{18}$ (3.5 µM, 3.9×20 mm). Large-scale purification of derivatives was achieved on an ÄKTAprime FPLC (Amersham) using a Source™ 30RPC column (18×350 mm) and a linear gradient 0-100% B or a DEAE-Sephadex column (ion exchange). Medium-scale purification of derivatives was achieved on HPLC using column X-terra prep MS $C_{18}$ (10 µM, 10×250 mm)+precolumn X-Terra prep MS $C_{18}$ (10 µM, 10×10 mm) with a flow rate of 4.5 mL/min using a linear gradient 0-100% B in 45 min. Eluant A: 0.05 M triethylammonium bicarbonate buffer (pH 7.5); eluant B: solution A containing 50% of acetonitrile. A stock solution of triethylammonium bicarbonate buffer TEAB (pH 7.5) 1M was prepared by addition of dry-ice in a 1M triethylamine solution in water to reach pH 7.5 and filtered with membrane 0.22 µM GV-type (Millipore). HPLC and MPLC buffers were prepared daily.

Synthetic Overview:

An original synthetic method has been developed which uses an H-phosphinate precursor intermediate molecule. This intermediate allowed the synthesis of various classes of compounds of the invention, as depicted in Scheme 1:

α-boranophosphonates
thiophosphonates
selenophosphonates

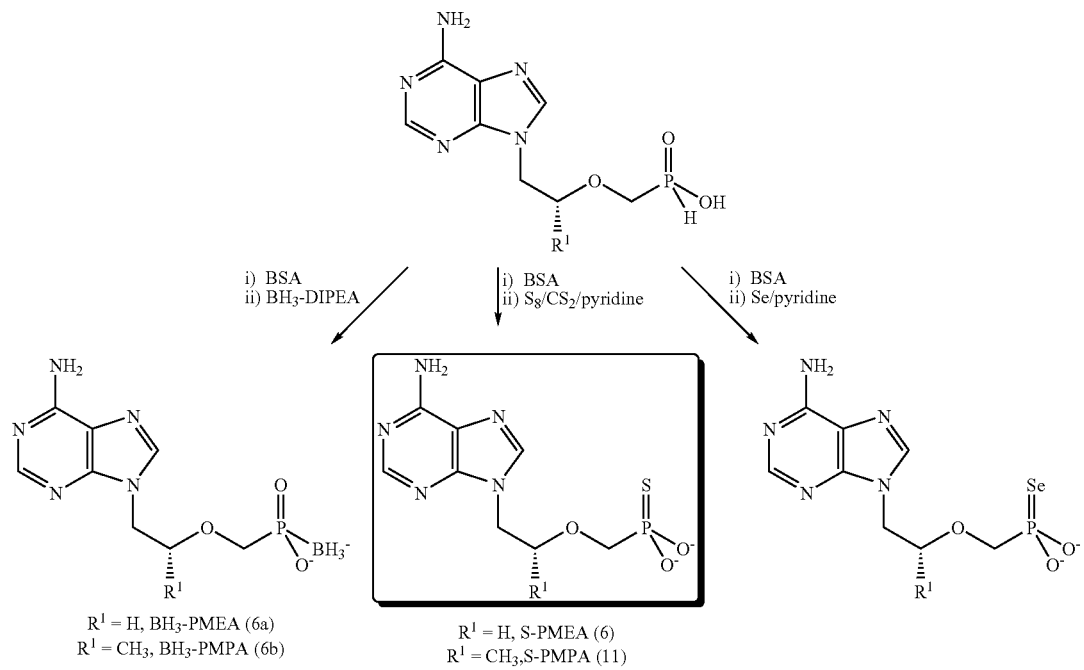

As shown in scheme 1, oxidation of the precursor intermediate H-phosphinate by a boron complex leads to a borano-phosphonate. Oxidation of the H-phosphinate precursor by selenium leads to a selenophosphonate. Finally, oxidation of the H-phosphinate precursor by sulphur leads to a thiophos-phonate.

This methodology may be applied to the synthesis of fluorophosphonate, aminophosphonate and aryl/alkylphospho-nate derivatives as described in scheme 2.

Moreover, this methodology may be applied by modulating the nature of the R group and the base in order to increase the therapeutic arsenal and to broaden the action of these compounds to viral targets other than those described in this document.

Scheme 2
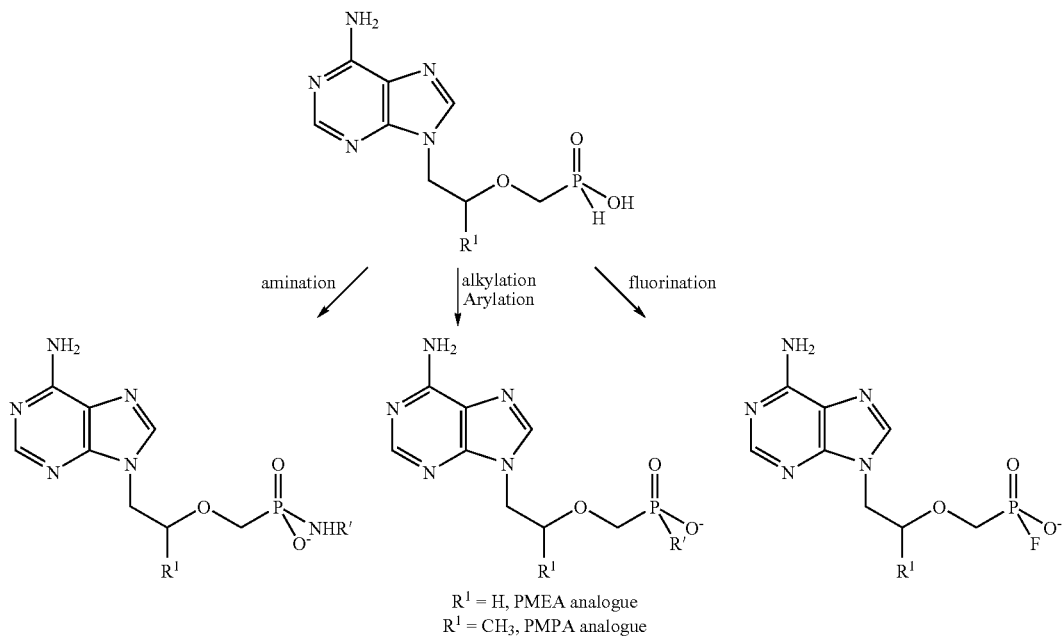
R¹ = H, PMEA analogue
R¹ = CH₃, PMPA analogue
Example 1
Synthesis of 9-[2-(hydroxyphosphinylmethoxy)ethyl]adenine (5) and (R)-9-[2-(hydroxyphosphinylmethoxy)propyl]adenine (10)
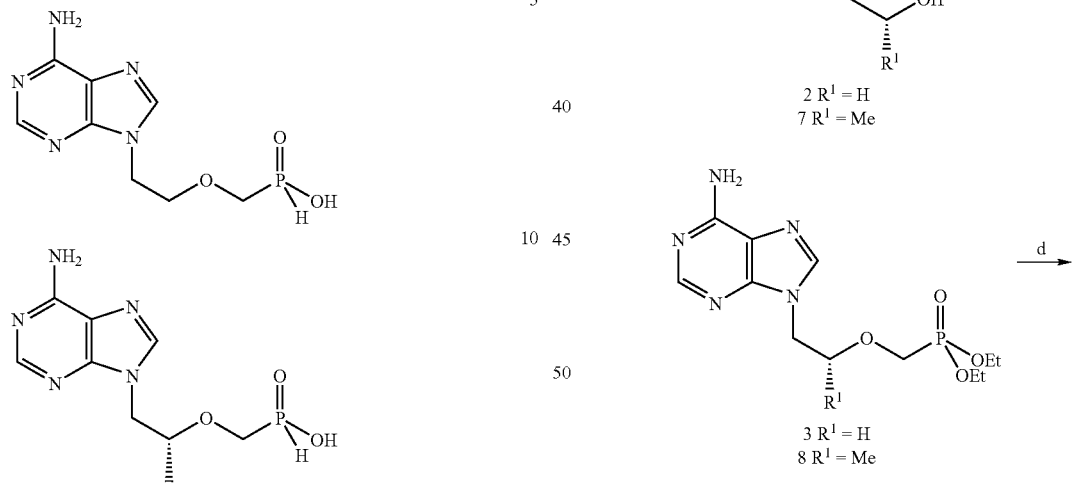
Compounds 5 and 10 may be prepared according to the synthetic pathway depicted in Scheme 3 below.
Scheme 3

-continued

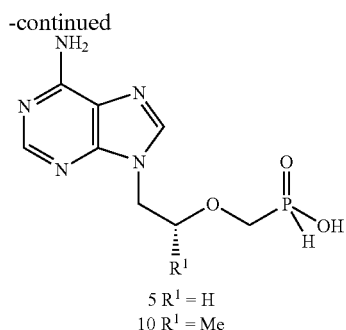

5 R¹ = H
10 R¹ = Me

Reagents and conditions: (a) 2-bromoethylbenzoate, NaH, DMF, 60° C., 16 hr. then saturated NH₃/MeOH 14 hr.; (b) (R)-propylene carbonate, NaOH, DMF, 140° C., 16 hr.; (c) diethyl[[(p-toluenesulfonyl)oxy]methyl]-phosphonate (A), sodium tert-butanolate, DMF, ambient temperature, 72 hr.; (d) TMSCl, LiAlH₄, THF, −78° C. then ambient temperature 2 hr.; (e) H₂O₂, H₂O/THF, ambient temperature 1 hr.

The reaction of adenine and 2-bromoethylbenzoate in the presence of NaH in DMF at 60° C., followed by cleavage of the benzoate protecting group in MeOH saturated with ammonia, gave compound 2 with a yield of 84%. Condensation of adenine with (R)-propylene carbonate in DMF at 140° C. for 16 hours in the presence of sodium hydroxide in catalytic quantity lead to pure alcohol 7 directly isolated by crystallization from the reaction mixture with a yield of 81%. The resulting alcohols 2 and 7 were alkylated with diethyl[[(p-toluenesulfonyl)oxy]methyl]phosphonate A in the presence of sodium tert-butanolate in DMF, which lead to diethylphosphonates 3 and 8 with yields of 27% and 29%, respectively.

The LiAlH$_a$ step for the reduction of the two phosphonate diesters 3 and 8 in THF by addition of a stoichiometric quantity of TMSCl lead to the formation of phosphines 4 and 9 with a yield of 78% and 65% respectively. Phosphines 4 and 9 were then isolated, purified and characterized.

The phosphines were then oxidized with two equivalents of hydrogen peroxide in a water/THF mixture to obtain the H-phosphinates 5 and 10 with a quantitative yield. The course of the reaction was monitored by ³¹P NMR spectroscopy. The oxidation of compounds 4 and 9 turned out to be rapid and the reaction was complete after 1 hour. Study of the ³¹P NMR spectra established that the signals for 4 (™: −144.67 ppm, tt, $_1J_{PH}$=199.0 Hz and $_2J_{PH}$=7.8 Hz) and 9 (™: −144.86 ppm, tt, $_1J_{PH}$=198.5 Hz and $_2J_{PH}$=7.3 Hz) were replaced by new resonances at 21.15 ppm for 5 (dm, $_1J_{PH}$=528 Hz) and 24.64 ppm for 10 (dm, $_1J_{PH}$=528 Hz).

Compound 2: 9-(2-hydroxyethyl)adenine

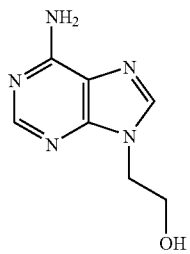

2

To a suspension of 60% NaH in mineral oil (1.70 g, 42.57 mmol) in anhydrous DMF (120 mL) was added adenine (5.23 g, 38.70 mmol) under argon, and the mixture was heated at 60° C. for 1 h. 2-Bromoethylbenzoate (9.2 mL, 58.06 mmol) was added dropwise at 60° C., and the reaction was stirred at this temperature for 16 h. The mixture was then filtered to remove insoluble materiel, the filtrate was evaporated under reduced pressure and co-evaporated three times with toluene. The residue was triturated with EtOAc then filtered to give a white solid, which was immediately resuspended in a saturated ammonia solution in MeOH (400 mL). The reaction mixture was stirred for 14 h at room temperature, and then methanol was removed under reduced pressure. Recrystallization from EtOH afforded compound 2 (5.87 g, 85%): mp 236° C. (Lit. 238-239° C.); ¹H NMR (DMSO-d6): 8.13 (s, 1H, H-2), 8.10 (s, 1H, H-8), 7.23 (bs, 2H, NH₂), 5.05 (bs, 1H, OH), 4.19 (t, J=5.2 Hz, 2H, CH₂O), 3.71 (t, J=5.2 Hz, 2H, CH₂N). ¹³C NMR (DMSO-d6) δ: 155.79, 152.23, 149.44, 141.46, 118.55, 59.17, 45.61. MS (GT, FAB⁺): 136 (B+1H)⁺, 180 (M+1H)⁺, 202 (M+Na)⁺.

Compound A:
diethyl[[(p-toluenesulfonyl)oxy]methyl]phosphonate

Triethylamine (3.38 mL, 24.04 mmol) was added dropwise to a stirred solution of diethyl hydroxymethylphosphonate (3.85 g, 24.04 mmol) in dry Et₂O (30 mL). After the mixture had cooled to −10° C., a solution of toluene-p-sulfonyl (4.58 g, 24.04 mmol) in dry Et₂O (10 mL) was added dropwise with the internal temperature maintained at −10° C. After being stirred at 0° C. for 1 h, the mixture was allowed to warm to room temperature and was then stirred for 16 h. Et₂O (80 mL) was added and the solid was filtered off. The solvents were removed under reduced pressure and the oil was purified by flash chromatography (dichloromethane/AcOEt: 9/1) to afford the compound A (5.57 g, 75%) as an colourless oil. ¹H NMR (CDCl₃) δ: 7.76 (d, J=8.1 Hz, 2H, Ts), 7.33 (d, J=8.1 Hz, 2H, Ts), 4.15 (m, 6H, CH₂ from P(OEt)₂ and CH₂P), 2.40 (s, 3H, Ts), 1.28 (t, J=6.9 Hz, 6H, CH₃ from P(OEt)₂). ¹³C NMR (CDCl₃) δ: 145.91, 132.05, 130.38, 128.53, 63.75 (d, J=6.6 Hz), 62.76 (d, $J_{CP}$=168.8 Hz), 21.99, 16.69 (d, J=5.5 Hz). MS (GT, FAB⁺): 155 (Ts)⁺, 267 (M−2Et)⁺, 295 (M−Et)⁺, 323 (M+1H)⁺, 645 (2M+1H)⁺.

Compound 3:
9-[2-(diethylphosphonomethoxy)ethyl]adenine

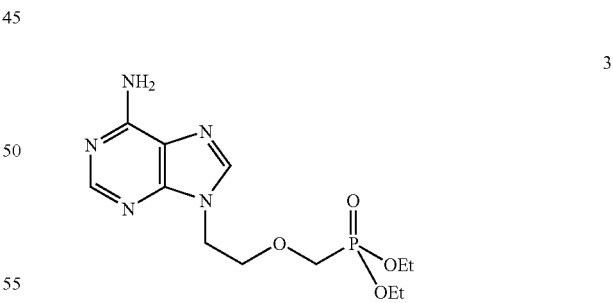

3

To a solution of compound 2 (1.48 g, 8.25 mmol) in anhydrous DMF (40 mL) was added, at room temperature, sodium tert-butoxide (1.38 g, 8.25 mmol). The mixture was stirred 40 min then a solution of diethyl phosphonate A (2.66 g, 8.25 mmol) in dry DMF (10 mL) was added. After 72 h, the mixture was filtered and concentrated under reduced pressure. The residue dissolved in water was extracted with CHCl₃. The organic extracted fractions were dried (MgSO₄), filtered and concentrated under reduced pressure. The residue was purified by flash chromatography (dichloromethane/methanol: 9/1) to give compound 3 (740 mg, 27%) as a white solid. $^1$H NMR (CD$_3$OD) δ: 8.10 (s, 1H, H-2), 8.03 (s, 1H, H-8), 4.35 (t, J=5.0 Hz, 2H, CH$_2$N), 3.93 (dq, J=8.0 and J=7.0 Hz, 4H, CH$_2$ from P(OEt)$_2$), 3.86 (t, J=5.0 Hz, 2H, CH$_2$O), 3.76 (d, J$_{PH}$=8.5 Hz, 2H, CH$_2$P), 1.11 (td, J=7.0 Hz and J=0.5 Hz, 6H, CH$_3$ from P(OEt)$_2$). $^{13}$C NMR (CD$_3$OD) δ: 157.29, 153.71, 150.67, 143.34, 119.34, 72.15 (d, J=11.9 Hz), 66.63 (d, J$_{CP}$=166 Hz), 63.99 (d, J=6.6 Hz), 44.54, 16.62 (d, J=5.8 Hz). $^{31}$P NMR (CD$_3$OD) δ: 21.56. MS (GT, FAB$^+$): 136 (B+1H)$^+$, 330 (M+1H)$^+$, 352 (M+Na)$^+$.

Compound 4:
9-[2-(phosphanylmethoxy)ethyl]adenine

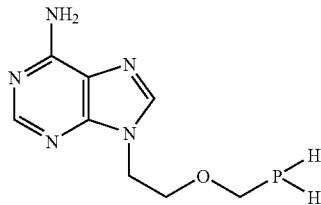

4:

Chlorotrimethylsilane (3.15 mL, 24.78 mmol) was added dropwise to a stirred solution of LiAlH$_4$ (940 mg, 24.78 mmol) in anhydrous THF (50 mL) at −78° C. The resulting mixture was allowed to warm to room temperature and stirred for 2 h. Compound 3 (2.04 g, 6.19 mmol) in anhydrous THF (200 mL) was added to the reducing mixture at −50° C. The mixture was allowed to warm to room temperature and stirred for 2 h. The reaction was stopped by addition of H$_2$O (10 mL) and NaOH (20%, 10 mL). The mixture was filtered through Celite. The organic layer was dried over anhydrous MgSO$_4$, filtered and concentrated under reduced pressure. A purification by flash chromatography (dichloromethane/methanol: 95/5) yielded compound 4 (1.08 g, 78%) as a white powder. HPLC purity>98%; $^1$H NMR (CD$_3$OD) δ: 8.10 (s, 1H, H-8), 7.99 (s, 1H, H-2), 4.30 (t, J=5.1 Hz, 2H, CH$_2$N), 3.87 (m, 2H, CH$_2$P), 3.71 (t, J=5.1 Hz, 2H, CH$_2$O), 3.07 and 2.81 (dm, J$_{PH}$=199.0 Hz, 2H, PH$_2$). $^{13}$C NMR (CD$_3$OD) δ: 157.31, 153.68, 150.71, 143.32, 119.94, 70.23 (d, J=2.8 Hz), 62.49 (d, J$_{CP}$=12.6 Hz), 44.70. $^{31}$P NMR (CD$_3$OD) δ: −144.67 (tt, J$_{PH}$=199.0 Hz and J=7.8 Hz). MS (GT, FAB$^+$): 136 (B+1H)$^+$, 226 (M+1H)$^±$.

Compound 5:
9-[2-(hydroxyphosphinylmethoxy)ethyl]adenine

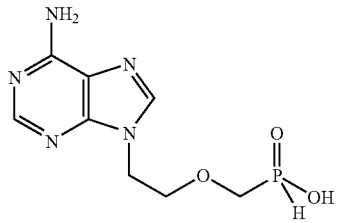

5

To a stirred solution of 4 (1.08 g, 4.79 mmol) in water (30 mL) and THF (30 mL) was added dropwise 2% aqueous hydrogen peroxide (10.8 mL). The mixture was stirred at room temperature for 1 h and concentrated under reduced pressure to give after freeze-drying compound 5 (1.23 g, quant) as a white powder (Lit. 229-230° C.); HPLC purity>99%; $^1$H NMR (DMSO-d6) δ: 8.17 (s, 1H, H-8), 8.15 (s, 1H, H-2), 7.96 and 5.85 (dt, J$_{PH}$=528.0 Hz and J=2.1 Hz, 1H, PH), 7.40 (bs, 2H, NH$_2$), 4.36 (t, J=5.2 Hz, 2H, CH$_2$N), 3.92 (t, J=5.2 Hz, 2H, CH$_2$O), 3.69 (dd, J=7.2 Hz and J=2.1 Hz, 2H, CH$_2$P). $^{13}$C NMR (DMSO-d6) δ: 155.44, 151.66, 149.35, 141.32, 118.46, 70.33 (d, J=10.8 Hz), 69.04 (d, J$_{CP}$=109.0 Hz), 42.39. $^{31}$P NMR (DMSO-d6) δ: 21.15 (dm, J$_{PH}$=528.0 Hz). MS (GT, FAB$^+$): 136 (B+1H)$^+$, 258 (M+1H)$^+$, 515 (2M+1H)$^+$. HRMS (FAB) cald for C$_8$H$_{13}$N$_5$O$_3$P (M+H)$^+$258.0756. found 258.0765.

Compound 7: (R)-9-(2-hydroxypropyl)adenine

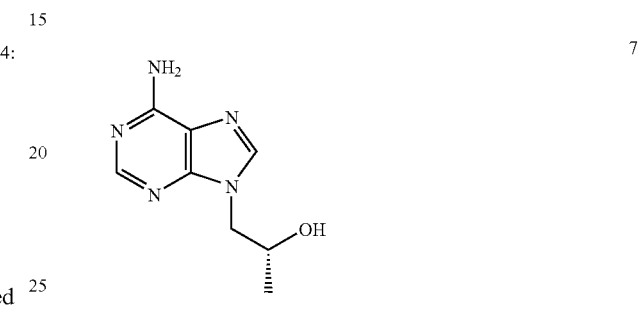

7

A solution of adenine (3.85 g, 28.49 mmol), (R)-propylene carbonate (2.7 mL, 31.34 mmol), and pulverized sodium hydroxide (60 mg, 1.42 mmol) in anhydrous DMF (80 mL) was heated at 140° C. with stirring for 16 h. After cooling, the mixture was then filtered to remove insoluble materials, the filtrate was evaporated under reduced pressure and co-evaporated three times with toluene. The residue was triturated with EtOAc then filtered to give a white solid which was immediately recrystallized in ethanol to afford compound 7 (4.5 g, 81%): mp 193° C. (Lit. 192-195° C.); $^1$H NMR (DMSO-d6) δ: 8.15 (s, 1H, H-2), 8.06 (s, 1H, H-8), 7.22 (bs, 2H, NH$_2$), 5.06 (bs, 1H, OH), 4.06 (m, 3H, CH$_2$N and CHO), 1.12 (d, J=5.7 Hz, 3H, CH$_3$). $^{13}$C NMR (DMSO-d6) δ: 155.87, 152.21, 149.67, 141.44, 118.50, 64.57, 50.07, 20.80. MS (GT, FAB$^+$): 136 (B+1H)$^+$, 194 (M+1H)$^+$, 216 (M+Na)$^+$, 232 (M+K)$^+$, 387 (2M+1H)$^+$.

Compound 8:
(R)-9-[2-(diethylphosphonomethoxy)propyl]adenine

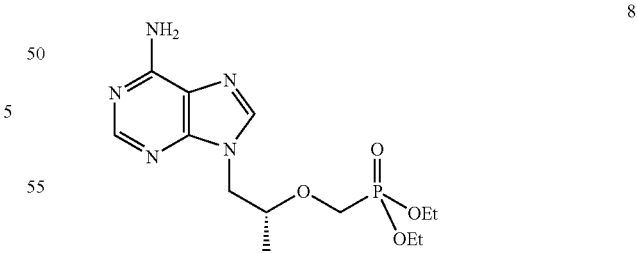

8

To a solution of compound 7 (1.44 g, 7.44 mmol) in anhydrous DMF (30 mL) was added, at room temperature, sodium tert-butoxide (1.25 g, 7.44 mmol). The mixture was stirred 1 h then a solution of diethyl phosphonate A (2.40 g, 7.44 mmol) in anhydrous DMF (10 mL) was added. After 64 h, the mixture was filtered and concentrated under reduced pressure. The residue dissolved in water was extracted with CHCl$_3$. The organic extracted fractions were dried (MgSO$_4$), filtered and concentrated under reduced pressure. The residue was purified by flash chromatography (dichloromethane/methanol: 9/1) to give compound 8 (740 mg, 29%) as a white solid. $^1$H NMR (CD$_3$OD) δ: 8.23 (s, 1H, H-2), 8.15 (s, 1H, H-8), 4.41 (dd, J=14.5 Hz and J=3.2 Hz, 1H, CH$_a$N), 4.22 (dd, J=14.5 Hz and J=7.7 Hz, 1H, CH$_b$N), 4.10 (m, 1H, CHO), 4.03-3.69 (m, 6H, CH$_2$ from P(OEt)$_2$ and CH$_2$P), 1.33 (t, J=7.1 Hz, 6H, CH$_3$ from P(OEt)$_2$), 1.27 (d, J=6.2 Hz, 3H, CH$_3$). $^{13}$C NMR (CD$_3$OD) δ: 157.30, 153.70, 150.89, 143.63, 119.70, 77.65 (d, J=12.3 Hz), 64.32 (d, J$_{CP}$=167 Hz), 64.08 (d, J=6.6 Hz), 63.95 (d, J=6.6 Hz), 49.18, 16.73 (d, J=5.8 Hz), 16.71, 16.70 (d, J=5.8 Hz). $^{31}$P NMR (CD$_3$OD) δ: 22.11. MS (GT, FAB$^+$): 136 (B+1H)$^+$, 344 (M+1H)$^+$, 366 (M+Na)$^+$, 687 (2M+1H)$^+$.

Compound 9:
(R)-9-[2-(phosphanylmethoxy)propyl]adenine

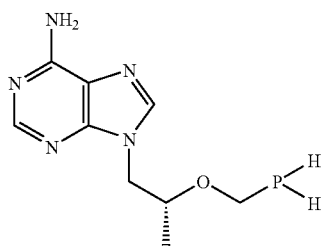

9

Chlorotrimethylsilane (2.62 mL, 20.62 mmol) was added dropwise to a stirred solution of LiAlH$_4$ (782 mg, 20.62 mmol) in anhydrous THF (40 mL) at −78° C. The resulting mixture was allowed to warm to room temperature and stirred for 2 h. Compound 8 (1.77 g, 5.15 mmol) in anhydrous THF (150 mL) was added to the reducing mixture at −78° C. The mixture was allowed to warm to room temperature and stirred for 2 h. The reaction was stopped by addition of H$_2$O (10 mL) and NaOH (20%, 10 mL). The mixture was filtered through Celite. The organic layer was dried over anhydrous MgSO$_4$, filtered and concentrated under reduced pressure. A purification by flash chromatography (dichloromethane/methanol: 95/5) yielded compound 9 (795 mg, 65%) as a white powder. HPLC purity>98%; $^1$H NMR (CD$_3$OD) δ: 8.11 (s, 1H, H-8), 7.97 (s, 1H, H-2), 4.25-3.60 (m, 5H, CH$_2$N, CHO and CH$_2$P), 2.90 and 2.13 (dt, J$_{PH}$=198.5 Hz and J=6.3 Hz, 2H, PH$_2$), 1.08 (d, J=6.1 Hz, 3H, CH$_3$). $^{13}$C NMR (CD$_3$OD) δ: 157.31, 153.68, 150.82, 143.67, 119.73, 75.91 (d, J=2.3 Hz), 60.25 (d, J$_{CP}$=12.0 Hz), 49.48, 17.16. $^{31}$P NMR (CD$_3$OD) δ: −14.86 (tt, J$_{PH}$=198.5 Hz and J=7.3 Hz). MS (GT, FAB$^+$): 136 (B+1H)$^+$, 240 (M+1H)$^+$.

Compound 10:
(R)-9-[2-(hydroxyphosphinylmethoxy)propyl]adenine

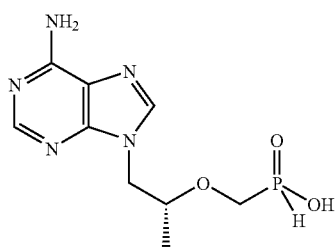

10

To a stirred solution of compound 9 (795 mg, 3.32 mmol) in water (20 mL) and THF (20 mL) was added dropwise 2% aqueous hydrogen peroxide (7.5 mL, 2 eq). The mixture was stirred at room temperature for 1 h and concentrated under reduced pressure to give after freeze-drying compound 10 (900 mg, quant) as a white powder. HPLC purity>99%; $^1$H NMR (DMSO-d6) δ: 8.23 (s, 1H, H-8), 8.20 (s, 1H, H-2), 7.95 and 5.85 (dt, J$_{PH}$=528.0 Hz and J=2.2 Hz, 1H, PH), 7.59 (bs, 2H, NH-2), 4.38 (dd, J=14.2 Hz and J=3.9 Hz, 1H, CH$_b$N), 4.31 (dd, J=14.2 Hz and J=6.0 Hz, 1H, CH$_b$N), 4.10 (m, 1H, CHO), 3.75 (m, 2H, CH$_2$P), 1.13 (d, J=6.8 Hz, 3H, CH$_3$). $^{13}$C NMR (DMSO-d6) δ: 155.21, 151.35, 149.56, 141.79, 118.17, 75.48 (d, J=11.0 Hz), 67.19 (d, J$_{CP}$=111.2 Hz), 46.64, 16.93. $^{31}$P NMR (DMSO-d6) δ: 24.64 (dm, J$_{PH}$=528.0 Hz). MS (GT, FAB$^+$): 136 (B+1H)$^+$, 272 (M+1H)$^+$, 543 (2M+1H)$^+$. HRMS (FAB) cald for C$_9$H$_{15}$N$_5$O$_3$P (M+H)$^+$ 272.0913. found 272.0905.

Example 2

Synthesis of α-Boranophosphonate Nucleoside Derivatives

The strategy used for the preparation of α-boranophosphonate nucleosides is described in scheme 4. The strategies described for the preparation of α-boranophosphates via a phosphoramidite or H-phosphonate intermediate are not applicable to the synthesis of α-boranophosphonate derivatives and have thus required the development of a specific synthetic method. In particular, the final step involves a boronation reaction of an activated H-phosphinate intermediate to obtain the target compounds 9-[2-(boranophosphonomethoxy)ethyl]adenine (6a) and (R)-9-[2-(boranophosphonomethoxy)propyl]adenine (6b).

Scheme 4

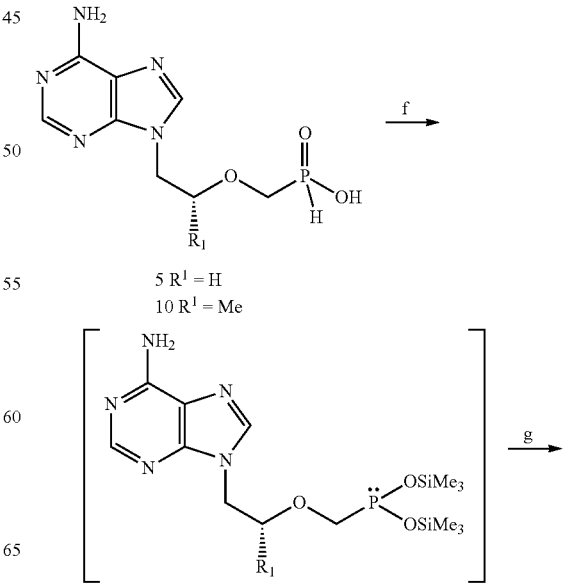

5 R$^1$ = H
10 R$^1$ = Me

47

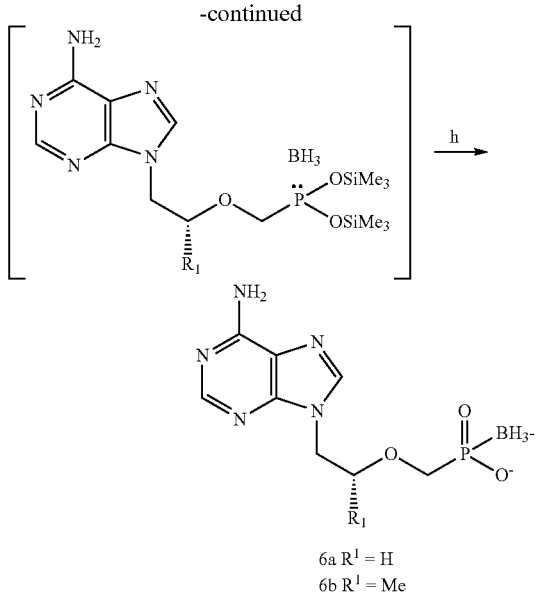

6a R¹ = H
6b R¹ = Me

Reagents and conditions: (f) BSA, THF, ambient temperature, 1 hr.; (g) BH₃, DIPEA, THF, ambient temperature, 1 hr.; (h) NH₄OH:MeOH (1:1, v/v).

As the phosphorous atom of the H-phosphinate intermediate does not present a pair of free electrons and is not a good donor for the introduction of the $BH_3$ group, the boronation procedure requires an in situ intermediate activation of the H-phosphinate with a silylation agent to obtain a disilyl-phosphonite. The H-phosphinates 5 and 10 are activated in situ in anhydrous THF with N,O-bis(trimethylsilyl)acetamide (BSA) for 1 hr. in their corresponding disilyl-phosphonite intermediates. Various boron complexes have been tested in different solvents to optimise the boronation conditions. A rapid and effective boronation was finally obtained with the complex borane-N,N-diisopropylethylamine ($BH_3$:DIPEA). The complexes borane-tetrahydrofuran ($BH_3$:THF), borane-pyridine ($BH_3$:Pyridine), and borane-dimethylsulfide ($BH_3$:$Me_2S$) require significant reduction times and do not improve the yield. In addition, in order to reduce the formation of diboranated products, the quantity of boron complexes was reduced to a maximum of 2 equivalents to obtain the best compromise between consumption of initial material and the appearance of by-products. In situ boronation of the disilyl phosphonites of 5 and 10 with 2 equivalents of $BH_3$:DIPEA results in the formation of -boranophosphonate intermediates. Without isolation, the intermediates obtained were treated with 30% concentrated ammonium hydroxide in methanol (1:1, v/v) to cleave the trimethylsilyl groups thus making it possible to obtain α-boranophosphonates 6a and 6b. The presence of the P—B bond was confirmed by $^{31}P$ NMR showing a typical peak at 83 ppm and 98 ppm respectively. α-boranophosphonates 6a and 6b are purified by reverse-phase chromatography with a yield of 28% and 32% respectively.

Example 3

Synthesis of Thiophosphonate Nucleoside Derivatives 6 and 11

The thiophosphonate derivatives of PMEA and PMPA (compounds 6 and 11 below) are acyclic nucleotide analogues in which the oxygen atom double-bonded to the phosphorus is replaced by a sulphur atom.

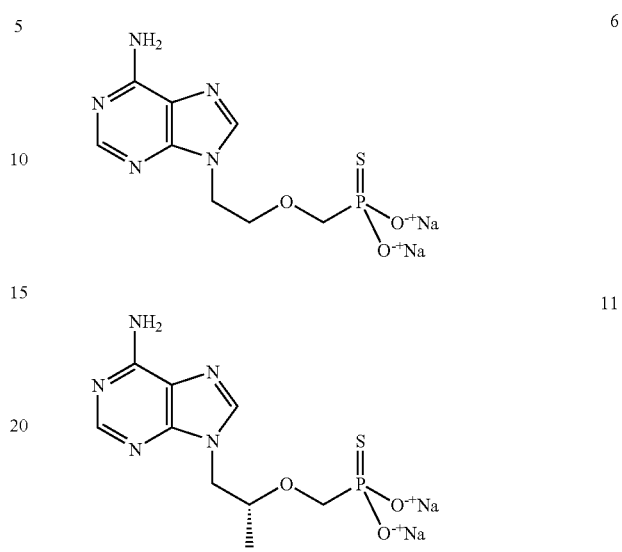

Structures of the Thiophosphonates of PMEA 6 (S-PMEA) and PMPA 11 (S-PMPA)

Scheme 5
Synthetic pathway for the preparation of S-PMEA (6) and S-PMPA (11)

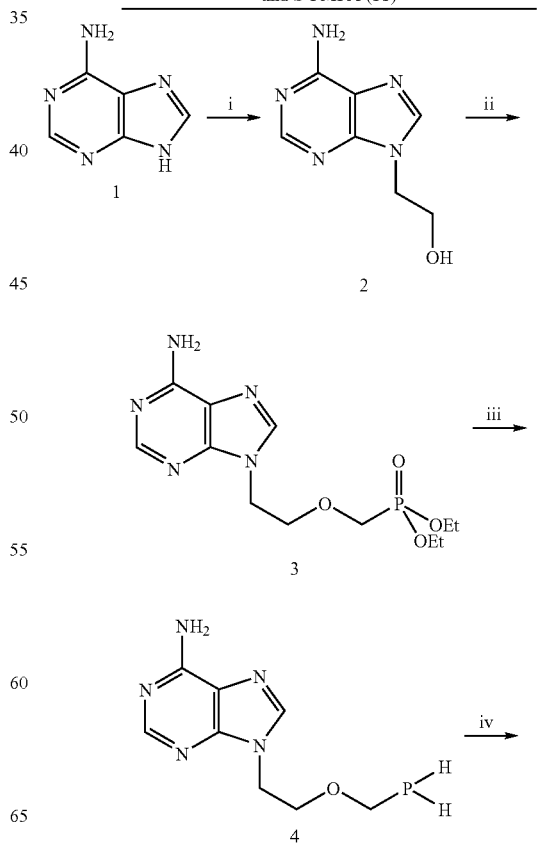

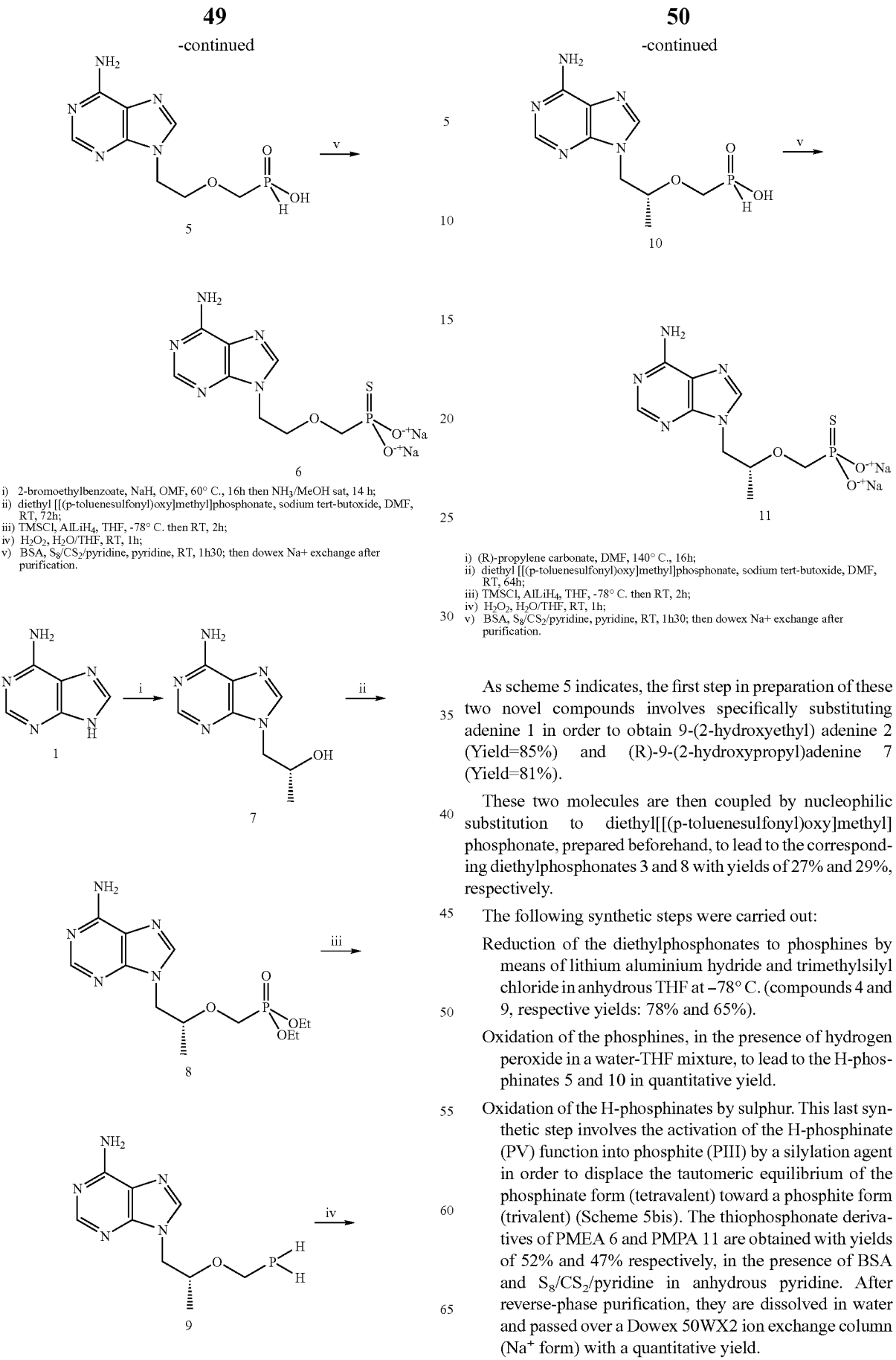

i) (R)-propylene carbonate, DMF, 140° C., 16h;
ii) diethyl [[(p-toluenesulfonyl)oxy]methyl]phosphonate, sodium tert-butoxide, DMF, RT, 64h;
iii) TMSCl, AlLiH$_4$, THF, -78° C. then RT, 2h;
iv) H$_2$O$_2$, H$_2$O/THF, RT, 1h;
v) BSA, S$_8$/CS$_2$/pyridine, pyridine, RT, 1h30; then dowex Na+ exchange after purification.

As scheme 5 indicates, the first step in preparation of these two novel compounds involves specifically substituting adenine 1 in order to obtain 9-(2-hydroxyethyl) adenine 2 (Yield=85%) and (R)-9-(2-hydroxypropyl)adenine 7 (Yield=81%).

These two molecules are then coupled by nucleophilic substitution to diethyl[[(p-toluenesulfonyl)oxy]methyl] phosphonate, prepared beforehand, to lead to the corresponding diethylphosphonates 3 and 8 with yields of 27% and 29%, respectively.

The following synthetic steps were carried out:

Reduction of the diethylphosphonates to phosphines by means of lithium aluminium hydride and trimethylsilyl chloride in anhydrous THF at −78° C. (compounds 4 and 9, respective yields: 78% and 65%).

Oxidation of the phosphines, in the presence of hydrogen peroxide in a water-THF mixture, to lead to the H-phosphinates 5 and 10 in quantitative yield.

Oxidation of the H-phosphinates by sulphur. This last synthetic step involves the activation of the H-phosphinate (PV) function into phosphite (PIII) by a silylation agent in order to displace the tautomeric equilibrium of the phosphinate form (tetravalent) toward a phosphite form (trivalent) (Scheme 5bis). The thiophosphonate derivatives of PMEA 6 and PMPA 11 are obtained with yields of 52% and 47% respectively, in the presence of BSA and S$_8$/CS$_2$/pyridine in anhydrous pyridine. After reverse-phase purification, they are dissolved in water and passed over a Dowex 50WX2 ion exchange column (Na$^+$ form) with a quantitative yield.

Scheme 5bis
Preparation of a thiophosphonate from
the corresponding H-phosphinate precursor

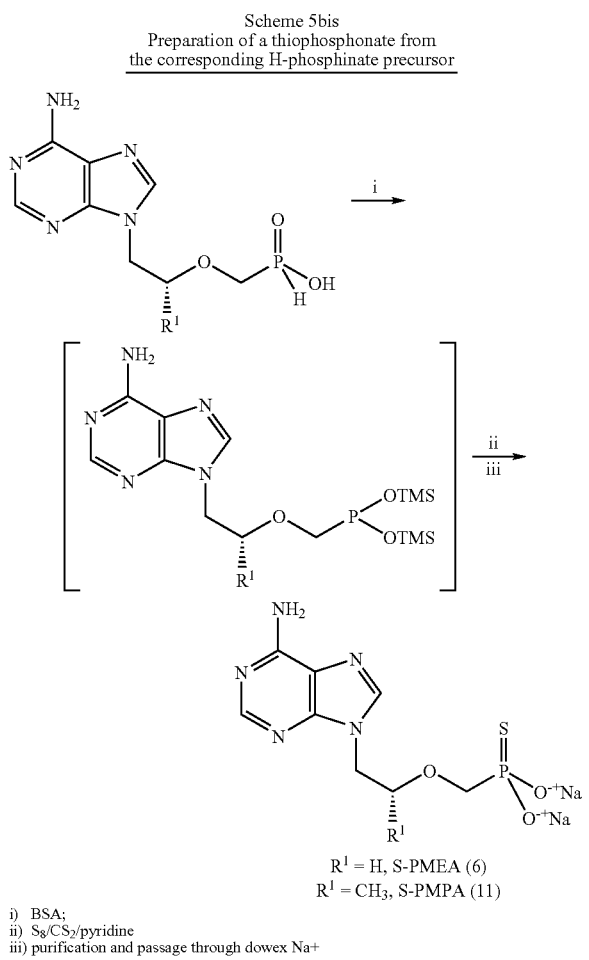

R¹ = H, S-PMEA (6)
R¹ = CH₃, S-PMPA (11)

i) BSA;
ii) S₈/CS₂/pyridine
iii) purification and passage through dowex Na+

Compound 6:
9-[2-(thiophosphonomethoxy)ethyl]adenine

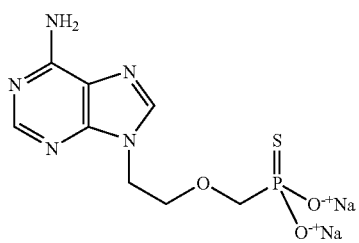

Compound 5 (50 mg, 0.194 mmol) was dried over phosphorus pentoxide under vacuum for 5 h then dissolved in anhydrous pyridine (2 mL). N,O-bis(trimethylsilyl)acetamide (BSA) (240 μL, 0.972 mmol) was added by syringe and the solution was stirred for about 1 h at room temperature, under argon. A freshly solution of elemental sulfur (13 mg, 0.388 mmol) in CS₂/pyridine (1/1, 1 mL) was added, the reaction mixture was stirred for 30 min, and quenched with deionized water (5 mL). After the solvents were evaporated under reduced pressure, the residue was purified by reversed-phase column chromatography (linear gradient 0-100% B). Product fractions were collected, evaporated to dryness and lyophilized. Excess triethylammonium bicarbonate was removed by repeated freeze-drying with deionized water. The residue was dissolved in water and eluted on a Dowex 50WX2 column (Na+ exchange) to give compound 6 (31 mg, 52%) as a white powder after freeze-drying. HPLC purity (>98%); ¹H NMR (D₂O) δ: 8.08 (s, 1H, H-8), 7.93 (s, 1H, H-2), 4.23 (t, J=4.8 Hz, 2H, CH₂N), 3.87 (t, J=4.8 Hz, 2H, CH₂O), 3.60 (d, J=5.8 Hz, 2H, CH₂P). ¹³C NMR (D₂O) δ: 152.23, 149.12, 146.98, 141.98, 116.38, 73.01 (d, $J_{CP}$=120.0 Hz), 68.57 (d, $J_{CP}$=10.6 Hz), 42.27. ³¹P NMR (D₂O) δ: 60.67 (t, J=5.2 Hz). HRMS (TOF, ES-) cald for C₈H₁₁N₅O₃PS (M)⁻ 288.0320. found 288.0347.

Compound 11:
(R)-9-[2-(thiophosphonomethoxy)propyl]adenine

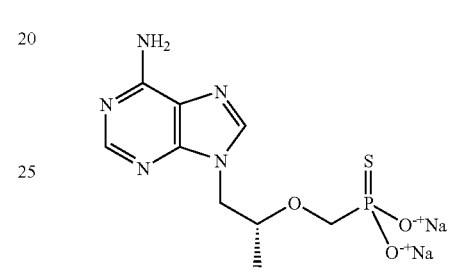

Compound 10 (50 mg, 0.194 mmol) was dried over phosphorus pentoxide under vacuum for 5 h then dissolved in anhydrous pyridine (2 mL). N,O-bis(trimethylsilyl)acetamide (BSA) (240 μL, 0.972 mmol) was added by syringe and the solution was stirred for about 1 h at room temperature, under argon. A freshly solution of elemental sulfur (13 mg, 0.388 mmol) in CS₂/pyridine (1/1, 1 mL) was added, the reaction mixture was stirred for 30 min, and quenched with deionized water (5 mL). After the solvents were evaporated under reduced pressure, the residue was purified by reversed-phase column chromatography (linear gradient 0-100% B). Product fractions were collected, evaporated to dryness and lyophilized. Excess triethylammonium bicarbonate was removed by repeated freeze-drying with deionized water. The residue was dissolved in water and eluted on a Dowex 50WX2 column (Na+ exchange) to give compound 11 (31 mg, 47%) as a white powder. HPLC purity (>98%); ¹H NMR (D₂O) δ: 8.16 (s, 1H, H-8), 8.07 (s, 1H, H-2), 4.29 (dd, J=2.4 Hz and J=14.5 Hz, 1H, CH$_a$N), 3.10 (ddd, J=2.0 Hz, J=6.6 Hz and J=14.6 Hz, 1H, CH$_b$N), 3.95 (m, 1H, CHO), 3.63 (ddd, J=2.0 Hz, J=6.5 Hz and J=12.8 Hz, 1H, CH$_a$P), 3.49 (ddd, J=2.4 Hz, J=6.1 Hz and J=12.8 Hz, 1H, CH$_b$P), 1.05 (d, J=6.1 Hz, 3H, CH₃). ¹³C NMR (D₂O) δ: 152.65, 149.12, 147.25, 142.25, 116.26, 74.46 (d, $J_{cp}$=10.7 Hz), 70.89 (d, $J_{cp}$=121.1 Hz), 46.39, 14.73. ³¹P NMR (D₂O) δ: 61.60 (t, J=4.8 Hz). HRMS (TOF, ES-) cald for C₉H₁₃N₅O₃PS (M)⁻ 302.0477. found 302.0465.

Example 4

Synthesis of Thiophosphonate Diphosphate
Derivatives 12 and 13

In order to carry out inhibition studies of the HIV-1 reverse transcriptase (RT), thiophosphonate diphosphate compounds 12 (S-PMEApp) and 13 (S-PMPApp) were synthesized according to the methodology described in scheme 6 below:

Scheme 6

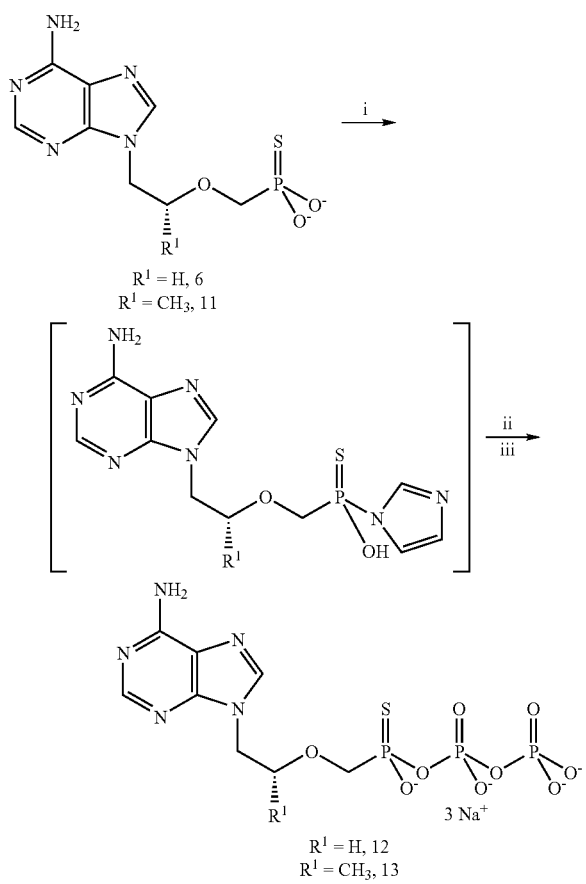

i) 1/ (Im)₂CO, DMF, RT, 4h, 2/ MeOH;
ii) HBu₃N⁺H₂PO₄⁻, Bu₃N, DMF, RT, 72 h
iii) dowex Na+ exchange after purification Thiophosphonates 6 and 11 were activated by carbonyldiimidazole in DMF at ambient temperature. The resulting intermediate was allowed to react with a solution of 0.5 M tributylammonium pyrophosphate in DMF in the presence of tributylamine, to lead to thiophosphonate diphosphate derivatives 12 (S-PMEApp) and 13 (S-PMPApp) with yields respectively of 14% and 22% after purification and passage through Dowex ion exchange (Na⁺).

Compound 12: 9-[2-(diphosphorylthiophosphonomethoxy)ethyl]adenine

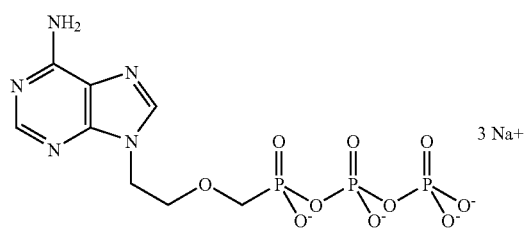

The thiophosphonate 6 (20 mg, 0.069 mmol) was dissolved in DMF (2 mL) and treated with 1,1'-carbonyldiimidazole (30 mg, 0.278 mmol). The resulting mixture was stirred at room temperature for 24 h. Excess of CDI was decomposed by addition of anhydrous methanol (8 µL) and stirring was continued for 30 min. Anhydrous tri-n-butylamine (50 µL) and tributylammonium pyrophosphate (700 µl, of a 0.5M solution in DMF) were added and the mixture was stirred at room temperature for 3 days. The reaction was stopped by the addition of 5 mL of cold water. The solvent was removed under vacuum, the residue dissolved in water, and the solution applied to a DEAE-Sephadex column (linear gradient 0-100% B). The appropriate fractions were collected, evaporated to dryness and lyophilized. The residue was dissolved in water and passed through a Dowex 50WX2 (Na⁺ form) column to give compound 12 as trisodium salt (6.3 mg, 14%); HPLC purity (>99%). $^{31}$P NMR (D₂O) δ: 61.96, −10.80, −22.98. HRMS (TOF, ES−) cald for $C_8H_{13}N_5O_9P_3S$ (M)⁻ 447.9647. found 447.9656.

Compound 13: (R)-9-[2-(pyrophosphoroxythiophosphonomethoxy)propyl]adenine

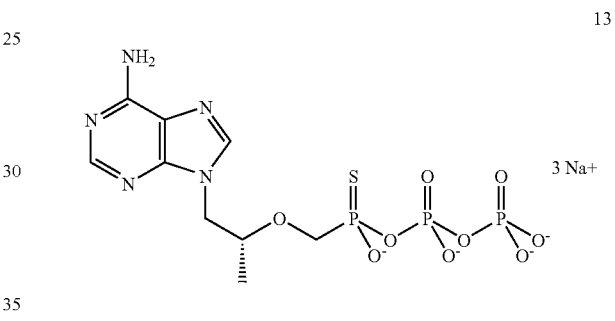

The thiophosphonate 11 (15 mg, 0.05 mmol) was dissolved in DMF (2 mL) and treated with 1,1'-carbonyldiimidazole (20 mg, 0.2 mmol). The resulting mixture was stirred at room temperature for 24 h. Excess CDI was decomposed by addition of anhydrous methanol (6 µL) and stirring was continued for 30 min. Anhydrous tri-n-butylamine (36 µL) and tributylammonium pyrophosphate (500 µL of a 0.5M solution in DMF) were added and the mixture was stirred at room temperature for 3 days. The reaction was stopped by the addition of 5 mL of cold water. The solvent was removed under vacuum, the residue dissolved in water, and the solution applied to a DEAE-Sephadex column (linear gradient 0-100% B). The appropriate fractions were collected, evaporated to dryness and lyophilized. The residue was dissolved in water and passed through a Dowex 50WX2 (Na⁺ form) column to give compound 13 as trisodium salt (5.2 mg, 22%); HPLC purity (>99%). $^{31}$P NMR (D₂O) δ: 60.89, −5.77, −21.76. HRMS (TOF, ES−) cald for $C_9H_{15}N_5O_9P_3S$ (M)⁻ 461.9803. found 461.9802.

Example 5

Synthesis of Thiophosphonate Nucleoside Derivatives where R¹ is —CH₂OH, —CH₂CH₂OH, —CH₂F or Halomethyl Other thiophosphonate derivatives of the invention may be prepared according to the following synthetic scheme:

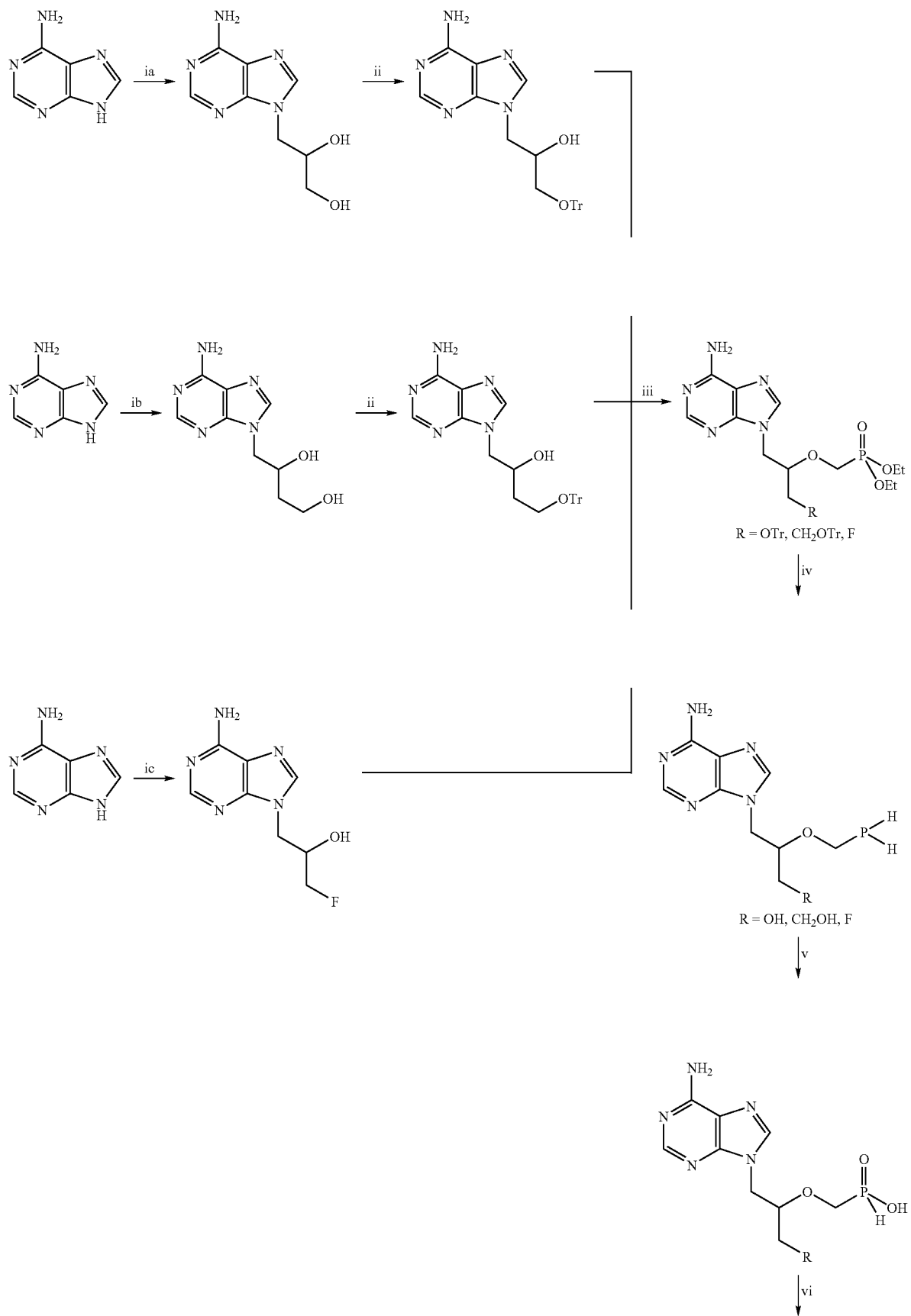

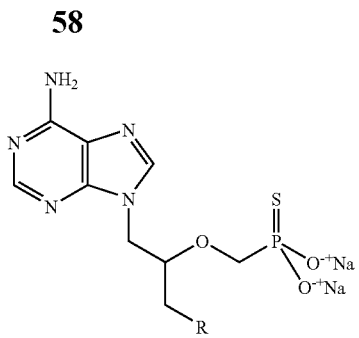

ia) (S)-2,2-dimethyl-4-hydroxymethyl-1,3-dioxolane, NaH, DMF, then H$_3$O$^+$
ib) (R,S)-2,2-dimethyl-4-hydroxyethyl-1,3-dioxolane, NaH, DMF then H$_3$O$^+$
ic) 2-fluoromethyloxirane, K$_2$CO$_3$,
ii) TrCl, pyridine
iii) diethyl [[(p-toluenesulfonyl)oxy]methyl]-phosphonate, sodium tert-butoxide, DMF;
iv) TMSCl, AlLiH$_4$, THF, then H$_3$O$^+$;
v) H$_2$O$_2$, H$_2$O/THF;
v) BSA, S$_8$/CS$_2$/pyridine, pyridine, then dowex Na+ exchange after purification.

As the reader will appreciate, the carbon atom bearing R$^1$ may of R- or S-configuration, or racemic.

Example 6

Synthesis of Fluorophosphonate Derivatives

Fluorophosphonate derivatives may be prepared according to the following synthetic scheme:

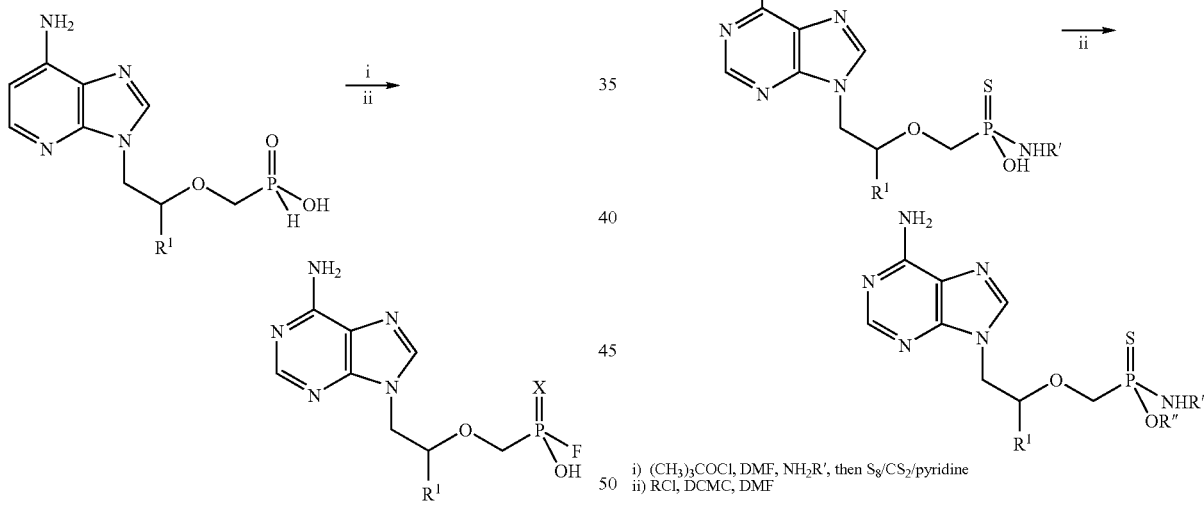

X = O i) H$_2$O$_2$, H$_2$O/THF ii) Diethylamino sulfur trifluoride (DAST), CH$_3$CN, -78° C.
X = S, i) S$_8$/CS$_2$/pyridine ii) Diethylamino sulfur trifluoride (DAST), CH$_3$CN, -78° C.

As the reader will appreciate, the above methodology may be practiced with compounds where R$^1$ is hydrogen, methyl, ethyl, hydroxymethyl, hydroxyethyl and C$_{1-6}$haloalkyl, and where the carbon atom bearing R$^1$ may of R- or S-configuration, or racemic.

Example 7

Synthesis of Aminothiophosphonate Derivatives

Aminothiophosphonate derivatives may be prepared according to the following synthetic scheme.

i) (CH$_3$)$_3$COCl, DMF, NH$_2$R', then S$_8$/CS$_2$/pyridine
ii) RCl, DCMC, DMF The methodology may be applied to the synthesis of thiophosphonamide prodrugs having the following structure:

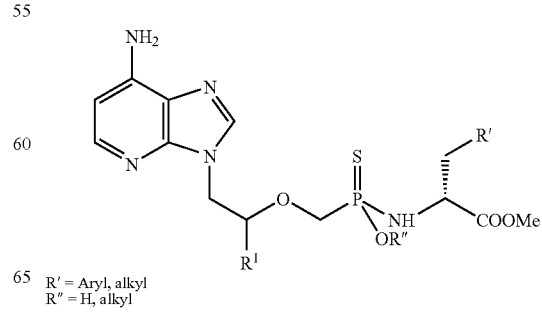

R' = Aryl, alkyl
R" = H, alkyl

The reader may refer to Wagner C. R. et al. Bioorganic & Medicinal Chemistry Letters. 1995, 5, 1819-1824 for further guidance.

As the reader will appreciate, the above methodologies may be practiced with compounds where $R^1$ is hydrogen, methyl, ethyl, hydroxymethyl, hydroxyethyl and $C_{1-6}$haloalkyl, and where the carbon atom bearing $R^1$ may of R- or S-configuration, or racemic.

Example 8

Synthesis of Alkylthiophosphonate Derivatives

Alkylthiophosphonate derivatives may be prepared according to the following synthetic scheme.

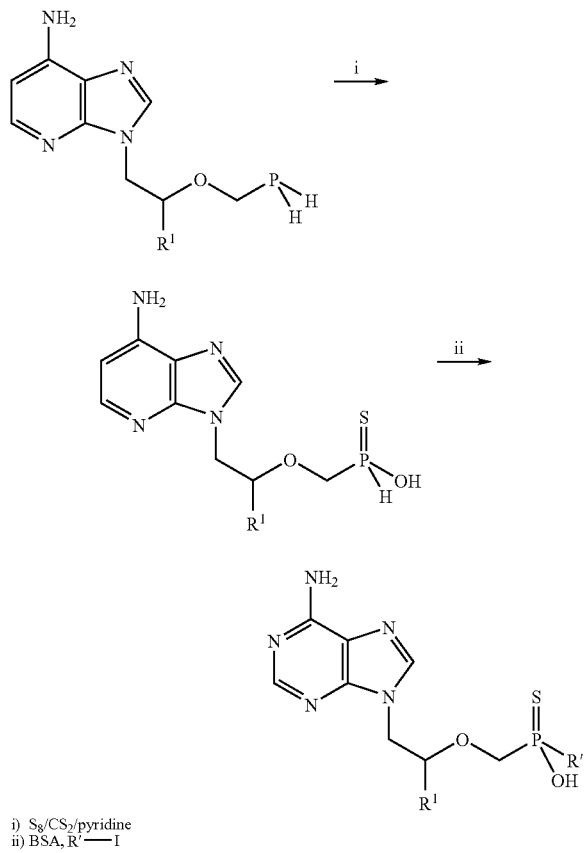

i) S₈/CS₂/pyridine
ii) BSA, R'——I

As the reader will appreciate, the above methodology may be practiced with compounds where $R^1$ is hydrogen, methyl, ethyl, hydroxymethyl, hydroxyethyl and $C_{1-6}$haloalkyl, and where the carbon atom bearing $R^1$ may of R- or S-configuration, or racemic.

Example 9

Synthesis of Mono and Bis-POC Pro-Drugs from Thiophosphonate Derivatives

A pro-drug is a substance lacking biological activity, which under the action of the cellular machinery is transformed into the active substance (the drug). The pro-drug may be synthesized from a biologically active entity of which the chemical functions involved in biological activity are temporarily protected by enzyme-labile groups. Under the action of enzymes (esterases, reductases), these groups are cleaved to regenerate the active molecule. A judicious choice of these enzyme-labile groups thus makes it possible to specifically release the drug, at the location where the enzymatic activity used in the unmasking step is the greatest, by playing on the difference in enzymatic content between the intra- and extra-cellular medium. In general, pro-drugs are used to improve in vivo the pharmacological properties of the drug (stability, solubility, absorption, distribution, targeting, metabolism).

In order to improve the pharmacological properties of nucleotide analogues, various pro-drugs have been developed. In particular, adefovir (PMEA) and tenofovir (PMPA) are used in therapy in the form of pro-drugs (Robins et al., *Antimicrob. Agents Chemother.*, vol. 42 (3), p: 612-617, 1998), which intracellularly liberate, by enzymatic cleavage, the monophosphorylated entity.

To improve the pharmacological properties of the thiophosphonate derivatives 6 and 11, it is possible to carry out the synthesis of mono and bis pro-drugs of the thiophosphonate derivatives of PMEA 6 and PMPA 11 according to the methodologies described in Schemes 7 and with the POC group or isopropyloxymethylcarbonyl (Robins et al., 1998, cited above), bearing an ester function substrate for cellular esterases.

Isopropyloxymethylcarbonyl chloride is prepared beforehand according to a protocol described in the literature (J. D. Thomas et al. Tetrahedron Letters, 2007, 48, 109-112).

Mono-POC compounds 14 and 16 and bis-POC compounds 15 and 17 were obtained according to different protocols.

Scheme 7 Synthesis of pro-drugs mono-POC S-PMEA 14 and mono-POC S-PMPA 16

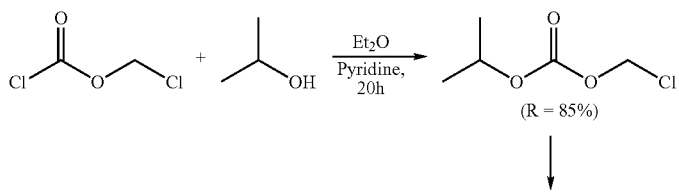

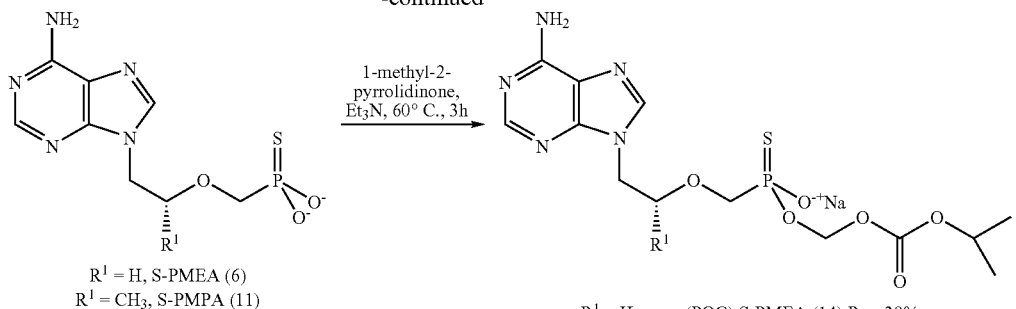

A solution of S-PMEA 6 or S-PMPA 11 in 1-methyl-2-pyrrolidinone and triethylamine was heated at 60° C. for 30 minutes. Isopropyl chloromethyl carbonate, synthesized beforehand, was then added, and the reaction mixture was stirred for 3 hours at 60° C. After purification and passage through a Dowex 50WX2 ion-exchange column (Na⁺ form), the mono-POC compounds 14 and 16 were obtained, with yields of 38% and 14% respectively.

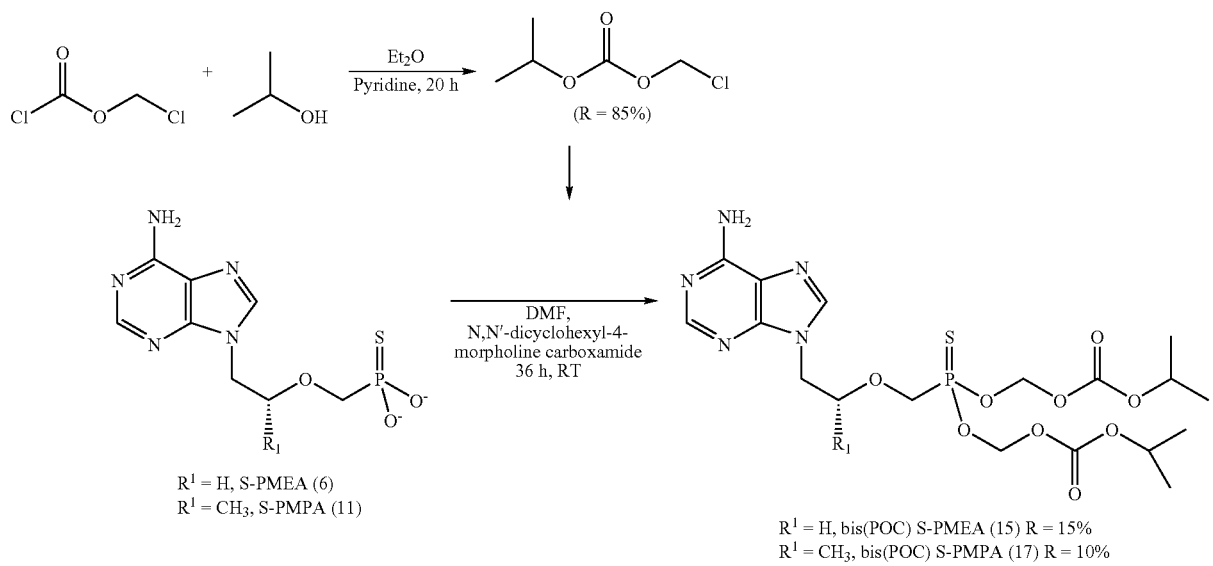

N,N'-dicyclohexyl-4-morpholine carboxamidine and isopropyl chloromethyl carbonate, synthesized beforehand, was added to a solution of S-PMEA 6 or S-PMPA 11 in DMF. The reaction mixture was stirred at ambient temperature for 36 hours. After purification, the expected bis-POC compounds 15 and 17 were obtained with yields of 15% and 10% respectively.

Compound: Chloromethyl Isopropyl Carbonate

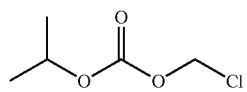

Propan-2-ol (785 mg, 13.19 mmol) was added to a solution of chloromethyl chloroformate (1.7 g, 13.19 mmol) in dry ethyl ether (20 mL). The reaction mixture was cooled to 0° C. Pyridine (1.043 g, 13.19 mmol) was added dropwise with stirring. Thereafter, the reaction mixture was stirred at room temperature for 20 hours. The heterogenous mixture was filtered and the filtrate was washed with citric acid 1% (2×20 mL), NaHCO$_3$ 1% (2×20 mL) and brine (20 mL). The organic layer was dried over Na$_2$SO$_4$, filtered and evaporated to give desired compound (1.71 g, 85%). $^1$H NMR (CDCl$_3$) δ: 5.69 (s, 2H, ClCH$_2$O), 4.92 (sept, J=6.26 Hz, 1H, OCH(CH$_3$)$_2$), 1.30 (d, J=6.27 Hz, 6H, OCH(CH$_3$)$_2$). $^{13}$C NMR (CDCl$_3$) δ: 152.68, 73.60, 71.95, 21.52 (2C).

Compound 14:
9-[2-(thiophosphonomethoxy)ethyl]adenine, mono isopropyloxycarbonyloxy methyle ester

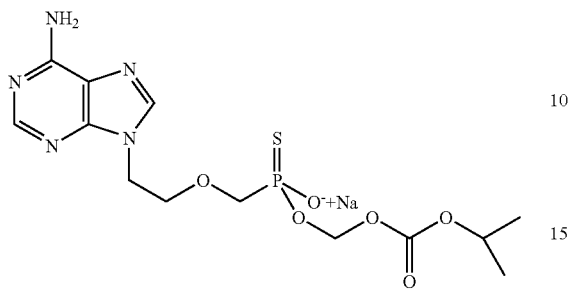

A mixture of 9-[2-(thiophosphonomethoxy)ethyl]adenine 6 (15 mg, 0.0518 mmol) and triethylamine (TEA) (26 mg, 0.259 mmol) in 2 mL of anhydrous and degazed 1-methyl-2-pyrrolidinone (2 mL) was heated to 60° C. for 30 minutes. Isopropyl chloromethyl carbonate (POCCl) (39 mg, 0.259 mmol) was then added. The reaction mixture was stirred at 60° C. for 3 hours. The solvent was removed under reduced pressure and the crude material was purified by reverse-phase preparative HPLC (X-terra column). Ion exchanges (Dowex 50WX2, Na$^+$ form) and freeze-drying gave desired compound 14 as a white solid (8 mg, 38%). HPLC purity>97%. $^1$H NMR (CDCl$_3$) δ: 8.30 (s, 1H, H-8), 8.21 (s, 1H, H-2), 5.93 (s large, 2H, NH$_2$), 5.45 (d, J=13.57 Hz, 2H, OCH$_2$O), 4.85 (sept, J=6.25 Hz, 1H, OCH(CH$_3$)$_2$), 4.42 (t, J=4.90 Hz, 2H, CH$_2$N), 3.96 (d, J=4.90 Hz, 2H, CH$_2$O), 3.79 (d, J=5.84 Hz, 2H, OCH$_2$P), 1.24 (d, J=6.29 Hz, 6H, OCH(CH$_3$)$_2$). $^{31}$P NMR (CDCl$_3$) δ: 31.05. MS: (TOF MS ES−): 404.3 (M−1H)$^+$, 809.6 (2M−1H)$^+$.

Compound 15:
9-[2-(thiophosphonomethoxy)ethyl]adenine, bis isopropyloxycarbonyloxy methyl ester

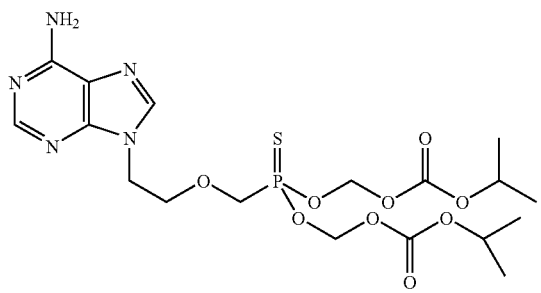 [SMILES: CC(C)OC(=O)OCOP(=S)(COCCn1cnc2c(N)ncnc21)OCOC(=O)OC(C)C]

To a stirred solution of 9-[2-(thiophosphonomethoxy) ethyl]adenine 6 (15 mg, 0.0518 mmol) in 2 mL of anhydrous and degazed DMF was added N,N'-dicyclohexyl-4-morpholine carboxamidine (30 mg, 0.103 mmol) and isopropyl chloromethyl carbonate (POCCl) (39 mg, 0.259 mmol). The reaction mixture was stirred at room temperature for 36 hours. The insolubles were filtered off and the filtrate was concentrated in vacuo. The residue was then partitioned between toluene (1 mL) and water (1 mL), separated and the water layer was then extracted with toluene (2×1 mL). Organic layers were combined and concentrated in vacuo. The residue was purified by silica gel column chromatography, eluting with 5% MeOH/CH$_2$Cl$_2$ to give desired compound 15 (4 mg, 15%). HPLC purity>98%. $^1$H NMR (CDCl$_3$) δ: 8.30 (s, 1H, H-8), 8.21 (s, 1H, H-2), 5.93 (s large, 2H, NH$_2$), 5.45 (m, 4H, OCH$_2$O), 4.88 (m, 2H, OCH(CH$_3$)$_2$), 4.40 (t, J=4.90 Hz, 2H, CH$_2$N), 3.94 (d, J=4.90 Hz, 2H, CH$_2$O), 3.79 (d, J=5.84 Hz, 2H, OCH$_2$P), 1.29 (m, 12H, OCH(CH$_3$)$_2$). $^{31}$P NMR (CDCl$_3$) δ: 42.10. MS: (TOF MS ES+): 522.3 (M+1H)$^+$.

Compound 16:
(R)-9-[2-(thiophosphonomethoxy)propyl]adenine, mono isopropyloxycarbonyloxy methyl ester

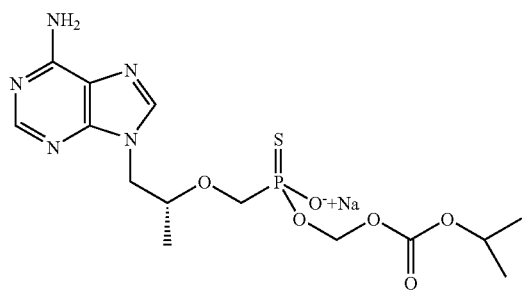

A mixture of (R)-9-[2-(thiophosphonomethoxy)propyl] adenine 11 (15 mg, 0.0494 mmol) and triethylamine (TEA) (25 mg, 0.247 mmol) in 2 mL of anhydrous and degazed 1-methyl-2-pyrrolidinone (2 mL) was heated to 60° C. for 30 minutes. Isopropyl chloromethyl carbonate (POCCl) (37 mg, 0.247 mmol) was then added. The reaction mixture was stirred at 60° C. for 3 hours. Solvent was removed under reduced pressure and the crude material was purified by reverse-phase preparative HPLC (X-terra column). Ion exchanges (Dowex 50WX2, Na$^+$ form) and freeze-drying gave desired compound 16 as a white solid (3 mg, 15%). $^1$H NMR (CDCl$_3$) δ: 8.35 (s, 1H, H-8), 8.25 (s, 1H, H-2), 6.45 (s large, 2H, NH$_2$), 5.43 (d, J=13.62 Hz, 2H, OCH$_2$O), 4.81 (sept, J=6.25 Hz, 1H, OCH(CH$_3$)$_2$), 4.40 (dd, J$_1$=14.06 et J$_2$=2.52, 1H, CH$_a$N), 4.17 (dd, J$_1$=14.13 et J$_2$=7.18, 1H, CH$_b$N), 4.13 (m, 1H, CH(Me)O), 3.76 (m, 2H, OCH$_2$P), 1.28 (d, J=6.28 Hz, 6H, OCH(CH$_3$)$_2$), 1.21 (d, J=6.20 Hz, 3H, CH(CH$_3$)O). $^{31}$P NMR (CDCl$_3$) δ: 31.82. MS: (TOF MS ES−): 418.2 (M−1H)$^+$, 837.4 (2M−1H)$^+$.

Compound 17:
(R)-9-[2-(thiophosphonomethoxy)propyl]adenine, bis isopropyloxycarbonyloxy methyl ester

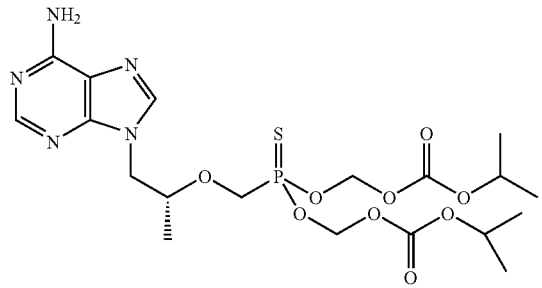 [SMILES: CC(C)OC(=O)OCOP(=S)(CO[C@H](C)Cn1cnc2c(N)ncnc21)OCOC(=O)OC(C)C]

To a stirred solution of (R)-9-[2-(thiophosphonomethoxy) propyl]adenine 11 (15 mg, 0.0495 mmol) in 2 mL of anhydrous and degazed DMF was added N,N'-dicyclohexyl-4-morpholine carboxamidine (29 mg, 0.0989 mmol) and isopropyl chloromethyl carbonate (POCCl) (37.7 mg, 0.247 mmol). Reaction mixture was stirred at room temperature for 36 hours. The insolubles were filtered off and the filtrate was concentrated in vacuo. The residue was then partitioned between toluene (1 mL) and water (1 mL), separated and the water layer was then extracted with toluene (2×1 mL). Organic layers were combined and concentrated in vacuo. The residue was purified by silica gel column chromatography, eluting with 5% MeOH/$CH_2Cl_2$ to give desired compound 17 (3 mg, 11%). $^1$H NMR ($CDCl_3$) δ: 8.32 (s, 1H, H-8), 8.26 (s, 1H, H-2), 6.39 (s large, 2H, $NH_2$), 5.46 (m, 4H, $OCH_2O$), 4.90 (m, 2H, $OCH(CH_3)_2$), 4.40 (dd, $J_1$=14.06 et $J_2$=2.52, 1H, $CH_aN$), 4.17 (dd, $J_1$=14.13 et $J_2$=7.18, 1H, $CH_bN$), 4.13 (m, 1H, CH(Me)O), 3.76 (m, 2H, $OCH_2P$), 1.31 (m, 12H, $OCH(CH_3)_2$), 1.20 (d, 6.20 Hz, 3H, $CH(CH_3)O$). $^{31}$P NMR ($CDCl_3$) δ: 42.25. MS: (TOF MS ES+): 536.4 $(M+1H)^+$.

Example 10

Synthesis of bis-SATE Pro-Drugs from Thiophosphonate Derivatives

SATE thiophosphonate prodrug derivatives may be prepared according to the following synthetic scheme.

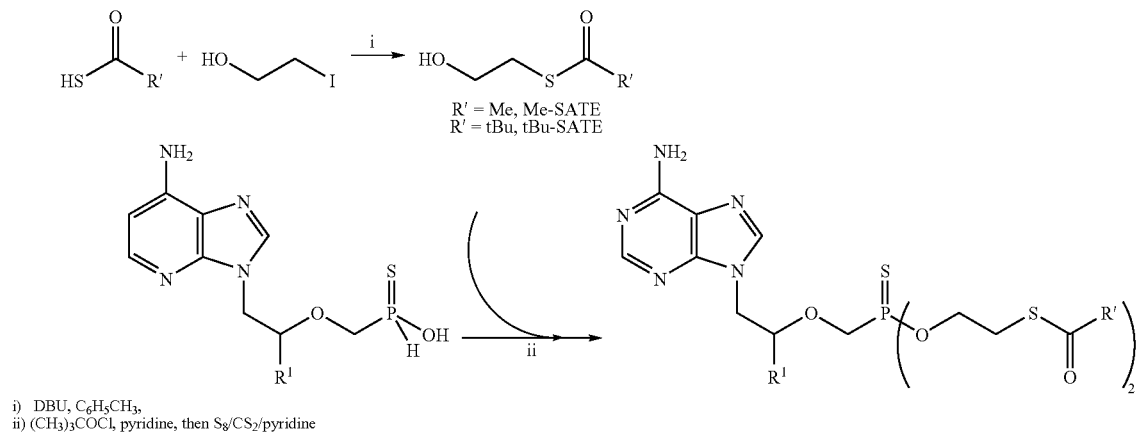

i) DBU, $C_6H_5CH_3$,
ii) $(CH_3)_3COCl$, pyridine, then $S_8/CS_2$/pyridine

The reader may refer to Perigaud C et al. Bioorganic & Medicinal Chemistry letters. 3 (12), 2521-2526, 1993 for further guidance.

As the reader will appreciate, the above methodology may be practiced with compounds where $R^1$ is hydrogen, methyl, ethyl, hydroxymethyl, hydroxyethyl and $C_{1-6}$haloalkyl, and where the carbon atom bearing $R^1$ may of R- or S-configuration, or racemic.

Example 11

Antiviral Activity

1) Anti-HBV Test
a) Tests in Infected HepAD38 Cells
The tetracycline-responsive cell lines HepAD38 was used (Ladner et al., *Antimicrob. Agents Chemother.* 41:1715-1720, 1997). These are hepatoma cells that have been stably transfected with a cDNA copy of the pregenomic RNA of wild-type virus. Withdrawal of tetracycline from the culture medium results in the initiation of viral replication. This offers the advantage, in contrast to the Hep G2.2.15 cell lines commonly used, that there is no, or very limited background viral DNA synthesis. Cells were cultured at 37° C. in a humidified 5% $CO_2$/air atmosphere in seeding medium, DMEM/Ham's F12 (50/50) supplemented with 10% (v/v) heat-inactivated fetal calf serum, 100 IU/ml penicillin, 50 μg/ml streptomycin, 100 Ξg/ml kanamycin, 400 μg/ml G418, and 0.3 μg/ml tetracycline. When the assay was started, the cells were seeded in 48-well plates at a density of 5×105/well. After 2-3 days the cultures were induced for viral production by washing with prewarmed PBS and were fed with 200p1 assay medium (seeding medium without tetracycline and G418) with or without the antiviral compounds. Medium was changed after 3 days. The antiviral effect was quantified by measuring levels of intracellular viral DNA at day 6 post-induction, by a real time quantitative PCR (Q-PCR) method. Total cellular DNA was extracted from the cells by means of a commercial kit. The Q-PCR was performed in a reaction volume of 25p1 using the TaqMan® Universal PCR Master Mix with forward primer (5'-CCG TCT GTG CCT TCT CAT CTG-3'; final concentration: 600 nM), reversed primer (5'-AGT CCA AGA GTY CTC TTA TRY AAG ACC TT-3'; final concentration: 600 nM), and Taqman® probe (6-FAM-CCG TGT GCA CTT CGC TTC ACC TCT GC-TAMRA; final concentration 150 nM). The reaction was analyzed using a SDS 7000. A plasmid containing the full length insert of the HBV genome was used to prepare the standard curve. The amount of viral DNA produced in treated cultures was expressed as a percentage of the mock treated samples. Compounds that exhibit selective antiviral activity in a first assay were retested to confirm the activity. The cytostatic effect of the various compounds was assessed employing the parent hepatoma cell line HepG2. The effect of the compounds on exponentially growing HepG2 cells was evaluated by means of the MTS method. Briefly, cells were seeded at a density of 3000/well (96 well plate) and were allowed to proliferate for 3 days in the absence or presence of compounds after which the optical density was measured with a 96-well plate reader and cell density was determined.

The results are presented in Tables I and II below:

TABLE I

Activities and cytotoxicity of the thiophosphonates 6 (S-PMEA) and reference compound PMEA against HBV in infected HepAD38 cell cultures

|  | $EC_{50}$* (µM) HBV | $TC_{50}$** (µM) | SI*** |
| --- | --- | --- | --- |
| S-PMEA 6 | 9.6 | >166 | >17 |
| PMEA | 8.8 | >200 | >23 |

[*$EC_{50}$: effective concentration of compounds inducing a 50% reduction of the level of viral DNA present in the culture.
**$TC_{50}$: cytotoxic concentration of compounds inducing a 50% reduction of the cell density.
***SI = selectivity index: ratio of the cytotoxicity ($TC_{50}$) to the efficacy ($EC_{50}$). The more the selectivity index is high the more the compound is efficient.

The results show that the S-PMEA 6 derivative presents an efficacy equivalent than those of PMEA.

TABLE II

Activities and cytotoxicity of the thiophosphonates 11 (S-PMPA) and reference compound PMPA against HBV in infected HepAD38 cell cultures

|  | $EC_{50}$* (µM) HBV | $TC_{50}$** (µM) | SI*** |
| --- | --- | --- | --- |
| S-PMPA 11 | 2.26 | >174 | >77 |
| PMPA | 2.88 | >35 | >12 |

[*$EC_{50}$: effective concentration of compounds inducing a 50% reduction of the level of viral DNA present in the culture.
**$TC_{50}$: cytotoxic concentration of compounds inducing a 50% reduction of the cell density.
***SI = selectivity index: ratio of the cytotoxicity ($TC_{50}$) to the efficacy ($EC_{50}$). The more the selectivity index is high the more the compound is efficient.

The results show that S-PMPA derivative 11 presents an efficacy equivalent than those of PMPA but with a selectivity index more than six times greater on account of a lower cytotoxicity.

b) Tests in Infected Huh7 Cells

The results are presented in Tables III and IV below:

TABLE III

Activities and cytotoxicity of thiophosphonates 6 (S-PMEA) and reference compound PMEA against HBV in infected Huh7 cells cultures.

|  | $EC_{50}$* (µM) HBV |
| --- | --- |
| S-PMEA 6 | 4.5 |
| PMEA | 6 |

[*$EC_{50}$: effective concentration of compounds inducing a 50% reduction in the level of viral DNA present in the culture.]

The results show that S-PMEA derivative 6 presents efficacy greater than those of PMEA.

TABLE IV

Activities and cytotoxicity of thiophosphonates 11 (S-PMPA) and reference compound PMPA against HBV in infected Huh7 cells cultures.

|  | $EC_{50}$* (µM) HBV |
| --- | --- |
| S-PMPA 11 | 5 |
| PMPA | 4 |

[*$EC_{50}$: effective concentration of compounds inducing a 50% reduction in the level of viral DNA present in the culture.]

The results show that S-PMPA derivative 11 presents efficacy equivalent than those of PMPA.

2) Anti-HIV Test on Wild-Type Viruses a) Tests on HIV-1 (III$_B$) and HIV-2 (ROD)

Compounds 6 and 11 have been evaluated against HIV-1 (III$_B$) and HIV-2(ROD) in CEM cell cultures. Briefly, CEM cells (4.5×10⁵ cells per ml) were suspended in fresh culture medium and infected with HIV-1 at 100 $CCID_{50}$ per ml of cell suspension. Then, 100 µl of the infected cell suspension were transferred to microplate wells, mixed with 100 µl of the appropriate dilutions of the test compounds, and further incubated at 37° C. After 4 to 5 days, giant cell formation was recorded microscopically in the CEM cell cultures. The 50% effective concentration ($EC_{50}$) corresponds to the compound concentrations required to prevent syncytium formation by 50% in the virus-infected CEM cell cultures.

The results are presented in Table V below:

TABLE V

Activity and cytotoxicity of S-PMEA 6 and S-PMPA 11 against HIV-1 (III$_B$) and HIV-2 (ROD) in infected CEM cell cultures.

|  | $EC_{50}$* (µM) | $EC_{50}$* (µM) | $TC_{50}$** | SI*** | |
| --- | --- | --- | --- | --- | --- |
|  | HIV-1 | HIV-2 | (µM) | HIV-1 | HIV-2 |
| S-PMEA 6 | 12.2 | 10.4 | >332 | 27 | 31 |
| S-PMPA 11 | 11.1 | 8.6 | >165 | 15 | 19 |

[*$EC_{50}$: effective concentration of compounds inducing a 50% reduction in the formation of syncytia in the cultures of infected CEM cells.
**$TC_{50}$: cytotoxic concentration of compounds inducing a 50% reduction in the cell density.
***SI = selectivity index: ratio of the cytotoxicity ($TC_{50}$) to the efficacy ($EC_{50}$). The more the selectivity index is high the more the compound is efficient.

The results show a good effectiveness for S-PMEA 6 and S-PMPA 11 against HIV-1 and HIV-2 in infected cells cultures, an absence of cytotoxicity and a good selectivity index. Moreover, they are active within a concentration range equivalent to that found for PMEA and PMPA on the same viruses (application WO 03 002580, published 9 Jan. 2003).

b) Tests on HIV-1 LAI

The anti-HIV activity of S-PMEA 6 and S-PMPA 11 and reference compounds PMEA and PMPA was evaluated in CMSP cultures infected by HIV-1-LAI (100 "Tissue Culture Infectious Dose 50%", TCID50). The CMSPs were separated from the other formed elements of human peripheral blood by a Ficoll-Hypaque density gradient, activated by 1 µg/ml of PHA-P for 48 hours and then cultured in RPMI1640 culture medium supplemented with 10% SVF, 2 mM L-Glutamine, 1% PSN and 20 IU/ml recombinant human interleukin-2. The activated CMSPs were treated with 6 different concentrations of the compounds and infected with the lymphocyte tropism reference strain HIV-1-LAI (Barre-Sinoussi, F et al. (AIDS). Science 1983, 220, 868). After 7 days of culture, viral replication was quantified by measuring the enzymatic activity of the RT in the cell culture supernatants by means of the Retrosys® kit (Innovagen). Cytoxicity of the molecules was evaluated in parallel by an MTT test in cultures of uninfected cells. The 50% effective concentration (EC50) and the 50% cytotoxic concentration (TC50) were calculated by means of the SoftMax Pro® 6.6 software (Molecular Devices).

The results are presented in Tables VI and VII below:

TABLE VI

Activity and cytotoxicity of S-PMEA 6 and reference compound PMEA against HIV-1 (LAI) in infected cell cultures.

| Compound | $EC_{50}$ (µM) HIV-1 (LAI) | $TC_{50}$ (µM) | IT |
|---|---|---|---|
| S-PMEA 6 | 7.0 | >42 | >6 |
| PMEA | 1.9 | >19 | >5 |

[*$EC_{50}$: effective concentration at 50%.
**$TC_{50}$: cytotoxic concentration.
***SI = selectivity index: ratio of the cytotoxicity ($TC_{50}$) to the efficacy ($EC_{50}$). The more the selectivity index is high the more the compound is efficient.

The results show that S-PMEA derivative 6 presents an antiviral activity slightly less than those of PMEA but with a better selectivity index due to a lower cytotoxicity.

TABLE VII

Activity and cytotoxicity of S-PMPA 11 and reference compound PMPA against HIV-1 (LAI) in infected cell cultures.

| Compound | $EC_{50}$ (µM) HIV-1 (LAI) | $TC_{50}$ (µM) | IT |
|---|---|---|---|
| S-PMPA 11 | 1.6 | >100 | >63 |
| PMPA | 1.3 | >100 | >77 |

[*$EC_{50}$: effective concentration at 50%.
**$TC_{50}$: cytotoxic concentration.
***SI = selectivity index: ratio of the cytotoxicity ($TC_{50}$) to the efficacy ($EC_{50}$).

S-PMPA 11 is active and its activity is comparable to that of PMPA. The S-PMPA is not cytotoxic (highest concentration tested: 200 µM). Selectivity index are equivalent (S-PMPA versus PMPA).

3) Anti-HIV Test on Resistant Viruses

The efficacy of compounds 6 and 11 can also be evaluated against resistant viruses in CEM cells (human lymphocytes) in culture. For example, the following protocole can be used: CEM cells (2-3×10³ cells per ml) are cultured in 96-well microplates (200 µl) in the presence of a range of concentrations of compounds 6, 11 and reference compounds PMEA and PMPA, in culture medium, infected by 100 $CCID_{50}$ of HIV-1 and incubated at 37° C. After 4 days, the formation of giant cells is measured with the microscope in the different cell cultures. The $EC_{50}$ value corresponds to the effective concentration required to reduce by 50% the formation of syncytia by the cultures of infected CEM cells.

Several clinical isolates of HIV-1 (provided by Kristel Van Laethem, Rega Institute for Medical Research; Schmit J-C, et al. Antiviral Therapy 1998; 3: 81-8. Van Laethem K, et al. AIDS 2000; 14: 469-71) containing mutations for resistance to several inhibitors of reverse transcriptase (RT) are tested to study their sensitivity to the target compounds in CEM cultures, as described above. The following mutations are present in the RT of the isolated viruses: HIV-1/C19: M41L+V118I+L210W+T215Y; HIV-1/C20: M41L+D67N+V118I+M184V+L210W+T215Y; HIV-1/L6.5: S68G+K70T+V75I+F77L+K103N+F116Y+Q151M+K219R; HIV-1/DE434.4: K65R+S68G+T69I+V75T+Q151M; HIV-1/HA20.17: A62V+V75I+F77L+Q151M+M184V.

4) Tests Against a Panel of Viruses

Compounds 6 and 11 were also evaluated for antiviral activity against a panel of viruses including:

herpes simplex virus type 1 (HSV-1, KOS and KOS ACV TK-) and type 2 (HSV-2, G), vaccinia virus, vesicular stomatitis virus in HEL cells;

Coxsackie B4 virus and respiratory syncytial virus in Hela cells;

Parainfluenza-3-virus, Reovirus-1, Sindbis virus, Coxsackie B4 and Punta Toro virus in Vero cells;

influenza A (H1N1), influenza A (H3N2), influenza B, in MDCK cells;

Feline Corona virus and Feline Herpes virus in CRFK cells.

Anti-HSV-1 and HSV-2, Vaccinia virus and Vesicular stomatitis virus assays in HEL cells. Anti-Coxsackie virus B4 and Respiratory Syncytial virus in HeLa cells. Anti-Parainfluenza-3-virus, Reovirus-1, Sindbis virus and Punta Toro virus in Vero cells. Human embryonic lung (HEL) (ATCC-CCL 137), simian kidney (Vero) and human cervix carcinoma (HeLa) cells were propagated in minimal essential medium (MEM) supplemented with 10% fetal calf serum (FCS), 2 mM L-glutamine, and 0.075% bicarbonate. Herpes simplex virus type 1 (HSV-1) (KOS and KOS ACV TK-), HSV-2 (G), vaccinia virus and vesicular stomatitis virus were assayed in HEL cell cultures; Coxsackie virus B4 and respiratory syncytial virus in HeLa cell cultures, and parainfluenza-3 virus, reovirus-1, Sindbis virus and Punta Toro virus in Vero cell cultures. Cells were grown to confluency in microtiter trays and were inoculated with 100 times the 50% cell culture infective dose. Compounds, either alone or in combination, were added after a 1 to 2-h virus adsorption period. The virus-induced cytopathic effect (CPE) was recorded microscopically at =3 days post-infection and were expressed as percentage of the untreated controls. The 50% effective concentrations ($EC_{50}$) were derived from graphical plots. The minimal toxic concentration (MTC) was defined as the minimal concentration that resulted in a microscopically detectable alteration of cell morphology. The MTC was determined in uninfected confluent cell cultures that were incubated, akin to the cultures used for the antiviral assays, with serial dilutions of the compounds for the same time period. Cultures were inspected microscopically for alteration of cell morphology.

No significant cytotoxicities were reported for any of the compounds 6 and 11 up to 200 µM. Compounds 6 and 11 exhibited no in vitro antiviral activity up to 200 µM against vesicular stomatitis virus Coxsackie B4, respiratory syncytial virus, influenza A ($H_1N_1$), influenza A (H3N2), influenza B, Parainfluenza-3-virus, Reovirus-1, Sindbis virus and Punta Toro virus. Compound 6 displayed a moderate activity against Feline Herpes virus ($EC_{50}$=38 µM) and Herpes simplex virus-2 (G) (($EC_{50}$=58 µM).

Example 12

Evaluation of Phosphonate-Diphosphate Derivatives 12 and 13 on the Inhibition of Reverse Transcriptase (RT)

The catalytic mechanism of incorporation of the thiophosphonate diphosphate analogues 12 and 13 was evaluated in the laboratory by means of the techniques of pre-stationary kinetics, in order to determine the dissociation constant (Kd) of the thiophosphonate diphosphate analogue for the RT, and the catalytic constant for creation of the phosphodiester bond (Kpol). These studies also make it possible to calculate the discrimination of the thiophosphonate diphosphate derivatives with respect to the corresponding unmodified derivatives.

The analogues were tested on the wild-type RT and on the K65R mutant.

The bacterial construction p66RTB expressing the gene for the wild-type RT was used to obtain RT K65R as described in Boretto et al. (*Anal. Biochem.*, 2001, 292(1), 139-47). All constructions were verified by DNA sequencing. The recombinant RTs were co-expressed with the protease of HIV-1 in *Escherichia coli* so as to obtain the heterodimers p66/p51, which were subsequently purified by affinity chromatography. All enzymes are quantified by titration of the active sites before any biochemical study.

Kinetic studies were carried out by using dATP, PMEApp, PMPApp, S-PMEApp (12) and S-PMPApp (13) on wild-type RT and K65R mutant RT. Pre-stationary kinetic experiments were carried out by means of a KINTEK model RQF-3 apparatus on reaction times from 10 ms to 30 s. All indicated concentrations correspond to final concentrations.

The DNA/RNA oligonucleotides used for the reaction correspond to a 5'-marked primer of 21 bases (5'-ATA CTT TAA CCA TAT GTA TCC-3') hybridized with a template of 31 bases (31A-RT; 5'-AAA AAA AAA TGG ATA CAT ATG GTT AAA GTA T-3'). For the natural nucleotides, the reaction was carried out by mixing a solution comprising 50 nM (in active sites) of HIV-1 RT bound to 100 nM of primer/matrix complex in RT buffer (50 mM Tris-HCl, pH 8.0, 50 mM KCl, 0.05% Triton X-100) and a variable NTP concentration with 6 mM $MgCl_2$. The reactions involving acyclic nucleotides were carried out with an excess of enzyme (200 nM) with respect to the primer/template complex (100 nM). These conditions were chosen to eliminate the effect of the turnover ratio of the enzyme ($k_{ss}$) which interferes with the measurement of low levels of incorporation. The reaction products were analyzed on an electrophoresis gel (14% acrylamide, 8 M urea in TBE buffer) and quantified after visualization on a FUJIIMAGER®.

The kinetic constants were measured for dATP (natural nucleotide), PMEA diphosphate (PMEApp), PMPA diphosphate (PMPApp) and thiophosphonate diphosphate analogues (12) and (13), on the wild-type RT of HIV-1 and on that resistant to PMPA, the K65R mutant.

The formation of product (P) over time was determined with the following equation:

$$(P) = A \cdot (1 - \exp(-(k_{app} \cdot t))) + k_{ss} \cdot t \quad \text{(Eq. 1)}$$

where A is the amplitude of the peak, $k_{app}$ is the apparent kinetic constant of formation of the phosphodiester bond and $k_{ss}$ is the turnover level of the enzyme (the kinetic constant of the linear phase in steady-state). The dependence of $k_{app}$ with respect to the dNTP concentration is described by the following hyperbolic equation:

$$k_{app} = k_{pol} dNTP / (K_d + dNTP) \quad \text{(Eq. 2)}$$

where $K_d$ and $k_{pol}$ are the equilibrium and catalytic constants of the dNTP for the RT respectively. $K_d$ and $k_{pol}$ were determined by curve fitting using the KALEIDAGRAPH software (SYNERGY SOFTWARE).

The results obtained are brought together in Table VIII below:

TABLE VIII

Pre-stationary kinetic constants for dATP (natural nucleotide), PMEA diphosphate (PMEApp), PMPA diphosphate (PMPApp) and thiophosphonate diphosphate analogues (12) and (13), on the wild-type RT of HIV-1 and on the K65R mutant:

| RT | Nucleotide | $K_d$ (µM) | $k_{pol}$ (s⁻¹) | $k_{pol}/K_d$ | Selectivity | Resistance |
|---|---|---|---|---|---|---|
| Wild-type | dATP | 7.47 | 50.16 | 6.71 | | |
| | PMEApp | 7.9 | 6.8 | 0.86 | 7.8 | |
| | PMPApp | 23 | 7 | 0.3 | 22.3 | |
| | S-PMEApp 12 | 1.2 | 0.55 | 0.5 | 14.5 | |
| | S-PMPApp 13 | 5.2 | 0.58 | 0.11 | 59.8 | |

TABLE VIII-continued

Pre-stationary kinetic constants for dATP (natural nucleotide), PMEA diphosphate (PMEApp), PMPA diphosphate (PMPApp) and thiophosphonate diphosphate analogues (12) and (13), on the wild-type RT of HIV-1 and on the K65R mutant:

| RT | Nucleotide | $K_d$ (µM) | $k_{pol}$ (s⁻¹) | $k_{pol}/K_d$ | Selectivity | Resistance |
|---|---|---|---|---|---|---|
| K65R Mutant | dATP | 6.89 | 11.63 | 1.69 | | |
| | PMEApp | 7.7 | 0.75 | 0.1 | 16.9 | 2.16 |
| | PMPApp | 18 | 0.32 | 0.017 | 99.4 | 4.45 |
| | S-PMEApp12 | 0.7 | 0.03 | 0.04 | 41 | 2.8 |
| | S-PMPApp13 | 2.7 | 0.077 | 0.03 | 61 | 1 |

Selectivity = ($k_{pol}/K_d$) natural nucleotide/($k_{pol}/K_d$) nucleotide analogue.
Resistance = Selectivity mutant RT/Selectivity wild-type RT
Resistance > 1: enzyme resistant to the nucleotide
Resistance < 1: enzyme sensitive to the nucleotide dATP is the natural nucleotide of reference, from which selectivity can be calculated. All nucleotide analogues tested are substrates and inhibitors of the RT of wild-type HIV-1 and the K65R mutant. They are incorporated and are chain terminators.

Wild-type RT discriminates PMEADP and PMPADP 7.8 and 22 times. This discrimination is even more marked for the thiophosphonate-diphosphate analogues 12 and 13, since it is respectively 14.5 and 59.8 times. This strong discrimination is explained by the incorporation velocities of S-PMEApp (12) and S-PMPApp (13) by RT that are 90 times lower than that of the natural nucleotide dATP. This loss is not compensated by the affinities of the RT for these analogues, however better: 1.2 versus 7.5 for S-PMEApp (12) and 5.5 versus 7.5 for S-PMPApp (13).

The K65R mutant is, respectively, 2.16 times and 4.45 times resistant to PMEApp and PMPApp. This resistance is principally due to a reduction in the incorporation velocity of the nucleotide (factor 9 and 22). The K65R mutant is also resistant to S-PMEApp (12) (R=2.8) and this for the same reason: reduction of the incorporation velocity by a factor of 18. This resistance factor is identical to that observed for the non-thio analogue PMEApp (R=2.2).

On the other hand, the K65R mutant is no longer resistant to S-PMPApp (13) (R=1) and compared to the PMPApp analogue, not carrying a sulphur atom on the phosphonate, it reduces the resistance (R=4.4), which justifies the interest in thiophosphonate compounds in the fight against resistance.

2) Evaluation of the Resistance to Excision of S-PMEA (6) and S-PMPA (11) Derivatives Incorporated in a DNA Primer by Wild-Type RT and Mutant RT (D67N, K70R, T215F, K219Q). Study by ATP Lysis.

a) production and purification of DNA primers incorporating PMEA, PMPA, S-PMEA and S-PMPA. (See FIG. 1)

All constructions were verified by DNA sequencing. The recombinant RTs were co-expressed with the HIV-1 protease in *Escherichia coli* so as to obtain the p66/p51 heterodimers, which were subsequently purified by affinity chromatography. All enzymes were quantified by titration of the active sites before any biochemical study.

The DNA/DNA oligonucleotides used for the reaction correspond to a primer of 21 bases (5'-ATA CTT TAA CCA TAT GTA TCC-3') hybridized with a template of 31 bases (5'-AAA AAA AAA TGG ATA CAT ATG GTT AAA GTA T-3') at 5 µM. The reaction was carried out by mixing a solution comprising 20 µM of HIV-1 RT in RT buffer (50 mM Tris-HCl, pH 8.0, 50 mM KCl, 0.05% Triton X-100, 100 µM $MgCl_2$) and 10 mM PMEApp or PMPApp or S-PMEApp 12 or S-PMPApp 13. The reaction was incubated 50 minutes at 37° C. Each reaction was stopped by heating at 70° C. for 5 minutes. The 22mer products, derived from the RT elongation reaction, were then purified by reverse-phase HPLC. The apparatus used possesses an in-line filtration system (pre-column+switch) which makes it possible to inject a protein-rich mixture into the analytical column without prior filtration. After purification, the collected fractions of each 22mer were combined, lyophilized, and characterized by mass spectrometry (MALDI-TOF). Their concentration was determined by measuring $OD_{260}$.

| 22mer | HPLC (min) | [M-H]⁻ (g mol⁻¹) | Quantity (nmol) |
|---|---|---|---|
| PMEA-22mer | 31.6 | 6592 | 1.149 nmoles |
| PMPA-22mer | 32.8 | 6606 | 0.960 nmoles |
| S-PMEA-22mer | 32.8 | 6608 | 1.267 nmoles |
| S-PMPA-22mer | 32.9 | 6623 | 1.177 nmoles | b) Experiments. Results.

The DNA/DNA oligonucleotides used for the reaction corresponded to a 22 base primer marked in 5' with $^{32}P$ (5'-ATA CTT TAA CCA TAT GTA TCC-3', PMEA-22mer or PMPA-22mer or S-PMEA-22mer or S-PMPA-22mer) hybridized with a matrix of 31 bases (5'-AAA AAA AAA TGG ATA CAT ATG GTT AAA GTA T-3'). The reaction was carried out by mixing a solution comprising 100 nM of the RT of wild-type HIV-1 or mutant HIV-1 (D67N, K70R, T215F, K219Q) bound to 50 nM of primer/matrix complex in RT buffer (50 mM Tris-HCl, pH 8.0, 50 mM KCl, 0.05% Triton X-100) and an ATP concentration of 3.2 mM with 5 mM $MgCl_2$. The reaction was incubated for 2 hours at 37° C. and samples were taken for analysis at 1 hr. and 2 hr. The reaction products were analyzed on an electrophoresis gel (14% acrylamide, 8 M urea in TBE buffer) and quantified after visualization on a FUJIIMAGER®.

Thiophosphonate derivatives S-PMEA and S-PMPA were less excised than the derivatives PMEA and PMPA, whether with wild-type RT or with resistant RT (D67N, K70R, T215F, K219Q). See FIG. 2.

With wild-type RT, after 2 hours of reaction, only 4% of the S-PMEA-22mer was transformed into 21mer and 10% in the case of the S-PMPA-22mer. Respectively, 41% and 34% in the case of the 22mers PMEA-22mer and PMPA-22mer were transformed into 21mer.

With resistant RT (D67N, K70R, T215F, K219Q), after 2 hours of reaction, only 19% of the S-PMEA-22mer was transformed into 21mer and 20% in the case of the S-PMPA-22mer. Respectively, 55% and 57% in the case of the 22mers PMEA-22mer and PMPA-22mer were transformed into 21mer.

The thiophosphonate modification therefore offers a favourable effect on excision, which is highly reduced, and this justifies all interest in the thiophosphonate compounds for fighting against HIV resistance.

Example 13

Stability Study of Thiophosphonate Derivatives 6 and 11 Under Conditions Mimicking Biological Fluids A stability study of S-PMEA (6) and S-PMEA (11) derivatives was carried out under conditions mimicking biological fluids: in complete medium (extra-cellular medium mimic) and in total cell extracts (intra-cellular medium mimic).

Media and preparation of cell extracts. Culture medium was composed by RPMI 1640 containing 10% (v/v) heat-inactivated fetal calf serum and stored at −80° C. CEM-SS cell extracts were prepared according to a published procedure (Puech, F. et al. *Antiv. Res.* 1993, 22, 155-174). Exponentially growing CEM-SS cells were recovered by centrifugation (500 g, 4° C., 4 min), washed twice with PBS and resuspended in 10 mM Tris-HCl, 140 mM KCl (pH 7.4), at the concentration of 30×10⁶ cells/mL. Cells were lyzed by ultrasonic treatment and cellular debris were removed by centrifugation (10000 g, 4° C., 20 min). The supernatant containing soluble proteins (3 mg/mL) was stored at −80° C.

HPLC Analysis.

The degradation kinetics were followed by analytical HPLC. The apparatus used possesses a specific on-line filtration system.

Kinetic data and decomposition pathways for compounds 6 and 11 were studied at 37° C. (a) in complete medium (RPMI 1640 containing 10% heat-inactivated fetal calf serum (b) in total cells extracts (CEM-SS). For each kinetic study, the compound solution was diluted with a freshly thawed aliquot of the considered medium to obtain an initial concentration of 0.1 mM. The mixture was incubated at 37° C. and for the required time, an aliquot (10% solution) was taken and immediately frozen at −80° C. for further HPLC analysis. The crude sample was injected into the precolumn and eluted with buffer A during 5 min. Then, the switching valve for connecting the precolumn to the column was activated, and a linear gradient from buffer A to buffer B, increasing buffer B from 0% at 0 min to 20% at 40 min is applied. The retention times were 6, 26 min; 11, 29.5 min, PMEA, 24.3 min and (R)-PMPA, 27.8 min.

All the compounds were analyzed under the same conditions. The amount of remaining parent compound at each time point was used to determine the half-life of the compound. The product of degradation from parent compound was determined by comparison with corresponding references.

The half-lives were calculated and are gathered together in Table IX below:

TABLE IX

Stability study. $t_{1/2}$: half-life of decomposition of the compounds 6 and 11 in various media

| No. | Structure | $t_{1/2}$ complete medium | $t_{1/2}$ cell extracts |
|---|---|---|---|
| 6 | (structure shown) | >24 hr[a] | stable[c] |

TABLE IX-continued

Stability study. $t_{1/2}$: half-life of decomposition of the compounds 6 and 11 in various media

| No. | Structure | $t_{1/2}$ complete medium | $t_{1/2}$ cell extracts |
|---|---|---|---|
| 11 | [structure of compound 11: adenine-CH2-CH(—)-O-CH2-P(=S)(O⁻Na⁺)(O⁻Na⁺)] | >24 hr[b] | stable[c] |

[a]: product 80% intact (degradation into PMEA)
[b]: product 77% intact (degradation into PMPA)
[c]: less than 1% degradation after 24 hr.

Compounds 6 and 11 behave similarly under the conditions tested (culture medium and cell extracts). Compound 6 was slowly degraded into a single product, identified as being the phosphonate PMEA by HPLC co-injection. Compound 11 was slowly decomposed into a single product, identified as being the phosphonate PMPA by HPLC co-injection. This conversion is due to a de-sulphurisation of the P—S bond into a P—O bond. The difference in behaviour observed in culture medium (20% degradation) and in cell extracts (less than 1% degradation) can be explained by the difference in enzymatic content between the two media; the culture medium containing 10% foetal calf serum.

Figure 1:
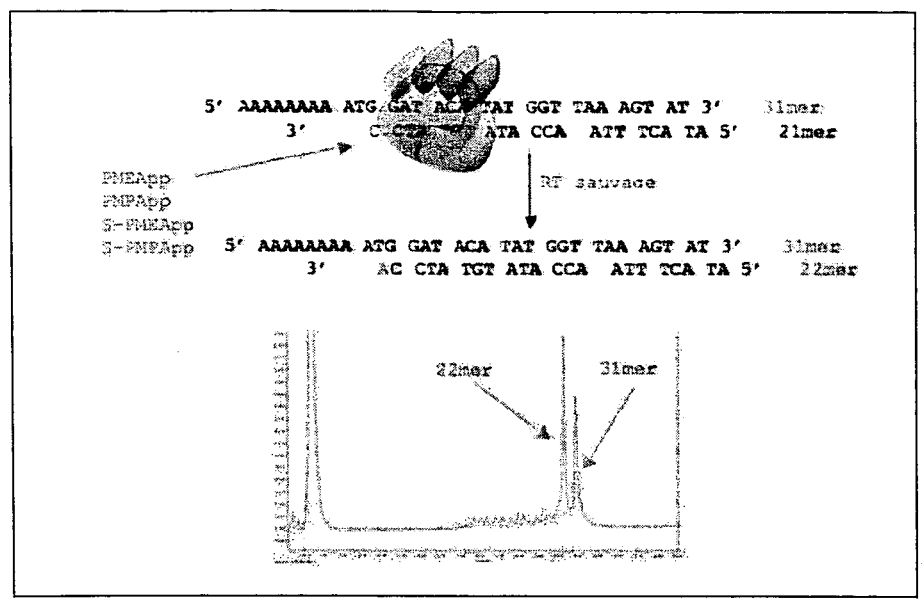
FIG. 1: Elongation principle of 22mer primers by wild-type RT from 21mer primers. Incorporation of PMEApp or PMPApp or S-PMEApp 12 or S-PMPApp 13 for production of the 4 elongated 22mer substrates. Purification of the products formed by HPLC.
Figure 2:
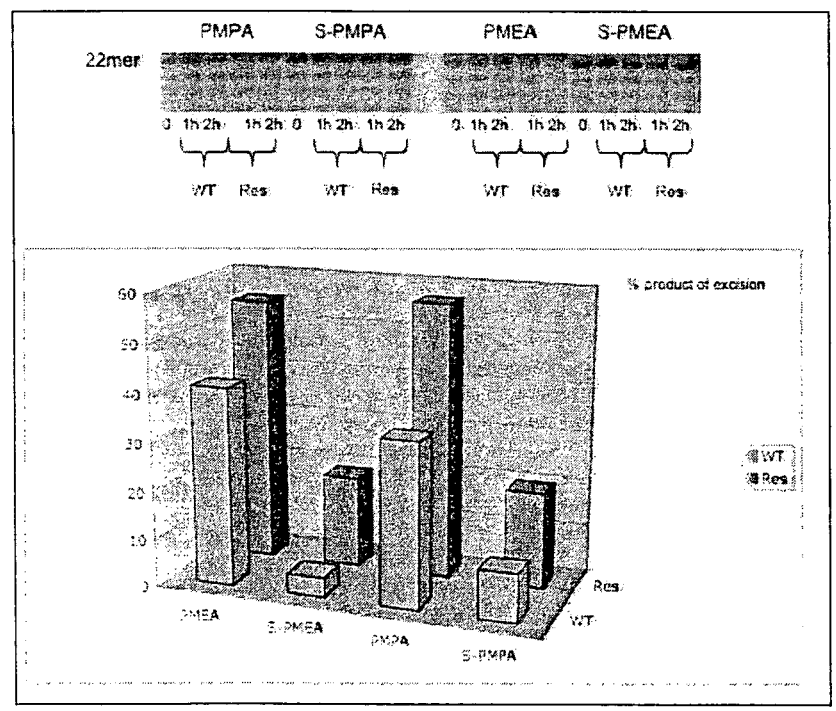
FIG. 2: Electrophoresis gel after visualization of the reaction products. Evaluation of the percentage of excised product. WT: Wild-type RT, Res: Resistant RT (D67N, K70R, T215F, K219Q).

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A purine phosphonate compound of formula (I) as follows:

[structure of formula (I): B-CH2-CH(R1)-O-CH2-P(=X)(R2)(R3)]

(I)

or pharmaceutically acceptable salt thereof; wherein:
B is a base selected from the group consisting of adenine, xanthine, hypoxanthine, guanine, 8-bromo-guanine, 8-chloroguanine, 8-aminoguanine, 8-hydrazinoguanine, 8-hydroxyguanine, 8-methylguanine, 8-thioguanine, 2-aminopurine, and 2,6-diaminopurine;
$R^1$ is selected from the group consisting of a hydrogen atom, and a methyl, ethyl, hydroxymethyl, hydroxyethyl and $C_{1-6}$haloalkyl group;
$R^3$ is selected from the group consisting of a hydroxyl group or alkaline metal salt thereof, —$OR^{3A}$, a prodrug moiety, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkenyl group, an amino acid residue, and an amine group R"HN, wherein $R^{3A}$ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, —P(=O)(OH)$_2$ or alkaline metal salt thereof, or —P(=O)(OH)OP(=O)(OH)$_2$ or alkaline metal salt thereof, and R" is a linear or branched $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkynyl, or $C_{6-10}$aryl group; and
(a) X is selected from the group consisting of a selenium atom and a sulphur atom, and $R^2$ is selected from the group consisting of a fluorine atom, a hydroxyl group or alkaline metal salt thereof, —$OR^{2A}$, a prodrug moiety, $BH_3^-$, a linear or branched $C_{1-8}$alkyl, $C_{2-8}$alkenyl, $C_{2-8}$alkynyl, $C_{1-8}$heteroalkyl, $C_{2-8}$heteroalkenyl or $C_{2-8}$heteroalkynyl group, an amino acid residue, and an amine group R'HN wherein $R^{2A}$ represents $C_{1-8}$alkyl, $C_{2-8}$alkenyl, $C_{2-8}$alkynyl, $C_{1-8}$heteroalkyl, $C_{2-8}$heteroalkenyl, $C_{2-8}$heteroalkenyl, —P(=O)(OH)$_2$ or alkaline metal salt thereof, —P(=O)(OH)OP(=O)(OH)$_2$, or alkaline metal salt thereof, and R' is a linear or branched $C_{1-8}$heteroalkyl, $C_{2-8}$heteroalkenyl, $C_{2-8}$heteroalkynyl, or $C_{6-10}$aryl; or
(b) X represents an oxygen atom, and $R^2$ is selected from the group consisting of a fluorine atom and a $BH_3^-$ group.

2. A compound as claimed in claim 1, wherein B is a base selected from the group consisting of adenine and guanine.

3. A compound as claimed in claim 1 wherein $R^1$ is selected from the group consisting of a hydrogen atom, a methyl group, a hydroxymethyl and a fluoromethyl group.

4. A compound as claimed in claim 1, wherein the compound has the following structure:

[structure: B-CH2-CH(R1)-O-CH2-P(=S)(OR5A)(OR4A)]

wherein $R^{4A}$ and $R^{5A}$ are independently a hydrogen atom or an alkaline metal cation.

5. A compound as claimed in claim 1, wherein the compound has the following structure:

[structure: B-CH2-CH(R1)-O-CH2-P(=S)(OR4A)-O-P(=O)(OR4B)(OR5B)]

wherein $R^{4A}$, $R^{4B}$, and $R^{5B}$ are independently a hydrogen atom or an alkaline metal cation.

6. A compound as claimed in claim 1, wherein the compound has the following structure:

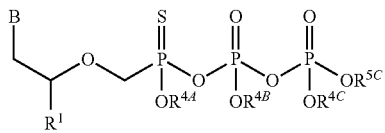

wherein $R^{4A}$, $R^{4B}$, $R^{4C}$, and $R^{5C}$ are independently a hydrogen atom or an alkaline metal cation.

7. A compound as claimed in claim 1, wherein the compound has one of the following structures:

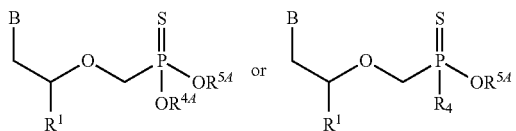

wherein
$R^{4A}$ is an enzyme-labile group selected from the group consisting of —CH$_2$OC(=O)CH(CH$_3$)$_2$, —CH$_2$OC(=O)C(CH$_3$)$_3$, —CH$_2$CH$_2$SC(=O)C(CH$_3$)$_3$ and —CH$_2$CH$_2$SC(=O) CH$_3$;
$R^4$ is selected from the group consisting of an amino acid residue selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine, and an amine group —NHR', wherein R' is a linear or branched C$_{1-8}$alkyl, C$_{1-8}$heteroalkyl or C$_{6-10}$aryl; and
$R^{5A}$ is a hydrogen atom or an alkaline metal cation.

8. A compound as claimed in claim 1, wherein the compound has one of the following structures:

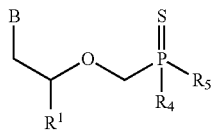

wherein
$R^4$ is selected from the group consisting of —OR$^{4A}$, an amino acid residue selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine, and an amine group —NHR';
$R^5$ is selected from the group consisting of —OR$^{5A}$, an amino acid residue selected from the group consisting of alanine, argnine, asparagine, aspartic acid, cysteine, glutamic acid, glutamine, glycine, histidine, isoleucine, leucine, lysine, methionine, phenylalanine, proline, serine, threonine, tryptophan, tyrosine, and valine and an amine group —NHR'';
wherein $R^{4A}$ and $R^{5A}$ are independently an enzyme-labile group selected from the group consisting of —CH$_2$OC(=O)OCH(CH$_3$)$_2$, —CH$_2$OC(=O)C(CH$_3$)$_3$, —CH$_2$CH$_2$SC(=O)C(CH$_3$)$_3$ and —CH$_2$CH$_2$SC(=O) CH$_3$; and R' and R'' are independently a linear or branched C$_{1-8}$alkyl, C$_{1-8}$heteroalkyl or C$_{6-10}$aryl group.

9. A compound as claimed in claim 1, wherein the compound has the following structure:

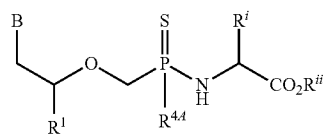

wherein $R^{4A}$ is a hydrogen atom, an alkaline metal cation or C$_{1-8}$alkyl;

$R^i$ is a hydrogen atom or an amino acid side chain; and $R^{ii}$ is a hydrogen atom, an alkaline metal cation or C$_{1-8}$alkyl.

10. A compound as claimed in any one of claims 4 to 9, wherein B is adenine.

11. A compound as claimed in any one of claims 4 to 9, wherein $R^1$ is hydrogen.

12. A compound as claimed in any one of claims 4 to 9, wherein $R^1$ is methyl or ethyl and the carbon atom bearing $R^1$ has an R-configuration.

13. A compound as claimed in any one of claims 4 to 9, wherein $R^1$ is hydroxymethyl or hydroxyethyl and the carbon atom bearing $R^1$ has an S-configuration.

14. A compound as claimed in any one of claims 4 to 9, wherein $R^1$ is —CH$_2$F and the carbon atom bearing $R^1$ has an R- or S-configuration.

15. A compound as claimed in claim having one of the following structures:

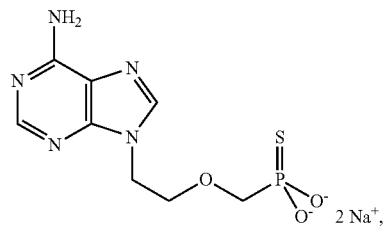

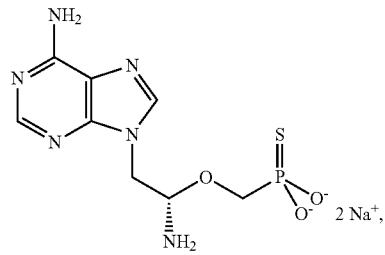

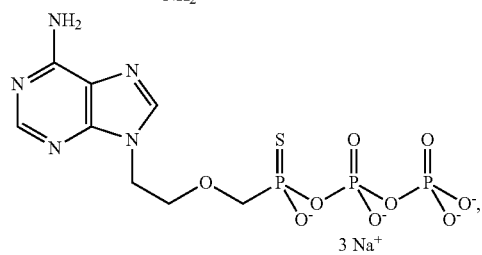

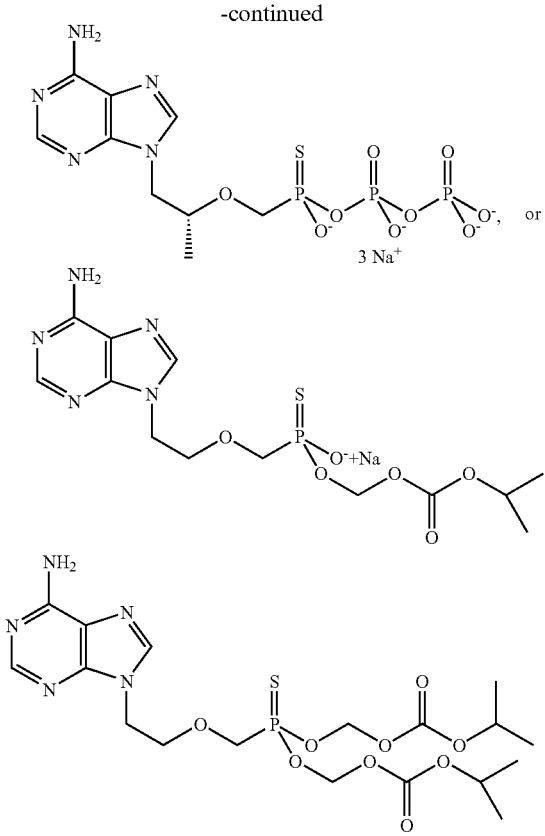
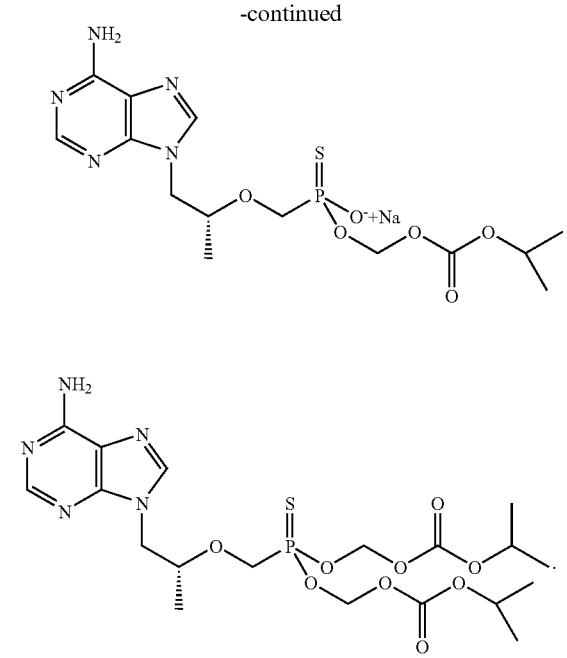
16. A pharmaceutical composition comprising a carrier and a purine phosphonate compound as claimed in claim 1.
17. A medicament comprising a carrier and a purine phosphonate compound as claimed in claim 1.
\* \* \* \* \*